United States Patent
Weltzin et al.

(10) Patent No.: US 6,576,244 B1
(45) Date of Patent: Jun. 10, 2003

(54) LT AND CT IN PARENTERAL IMMUNIZATION METHODS AGAINST HELICOBACTER INFECTION

(75) Inventors: Richard A. Weltzin, Lunenburg, MA (US); Bruno Guy, Lyons (FR)

(73) Assignee: Acambis, Inc., Cambridge, MA (US)

(*) Notice: Subject to any disclaimer, the term of this patent is extended or adjusted under 35 U.S.C. 154(b) by 0 days.

(21) Appl. No.: 09/336,115

(22) Filed: Jun. 18, 1999

Related U.S. Application Data

(63) Continuation-in-part of application No. 09/100,258, filed on Jun. 19, 1998.

(51) Int. Cl.$^7$ .............................................. A61K 39/02
(52) U.S. Cl. .............................. 424/234.1; 424/236.1; 424/184.1; 424/94.6; 514/12; 530/350; 530/403
(58) Field of Search .......................... 424/234.1, 236.1, 424/184.1, 94.6; 435/7.1, 252.8; 530/350, 403; 514/12

(56) References Cited

U.S. PATENT DOCUMENTS

| | | | |
|---|---|---|---|
| 4,053,584 A | * 10/1977 | Dobrescu et al. | 424/92 |
| 4,303,638 A | * 12/1981 | Tayot et al. | 424/32 |
| 4,411,888 A | 10/1983 | Klipstein et al. | 424/92 |
| 4,808,700 A | 2/1989 | Anderson et al. | 530/403 |
| 5,079,165 A | 1/1992 | Clements et al. | 435/252.8 |
| 5,182,109 A | 1/1993 | Tamura et al. | 424/92 |
| 5,241,053 A | 8/1993 | Fujisawa et al. | 424/89 |
| 5,308,835 A | 5/1994 | Clements | 514/12 |
| 5,538,729 A | 7/1996 | Czinn et al. | 424/234.1 |
| 5,837,240 A | 11/1998 | Lee et al. | 424/94.6 |
| 5,837,472 A | 11/1998 | Labigne | 435/7.1 |
| 5,843,460 A | * 12/1998 | Labigne et al. | 424/234.1 |
| 5,871,749 A | * 2/1999 | Doidge et al. | 424/234.1 |
| 5,980,898 A | * 11/1999 | Glenn et al. | 424/184.1 |
| 6,005,090 A | * 12/1999 | Doidge et al. | 536/23.5 |
| 6,126,938 A | * 10/2000 | Guy et al. | 424/184.1 |

FOREIGN PATENT DOCUMENTS

| | | |
|---|---|---|
| EP | 835928 A1 * | 4/1998 |
| WO | WO 92/19265 | 11/1992 |
| WO | WO 93/13202 | 7/1993 |
| WO | WO 93/20843 | 10/1993 |
| WO | WO 94/09823 | 5/1994 |
| WO | WO 95/17211 | 6/1995 |
| WO | WO 95/22987 | 8/1995 |
| WO | 96/31235 * | 10/1996 |
| WO | WO 96/33732 | 10/1996 |
| WO | WO 98/28357 | 7/1998 |

OTHER PUBLICATIONS

Atherton, JC et al, The Jordan Report, Accelerated Development of Vaccines, 1995, pp. 60–63.*

Blaser, Martin J., Trends in Microbiology, vol. 1(7), Oct. 1993, pp. 255–260.*

Chen, M et al, Gastroentrology, vol. 104(4), p. 681, Apr. 1993.*

Goodwin, C.S., Helicobacter pylori, Biology and Clinical Practice, Chapter 25, pp. 431–445, 1993.*

Guy, B et al, Vaccine Research, vol. 6(3), pp. 141–150, 1997.*

Haas, R et al, Biologicals, vol. 25, pp. 175–177, 1997.*

Lee, A et al, Infection Immunity, vol. 62(8), pp. 3594–3597, Aug. 1994.

Malfertheiner, P et al, Clinical Therapeutics, vol. 15(suppl. B), 1993.

Marchetti, M et al, Vaccine, vol. 16(1), pp. 33–37, 1998.

Radcliff, FJ et al, European Helicobacter pylori study group, Xth International Workshop on Gastroduodenal Pathology and Helicobacter pylori, Lisbon, Sep. 11–14, 1997, p. A60, abstract 06/213.

Telford, JL et al, Current Opinion, Drugs, Dec. 1996, vol. 52(6), pp. 799–804.

Varga Laszlo et al, Kazuisztika, pp. 359–361, issue 6, (english translation), 1992.*

Monath TP et al, Am. J. Gastroenterology, vol. 89(8), pp. 1383, 1994.*

Heap, K et al, Microb. Ecol. Health Dis, vol. 4, Oct. 7–10, 1991, p. S119, Vith International Workshop on Campylobacter, Helicobacter and Related Organisms.*

Bowen, JC et al, Immunology, Mar. 1994, vol. 81(3), pp. 338–342 (abstract).*

Hornquist, E et al, European J. Immunology, Sep. 1993, vol. 23(9), pp. 2136–2143.*

Bukanov et al, Molecular Biology, vol. 11(3), pp. 509–523, 1994.*

Tomb, J et al, Nature, vol. 388(7), pp. 539–547, Aug. 1997.*

Kaplan et al, South African Medical Journal, 1993, vol. 83(12), Dec. pp. 922–923*

Brzozowski, T et al, Gut, vol. 41(suppl 1, p. A30, 1997.*

Haines, DC et al, Vet. Pathology, May 1998, vol. 35(3), pp. 202–208.*

Chen et al., "Immunisation with Helicobacter. The First Evidence for Protection Against Gastric Infection," Irish Journal of Medical Science 161:29 (1992).

Chen et al., "Immunisation Against Gastric Helicobacter Infection in a Mouse/*Helicobacter felis* Model," The Lancet 339:1120–1121 (1992).

Clements et al., "Adjuvant Activity of *Escherichia coli* Heat–Labile Enterotoxin and Effect on the Induction of Oral Tolerance in Mice to Unrelated Protein Antigens," Vaccine 6:269–277 (1988).

(List continued on next page.)

Primary Examiner—Lynette R. F. Smith
Assistant Examiner—Ginny Allen Portner
(74) Attorney, Agent, or Firm—Clark & Elbing LLP

(57) ABSTRACT

This invention provides methods of inducing a protective or therapeutic immune response to Helicobacter infection in a mammal by parenterally administering to the mammal one or more Helicobacter antigens and an adjuvant selected from one or more of LT, CT, LTB, and CTB.

14 Claims, 11 Drawing Sheets

OTHER PUBLICATIONS

Corthesy—Theulaz et al., "*Helicobacter pylori* Urease Elicits Protection Against *Helicobacter felis* Infection in Mice," VIIth International Workshop on Campylobacter, Helicobacter, and Related Organisms, Acta Gastro–Enterologica Belgica 56:64 (1993).

Czerkinsky et al., "Oral Administration of a Streptococcal Antigen Coupled to Cholera Toxin B Subunit Evokes Strong Antibody Responses in Salivary Glands and Extramucosal Tissues," Infection and Immunity 57:1072–1077 (1989).

Czinn et al., "Oral Immunization Against *Helicobacter pylori*," Infection and Immunity 59:2359–2363 (1991).

Czinn et al., "Oral Immunization Protects Germ–Free Mice Against Infection from *Helicobacter felis*," Gastroenterology 102:A611 (1992).

Czinn et al., "Protection of Germ–Free Mice from Infection by *Helicobacter felis* After Active Oral or Passive IgA Immunization," Vaccine 11:637–642 (1993).

Davin et al., "*H. pylori* Urease Elicits Protection Against *H. felis* Infection in Mice," Gastroenterology 104:A1035 (1993).

Doidge et al., "Therapeutic Immunisation Against Helicobacter Infection," The Lancet 343:914–915 (1994).

Elson et al., "Generalized Systemic and Mucosal Immunity in Mice After Mucosal Stimulation with Cholera Toxin," The Journal of Immunology 132:2736–2741 (1984).

Elson et al., "Cholera Toxin Feeding Did Not Induce Oral Tolerance in Mice and Abrogated Oral Tolerance to an Unrelated Protein Antigen," The Journal of Immunology 133:2892–2897 (1984).

Elson, "Cholera Toxin (CT) as a Mucosal Adjuvant—The Effect of H–2 Genes," Fed. Proc., Abstract No. 1778 46:621 A (1987).

Elson, "Cholera Toxin and its Subunits as Potential Oral Adjuvants," Current Topics in Microbiology and Immunology 146:29–33 (1989).

Ermak et al., "MHC Class–II but not MHC–Class I or B Cell Responses are Required for Vaccine–Induced Protection Against Murine *Helicobacter pylori* Infection," European Study Group on Pathogenesis and Immunology in Helicobacter Infection, 3rd International Workshop on Pathogenesis and Host Response in Helicobacter Infections, LO–Skolen, Helsingor, Denmark, 1998, Abstract C3.

Ermak et al., "Immunization of Mice with Urease Vaccine Affords Protection Against *Helicobacter pylori* Infection in the Absence of Antibodies and Is Mediated by MHC Class–II–Restricted Responses," J. Exp. Med. 188:2277–2288 (1998).

Farahani et al., "Genomic Organization and Primary Characterization of miap–3: The Murine Homologue of Human X–Linked IAP," Genomics 42:514–518 (1997).

Gan et al., "Functional Characterization of the Internet Ribosome Entry Site of eIF4G mRNA," The Journal of Biological Chemistry 273:5006–5012 (1998).

Guy et al., "Systemic Immunization with Urease Protects Mice Against *Helicobacter pylori* Infection," Vaccine:850–856 (1998), vol. 16 (8).

Henney et al., "In Vivo Suppression of the Immune Response to Alloantigen by Cholera Enterotoxin," The Journal of Clinical Investigation 52:2853–2857 (1973).

Hirabayashi et al., "Comparison of Intranasal Inoculation of Influenza HA Vaccine Combined with Cholera Toxin B Subunit with Oral or Parenteral Vaccination," Vaccine 8:243–248 (1990).

Holmgren et al., "Cholera Toxin and Cholera B Subunit as Oral–Mucosal Adjuvant and Antigen Vector Systems," Vaccine 11:1179 (1993).

Holmgren et al., "Strategies for the Induction of Immune Responses at Mucosal Surfaces Making Use of Cholera Toxin B Subunit as Immunogen, Carrier, and Adjuvant," Am. J. Trop. Med. Hyg. 50:42–54 (1994).

Kateley et al., "Modulation of In Vivo Antibody Responses by Cholera Toxin," The Journal of Immunology 114:81–86 (1975).

Kleanthous et al., "Rectal and Intranasal Immunizations with Recombinant Urease Induce Distinct Local and Serum Immune Responses in Mice and Protect Against *Helicobacter pylori* Infection," Infection and Immunity 66:2879–2886 (1998).

Lee et al., "Oral Immunization with Recombinant *Helicobacter pylori* Urease Induces Secretory IgA Antibodies and Protects Mice from Challenge with *Helicobacter felis*," The Journal of Infectious Diseases 172:161–172 (1995).

Lee et al., "Immunization with Recombinant *Helicobacter pylori* Urease Decreases Colonization Levels Following Experimental Infection of Rhesus Monkeys," Vaccine 17:1493–1505 (1999).

Lindholm et al., "Interaction of Cholera Toxin and Toxin Derivatives with Lymphoctyes," Int. Archs. Allergy Appl. Immun. 50:555–573 (1976).

Lycke et al., "Strong Adjuvant Properties of Cholera Toxin on Gut Mucosal Immune Responses to Orally Presented Antigens," Immunology 59:301–308 (1986).

McKenzie et al., "Cholera Toxin B Subunit as a Carrier Protein to Stimulate a Mucosal Immune Response," The Journal of Immunology 133:1818–1824 (1984).

Michetti et al., "Immunization of BALB/c Mice Against *Helicobacter felis* Infection with *Helicobacter pylori* Urease," Gastroenterology 107:1002–1011 (1994).

Myers et al., "Oral Immunization with Recombinant *Helicobacter pylori* Urease Confers Long–Lasting Immunity Against *Helicobacter felis* Infection," Vaccine 17:1394–1403 (1999).

Nashar et al., "Current Progress in the Development of the B Subunits of Cholera Toxin and *Escherichia coli* Heat–Labile Enterotoxin as Carriers for the Oral Delivery of Heterologous Antigens and Epitopes," Vaccine 11:235–240 (1993).

Russell et al., "Distribution, Persistences, and Recall of Serum and Salivary Antibody Responses to Peroral Immunization with Protein Antigen I/II of *Streptococcus mutans* Coupled to the Cholera Toxin B Subunit," Infection and Immunity 59:4061–4070 (1991).

Saldinger et al., "Perspectives of Anti–*H. Pylori* Vaccination," Journal of Physiology and Pharmacology 48:59–65 (1997).

Spangler, "Structure and Function of Cholera Toxin and the Related *Escherichia coli* Heat–Labile Enterotoxin," Microbiological Reviews 56:622–647 (1992).

Stadtlander et al., "Immunogenicity and Safety of Recombinant *Helicobacter pylori* Urease in a Nonhuman Primate," Digestive Diseases and Sciences 41:1853–1862 (1996).

Tamura et al, "Effectiveness of Cholera Toxin B Subunit as an Adjuvant for Nasal Influenza Vaccination Despite Pre–Existing Immunity to CTB," Vaccine 7:503–505 (1989).

Tamura et al., "Protection Against Influenza Virus Infection by Vaccine Inoculated Intranasally with Cholera Toxin B Subunit," Vaccine 6:409–413 (1988).

Tamura et al., "Enhancement of Protective Antibody Responses by Cholera Toxin B Subunit Inoculated Intranasally with Influenza Vaccine," Vaccine 7:257–262 (1989).

Tamura et al., "Synergistic Action of Cholera Toxin B Subunit (and *Escherichia coli* Heat–Labile Toxin B Subunit) and a Trace Amount of Cholera Whole Toxin as a Adjuvant for Nasal Influenza Vaccine," Vaccine 12:419–426 (1994).

Tamura et al., "Protection Against Influenza Virus Infection by a Two–Dose Regimen of Nasal Vaccination Using Vaccines Combined with Cholera Toxin B Subunit," Vaccine 7:314–320 (1989).

Tamura et al., "Cross–Protection Against Influenza Virus Infection Afforded by Trivalent Inactivated Vaccines Inoculated Intranasally with Cholera Toxin B Subunit," The Journal of Immunology 149:981–988 (1992).

Tamura et al., "*Escherichia coli* Heat–Labile Enterotoxin B Subunits Supplemented with a Trace Amount of the Holotoxin as an Adjuvant for Nasal Influenza Vaccine," Vaccine 12:1083–1089 (1994).

Walker et al., "Use of Heat–Labile Toxin of Enterotoxigenic *Escherichia coli* to Facilitate Mucosal Immunization," Vaccine Research 2:1–10 (1993).

Warren et al., "In Vivo Suppression by Cholera Toxin of Cell–Mediated and Foreign Body Inflammatory Responses," The Journal of Immunology 112:996–1007 (1974).

Weltzin et al., "Novel Intranasal Immunization Techniques for Antibody Induction and Protection of Mice Against Gastric *Helicobacter felis* Infection," Vaccine 15:370–376 (1997).

Wilson et al., "Whole Cholera Toxin and B Subunit Act Synergistically as an Adjuvant for the Mucosal Immune Response of Mice to Keyhole Limpet Haemocyanin," Scand. J. Immunol. 31:443–451 (1990).

Wilson et al., "Adjuvant Effect of Cholera Toxin on the Mucosal Immune Response to Soluble Proteins (Differences Between Mouse Strains and Protein Antigens)," Scand. J. Immunol. 29:739–745 (1989).

Wu et al., "Induction of Mucosal Immunity by Intranasal Application of a Streptococcal Surface Protein Antigen with the Cholera Toxin B Subunit," Infection and Immunity 61:314–322 (1993).

Xu–Amano et al., "Helper Th1 and Th2 Cell Responses Following Mucosal or Systemic Immunization with Cholera Toxin," Vaccine 12:903–911 (1994).

* cited by examiner

SEQUENCE LISTING

<160> NUMBER OF SEQ ID NOS: 24

<210> SEQ ID NO 1
<211> LENGTH: 2798
<212> TYPE: DNA
<213> ORGANISM: Helicobacter pylori
<220> FEATURE:
<221> NAME/KEY: CDS
<222> LOCATION: (328)...(2451)
<220> FEATURE:
<221> NAME/KEY: sig_peptide
<222> LOCATION: (328)...(385)

<400> SEQUENCE: 1

```
tggtcctggc attccgaggt tcgaatcctt gcaccccagc cattttcct tatttttgg      60 cgcggagtag agcagtccgg tagctcgttg ggctcataac ccaaaggtca gtggttcaaa    120
tccattctcc gcaaccaatc ctttaaacca caccaccacc aaacgaacca acgaaacaa     180 aaagcatcaa aatcaaaaaa atgacaaaat ttttaagaaa atgacaaaaa aaaaaaaac    240 gattttatgc tatattaacg aaatcttgtg ataagatctt attcttttaa aagacttatc    300
taaccatttt aatttcaagg agaaaac atg aaa aaa acc ctt tta ctc tct ctc   354
                                Met Lys Lys Thr Leu Leu Leu Ser Leu
                                                              -15 tct ctc tct ctc tcg ttt ttg ctc cac gct gaa gac gac ggc ttt tac     402
Ser Leu Ser Leu Ser Phe Leu Leu His Ala Glu Asp Asp Gly Phe Tyr
-10                   -5                   1                   5 aca agc gtg ggc tat caa atc ggt gaa gcc gct caa atg gtg aaa aac     450
Thr Ser Val Gly Tyr Gln Ile Gly Glu Ala Ala Gln Met Val Lys Asn
              10                  15                  20 acc aaa ggc att caa gag ctt tca gac aat tat gaa aag ctg aac aat     498
Thr Lys Gly Ile Gln Glu Leu Ser Asp Asn Tyr Glu Lys Leu Asn Asn
          25                  30                  35 ctt ttg aat aat tac agc acc cta aac acc ctt atc aaa ttg tcc gct     546
Leu Leu Asn Asn Tyr Ser Thr Leu Asn Thr Leu Ile Lys Leu Ser Ala
      40                  45                  50
```

-continued

| | |
|---|---|
| gat ccg agc gcg att aac gac gca agg gat aat cta ggc tca agc tct<br>Asp Pro Ser Ala Ile Asn Asp Ala Arg Asp Asn Leu Gly Ser Ser Ser<br>55                   60                   65                  70 | 594 |
| agg aat ttg ctt gat gtc aaa acc aat tcc ccc gcg tat caa gcc gtg<br>Arg Asn Leu Leu Asp Val Lys Thr Asn Ser Pro Ala Tyr Gln Ala Val<br>                   75                   80                   85 | 642 |
| ctt tta gca ctc aat gct gca gtg ggg ttg tgg caa gtt aca agc tac<br>Leu Leu Ala Leu Asn Ala Ala Val Gly Leu Trp Gln Val Thr Ser Tyr<br>                   90                   95                  100 | 690 |
| gct ttt act gct tgt ggt cct ggc agt aac gag aat gcg aat gga ggg<br>Ala Phe Thr Ala Cys Gly Pro Gly Ser Asn Glu Asn Ala Asn Gly Gly<br>105                  110                  115 | 738 |
| atc caa act ttt aat aat gtg cca gga caa gat acg acg acc atc act<br>Ile Gln Thr Phe Asn Asn Val Pro Gly Gln Asp Thr Thr Thr Ile Thr<br>120                  125                  130 | 786 |
| tgc aat tcg tat tat gag cca gga cat ggt ggg cct ata tcc act gca<br>Cys Asn Ser Tyr Tyr Glu Pro Gly His Gly Gly Pro Ile Ser Thr Ala<br>135                  140                  145                  150 | 834 |
| aat tat gcg aaa atc aat caa gcc tat caa atc atc caa aag gct ttg<br>Asn Tyr Ala Lys Ile Asn Gln Ala Tyr Gln Ile Ile Gln Lys Ala Leu<br>                  155                  160                  165 | 882 |
| aca gcc aat gga gct aat gga gat ggg gtc ccc gtt tta agc aac acc<br>Thr Ala Asn Gly Ala Asn Gly Asp Gly Val Pro Val Leu Ser Asn Thr<br>170                  175                  180 | 930 |
| act aca aaa ctt gat ttc act atc aat gga gac aaa aga acg ggg ggc<br>Thr Thr Lys Leu Asp Phe Thr Ile Asn Gly Asp Lys Arg Thr Gly Gly<br>185                  190                  195 | 978 |
| aaa cca aat aca cct gaa aag ttc cca tgg agt gat ggg aaa tat att<br>Lys Pro Asn Thr Pro Glu Lys Phe Pro Trp Ser Asp Gly Lys Tyr Ile<br>200                  205                  210 | 1026 |
| cac acc caa tgg att aac aca ata gta aca cca aca gaa aca aat atc<br>His Thr Gln Trp Ile Asn Thr Ile Val Thr Pro Thr Glu Thr Asn Ile<br>215                  220                  225                  230 | 1074 |
| aac aca gaa aat aac gct caa gag ctt tta aaa caa gcg agc atc att<br>Asn Thr Glu Asn Asn Ala Gln Glu Leu Leu Lys Gln Ala Ser Ile Ile<br>                  235                  240                  245 | 1122 |
| atc act acc cta aat gag gca tgc cca aac ttc caa aat ggt ggt aga<br>Ile Thr Thr Leu Asn Glu Ala Cys Pro Asn Phe Gln Asn Gly Gly Arg<br>250                  255                  260 | 1170 |
| agt tat tgg caa ggg ata agc ggc aat ggg aca atg tgc ggg atg ttt<br>Ser Tyr Trp Gln Gly Ile Ser Gly Asn Gly Thr Met Cys Gly Met Phe<br>265                  270                  275 | 1218 |
| aag aat gaa atc agc gcg atc caa ggc atg atc gct aac gct caa gaa<br>Lys Asn Glu Ile Ser Ala Ile Gln Gly Met Ile Ala Asn Ala Gln Glu<br>280                  285                  290 | 1266 |
| gct gtc gcg caa agc aaa atc gtt agt gaa aac gcg caa aat caa aac<br>Ala Val Ala Gln Ser Lys Ile Val Ser Glu Asn Ala Gln Asn Gln Asn<br>295                  300                  305                  310 | 1314 |
| aac ttg gat act gga aaa cca ttc aac cct tac acg gac gcc agc ttt<br>Asn Leu Asp Thr Gly Lys Pro Phe Asn Pro Tyr Thr Asp Ala Ser Phe<br>                  315                  320                  325 | 1362 |
| gcg caa agc atg ctc aaa aac gct caa gcg caa gca gag att tta aac<br>Ala Gln Ser Met Leu Lys Asn Ala Gln Ala Gln Ala Glu Ile Leu Asn<br>330                  335                  340 | 1410 |
| caa gcc gaa caa gta gta aaa aac ttt gaa aaa atc cct aca gcc ttt<br>Gln Ala Glu Gln Val Val Lys Asn Phe Glu Lys Ile Pro Thr Ala Phe<br>345                  350                  355 | 1458 |
| gta tca gac tct tta ggg gtg tgt tat gaa gtg caa ggg ggt gag cgt<br>Val Ser Asp Ser Leu Gly Val Cys Tyr Glu Val Gln Gly Gly Glu Arg | 1506 |

-continued

```
            360                       365                       370
agg ggc acc aat cca ggt cag gta act tct aac act tgg gga gcc ggt     1554
Arg Gly Thr Asn Pro Gly Gln Val Thr Ser Asn Thr Trp Gly Ala Gly
375                 380                     385                 390 tgc gcg tat gtg aaa caa acc ata acg aat tta gac aac agc atc gct     1602
Cys Ala Tyr Val Lys Gln Thr Ile Thr Asn Leu Asp Asn Ser Ile Ala
                        395                 400                 405 cac ttt ggc act caa gag cag cag ata cag caa gcc gaa aac atc gct     1650
His Phe Gly Thr Gln Glu Gln Gln Ile Gln Gln Ala Glu Asn Ile Ala
            410                     415                 420 gac act cta gtg aat ttc aaa tct aga tac agc gaa tta ggc aac acc     1698
Asp Thr Leu Val Asn Phe Lys Ser Arg Tyr Ser Glu Leu Gly Asn Thr
        425                     430                 435 tat aac agc atc acc acc gcg ctc tcc aaa gtc cct aac gcg caa agc     1746
Tyr Asn Ser Ile Thr Thr Ala Leu Ser Lys Val Pro Asn Ala Gln Ser
    440                     445                 450 ttg caa aac gtg gtg agc aaa aag aat aac ccc tat agc cct caa ggc     1794
Leu Gln Asn Val Val Ser Lys Lys Asn Asn Pro Tyr Ser Pro Gln Gly
455                     460                 465                 470 ata gag acc aat tac tac ctc aat caa aat tct tac aac caa atc caa     1842
Ile Glu Thr Asn Tyr Tyr Leu Asn Gln Asn Ser Tyr Asn Gln Ile Gln
                475                     480                 485 acc atc aac caa gaa cta ggg cgt aac ccc ttt agg aaa gtg ggc atc     1890
Thr Ile Asn Gln Glu Leu Gly Arg Asn Pro Phe Arg Lys Val Gly Ile
            490                     495                 500 gtc aat tct caa acc aac aat ggt gcc atg aat ggg atc ggt att cag     1938
Val Asn Ser Gln Thr Asn Asn Gly Ala Met Asn Gly Ile Gly Ile Gln
        505                     510                 515 gtg ggc tat aag caa ttc ttt ggc caa aaa aga aaa tgg ggc gct agg     1986
Val Gly Tyr Lys Gln Phe Phe Gly Gln Lys Arg Lys Trp Gly Ala Arg
    520                     525                 530 tat tac ggc ttt ttt gac tac aac cat gcg ttc att aaa tcc agc ttc     2034
Tyr Tyr Gly Phe Phe Asp Tyr Asn His Ala Phe Ile Lys Ser Ser Phe
535                     540                 545                 550 ttc aac tcg gct tct gat gtg tgg act tat ggt ttt gga gcg gac gct     2082
Phe Asn Ser Ala Ser Asp Val Trp Thr Tyr Gly Phe Gly Ala Asp Ala
                555                     560                 565 ctt tat aac ttc atc aac gat aaa gcc acc aat ttc tta ggc aaa aac     2130
Leu Tyr Asn Phe Ile Asn Asp Lys Ala Thr Asn Phe Leu Gly Lys Asn
            570                     575                 580 aac aag ctt tcc gtg ggg ctt ttt gga ggg att gcg tta gcg ggc act     2178
Asn Lys Leu Ser Val Gly Leu Phe Gly Gly Ile Ala Leu Ala Gly Thr
        585                     590                 595 tca tgg ctt aat tct gag tat gtg aat tta gcc acc gtg aat aac gtc     2226
Ser Trp Leu Asn Ser Glu Tyr Val Asn Leu Ala Thr Val Asn Asn Val
    600                     605                 610 tat aac gct aaa atg aat gtg gcg aat ttc caa ttc tta ttc aat atg     2274
Tyr Asn Ala Lys Met Asn Val Ala Asn Phe Gln Phe Leu Phe Asn Met
615                     620                 625                 630 gga gtg agg atg aat tta gcc aga tcc aag aaa aaa ggc agc gat cat     2322
Gly Val Arg Met Asn Leu Ala Arg Ser Lys Lys Lys Gly Ser Asp His
                635                     640                 645 gcg gct cag cat ggg att gaa cta ggg ctt aaa atc ccc acc atc aac     2370
Ala Ala Gln His Gly Ile Glu Leu Gly Leu Lys Ile Pro Thr Ile Asn
            650                     655                 660 acg aac tat tat tct ttc atg ggg gct gaa ctc aaa tac aga agg ctt     2418
Thr Asn Tyr Tyr Ser Phe Met Gly Ala Glu Leu Lys Tyr Arg Arg Leu
        665                     670                 675 tat agc gtg tat ttg aat tat gtg ttc gct tac taagcttttt gtgaaactcc   2471
```

```
Tyr Ser Val Tyr Leu Asn Tyr Val Phe Ala Tyr
    680                 685 cttttttaagg ggtttttttt tgaactctct ttttaaattc tcttttttaaa gagatttctt    2531 tttttttaagc tttttttttga attcttttttt ttgaattctt tgttttttaag cttttttttaa   2591 acccttttcgt ttttaaactc ccttttttaa gggattttctt ttttttaaact ctttttttttt   2651 aaactctttt ttttaaaccc tctttttttta agggattttct ttttaaagct tttttgaagt    2711 cttttttttaa attctttttt tgggggtttg atctttcttt ttgccaatcc ccactacttt    2771 cgcttttttaa tctttaggtt ttatttt                                        2798
```

<210> SEQ ID NO 2
<211> LENGTH: 708
<212> TYPE: PRT
<213> ORGANISM: Helicobacter pylori
<220> FEATURE:
<221> NAME/KEY: SIGNAL
<222> LOCATION: (1)...(19)

<400> SEQUENCE: 2

```
Met Lys Lys Thr Leu Leu Leu Ser Leu Ser Leu Ser Phe Leu
            -15             -10             -5

Leu His Ala Glu Asp Asp Gly Phe Tyr Thr Ser Val Gly Tyr Gln Ile
             1               5              10

Gly Glu Ala Ala Gln Met Val Lys Asn Thr Lys Gly Ile Gln Glu Leu
    15              20              25

Ser Asp Asn Tyr Glu Lys Leu Asn Asn Leu Leu Asn Asn Tyr Ser Thr
30              35              40              45

Leu Asn Thr Leu Ile Lys Leu Ser Ala Asp Pro Ser Ala Ile Asn Asp
                50              55              60

Ala Arg Asp Asn Leu Gly Ser Ser Arg Asn Leu Leu Asp Val Lys
            65              70              75

Thr Asn Ser Pro Ala Tyr Gln Ala Val Leu Leu Ala Leu Asn Ala Ala
            80              85              90

Val Gly Leu Trp Gln Val Thr Ser Tyr Ala Phe Thr Ala Cys Gly Pro
    95              100             105

Gly Ser Asn Glu Asn Ala Asn Gly Gly Ile Gln Thr Phe Asn Asn Val
110             115             120             125

Pro Gly Gln Asp Thr Thr Thr Ile Thr Cys Asn Ser Tyr Tyr Glu Pro
            130             135             140

Gly His Gly Gly Pro Ile Ser Thr Ala Asn Tyr Ala Lys Ile Asn Gln
            145             150             155

Ala Tyr Gln Ile Ile Gln Lys Ala Leu Thr Ala Asn Gly Ala Asn Gly
            160             165             170

Asp Gly Val Pro Val Leu Ser Asn Thr Thr Lys Leu Asp Phe Thr
    175             180             185

Ile Asn Gly Asp Lys Arg Thr Gly Gly Lys Pro Asn Thr Pro Glu Lys
190             195             200             205

Phe Pro Trp Ser Asp Gly Lys Tyr Ile His Thr Gln Trp Ile Asn Thr
            210             215             220

Ile Val Thr Pro Thr Glu Thr Asn Ile Asn Thr Glu Asn Asn Ala Gln
            225             230             235

Glu Leu Leu Lys Gln Ala Ser Ile Ile Thr Thr Leu Asn Glu Ala
            240             245             250

Cys Pro Asn Phe Gln Asn Gly Gly Arg Ser Tyr Trp Gln Gly Ile Ser
    255             260             265
```

-continued

```
Gly Asn Gly Thr Met Cys Gly Met Phe Lys Asn Glu Ile Ser Ala Ile
270                 275                 280                 285

Gln Gly Met Ile Ala Asn Ala Gln Glu Ala Val Ala Gln Ser Lys Ile
                290                 295                 300

Val Ser Glu Asn Ala Gln Asn Gln Asn Asn Leu Asp Thr Gly Lys Pro
            305                 310                 315

Phe Asn Pro Tyr Thr Asp Ala Ser Phe Ala Gln Ser Met Leu Lys Asn
        320                 325                 330

Ala Gln Ala Gln Ala Glu Ile Leu Asn Gln Ala Glu Gln Val Val Lys
335                 340                 345

Asn Phe Glu Lys Ile Pro Thr Ala Phe Val Ser Asp Ser Leu Gly Val
350                 355                 360                 365

Cys Tyr Glu Val Gln Gly Gly Glu Arg Arg Gly Thr Asn Pro Gly Gln
                370                 375                 380

Val Thr Ser Asn Thr Trp Gly Ala Gly Cys Ala Tyr Val Lys Gln Thr
            385                 390                 395

Ile Thr Asn Leu Asp Asn Ser Ile Ala His Phe Gly Thr Gln Glu Gln
        400                 405                 410

Gln Ile Gln Gln Ala Glu Asn Ile Ala Asp Thr Leu Val Asn Phe Lys
415                 420                 425

Ser Arg Tyr Ser Glu Leu Gly Asn Thr Tyr Asn Ser Ile Thr Thr Ala
430                 435                 440                 445

Leu Ser Lys Val Pro Asn Ala Gln Ser Leu Gln Asn Val Val Ser Lys
                450                 455                 460

Lys Asn Asn Pro Tyr Ser Pro Gln Gly Ile Glu Thr Asn Tyr Tyr Leu
            465                 470                 475

Asn Gln Asn Ser Tyr Asn Gln Ile Gln Thr Ile Asn Gln Glu Leu Gly
        480                 485                 490

Arg Asn Pro Phe Arg Lys Val Gly Ile Val Asn Ser Gln Thr Asn Asn
        495                 500                 505

Gly Ala Met Asn Gly Ile Gly Ile Gln Val Gly Tyr Lys Gln Phe Phe
510                 515                 520                 525

Gly Gln Lys Arg Lys Trp Gly Ala Arg Tyr Tyr Gly Phe Phe Asp Tyr
                530                 535                 540

Asn His Ala Phe Ile Lys Ser Ser Phe Phe Asn Ser Ala Ser Asp Val
            545                 550                 555

Trp Thr Tyr Gly Phe Gly Ala Asp Ala Leu Tyr Asn Phe Ile Asn Asp
        560                 565                 570

Lys Ala Thr Asn Phe Leu Gly Lys Asn Lys Leu Ser Val Gly Leu
575                 580                 585

Phe Gly Gly Ile Ala Leu Ala Gly Thr Ser Trp Leu Asn Ser Glu Tyr
590                 595                 600                 605

Val Asn Leu Ala Thr Val Asn Asn Val Tyr Asn Ala Lys Met Asn Val
                610                 615                 620

Ala Asn Phe Gln Phe Leu Phe Asn Met Gly Val Arg Met Asn Leu Ala
            625                 630                 635

Arg Ser Lys Lys Lys Gly Ser Asp His Ala Ala Gln His Gly Ile Glu
        640                 645                 650

Leu Gly Leu Lys Ile Pro Thr Ile Asn Thr Asn Tyr Tyr Ser Phe Met
655                 660                 665

Gly Ala Glu Leu Lys Tyr Arg Arg Leu Tyr Ser Val Tyr Leu Asn Tyr
670                 675                 680                 685
```

-continued

```
Val Phe Ala Tyr

<210> SEQ ID NO 3
<211> LENGTH: 2699
<212> TYPE: DNA
<213> ORGANISM: Helicobacter pylori
<220> FEATURE:
<221> NAME/KEY: CDS
<222> LOCATION: (199)...(2397)
<220> FEATURE:
<221> NAME/KEY: sig_peptide
<222> LOCATION: (199)...(259)

<400> SEQUENCE: 3
taaaatccaa ttaaaagcgt tcaaaggtaa cgcaaaaaaa caaaaaatga cgcaattttt      60
tcaaaatgac aaaaaaaaac gctttatgct ataataccccc aaatacattc taatagcaaa   120
tgcgttctaa tgcaaatgca ttccaatgta tgaaatccct aatactaaat ccaatttaat   180
ccaaaaagga gaaaaaac atg aaa aaa cac atc ctt tca tta gct tta ggc      231
                   Met Lys Lys His Ile Leu Ser Leu Ala Leu Gly
                   -20             -15                 -10 tcg ctt tta gtt tcc act ttg agc gct gaa gac gac ggc ttt tac aca      279
Ser Leu Leu Val Ser Thr Leu Ser Ala Glu Asp Asp Gly Phe Tyr Thr
                -5              1               5 agc gta ggc tat cag atc ggt gaa gcc gct caa atg gta aca aac acc      327
Ser Val Gly Tyr Gln Ile Gly Glu Ala Ala Gln Met Val Thr Asn Thr
         10              15              20 aaa ggc atc caa cag ctt tca gac aat tat gaa aat ttg aac aac ctt      375
Lys Gly Ile Gln Gln Leu Ser Asp Asn Tyr Glu Asn Leu Asn Asn Leu
 25              30              35 tta acg aga tac agc acc cta aac acc ctt atc aaa ttg tcc gct gat      423
Leu Thr Arg Tyr Ser Thr Leu Asn Thr Leu Ile Lys Leu Ser Ala Asp
 40              45              50              55 ccg agc gca att aat gcg gtg cgg gaa aat ctg ggc gcg agc gcg aag      471
Pro Ser Ala Ile Asn Ala Val Arg Glu Asn Leu Gly Ala Ser Ala Lys
             60              65              70 aat ttg atc ggc gat aaa gcc aac tcc ccc gcc tat caa gcc gtg ctt      519
Asn Leu Ile Gly Asp Lys Ala Asn Ser Pro Ala Tyr Gln Ala Val Leu
             75              80              85 tta gcg atc aac gcg gcg gta ggg ttt tgg aat gtc gtg ggc tat gtg      567
Leu Ala Ile Asn Ala Ala Val Gly Phe Trp Asn Val Val Gly Tyr Val
         90              95             100 acg caa tgt ggg ggt aac gcc aat ggt caa gaa agc acc tct tca acc      615
Thr Gln Cys Gly Gly Asn Ala Asn Gly Gln Glu Ser Thr Ser Ser Thr
     105             110             115 acc atc ttc aac aac gag cca ggg tat cga tcc act tcc atc act tgt      663
Thr Ile Phe Asn Asn Glu Pro Gly Tyr Arg Ser Thr Ser Ile Thr Cys
120             125             130             135 tct ttg aac ggg cat aag cct gga tac tat ggc cct atg agc att gag      711
Ser Leu Asn Gly His Lys Pro Gly Tyr Tyr Gly Pro Met Ser Ile Glu
             140             145             150 aat ttt aaa aag ctt aac gaa gcc tat cag atc ctc caa acg gct tta      759
Asn Phe Lys Lys Leu Asn Glu Ala Tyr Gln Ile Leu Gln Thr Ala Leu
         155             160             165 aaa aac ggc tta ccc gcg ctc aaa gaa aac aac ggg aag gtc agt gta      807
Lys Asn Gly Leu Pro Ala Leu Lys Glu Asn Asn Gly Lys Val Ser Val
     170             175             180 acc tat acc tac aca tgc tca ggg caa ggg aat aat aac tgc tcg cca      855
Thr Tyr Thr Tyr Thr Cys Ser Gly Gln Gly Asn Asn Asn Cys Ser Pro
 185             190             195 agt gtc aac gga acc aaa acc aca acc caa acc ata gac ggc aaa agc      903
```

```
Ser Val Asn Gly Thr Lys Thr Thr Thr Gln Thr Ile Asp Gly Lys Ser
200                 205                 210                 215 gta acc acc acg atc agt tca aaa gtg gtt ggt agc atc gct agt ggc    951
Val Thr Thr Thr Ile Ser Ser Lys Val Val Gly Ser Ile Ala Ser Gly
                    220                 225                 230 aac aca tca cat gtc atc acc aac aaa tta gac ggt gtg cct gat agc    999
Asn Thr Ser His Val Ile Thr Asn Lys Leu Asp Gly Val Pro Asp Ser
                235                 240                 245 gct caa gcg ctc tta gcg caa gcg agc acg ctc atc aac acc atc aac    1047
Ala Gln Ala Leu Leu Ala Gln Ala Ser Thr Leu Ile Asn Thr Ile Asn
            250                 255                 260 gaa gca tgc ccg tat ttc cat gct act aat agt agt gag gct aac gcc    1095
Glu Ala Cys Pro Tyr Phe His Ala Thr Asn Ser Ser Glu Ala Asn Ala
        265                 270                 275 cca aaa ttc tct act act act ggg aaa ata tgc ggc gct ttt tca gaa    1143
Pro Lys Phe Ser Thr Thr Thr Gly Lys Ile Cys Gly Ala Phe Ser Glu
280                 285                 290                 295 gaa atc agc gcg atc caa aag atg atc acg gac gcg caa gag cta gtt    1191
Glu Ile Ser Ala Ile Gln Lys Met Ile Thr Asp Ala Gln Glu Leu Val
                    300                 305                 310 aat caa acg agc gtc att aac agc aac gaa caa tca act ccg gta ggc    1239
Asn Gln Thr Ser Val Ile Asn Ser Asn Glu Gln Ser Thr Pro Val Gly
                315                 320                 325 aat aat aat ggc aag cct ttc aac cct ttc acg gac gca agt ttt gcg    1287
Asn Asn Asn Gly Lys Pro Phe Asn Pro Phe Thr Asp Ala Ser Phe Ala
            330                 335                 340 caa ggc atg ctc gct aac gct agc gcg caa gct aaa atg ctc aat tta    1335
Gln Gly Met Leu Ala Asn Ala Ser Ala Gln Ala Lys Met Leu Asn Leu
        345                 350                 355 gcc cat cag gtg ggg caa gcc att aac cca gag aat ctt agc gag aat    1383
Ala His Gln Val Gly Gln Ala Ile Asn Pro Glu Asn Leu Ser Glu Asn
360                 365                 370                 375 ttt aaa aat ttt gtt aca ggc ttt tta gcc aca tgc aat aac aaa tca    1431
Phe Lys Asn Phe Val Thr Gly Phe Leu Ala Thr Cys Asn Asn Lys Ser
                    380                 385                 390 aca gct ggc act ggt ggc aca caa ggt tca gct cca ggc aca gtg acc    1479
Thr Ala Gly Thr Gly Gly Thr Gln Gly Ser Ala Pro Gly Thr Val Thr
                395                 400                 405 act caa act ttc gct tct ggt tgc gcg tat gtg gag caa acc cta acg    1527
Thr Gln Thr Phe Ala Ser Gly Cys Ala Tyr Val Glu Gln Thr Leu Thr
            410                 415                 420 aac tta ggc aac agc atc gct cac ttt ggc act caa gag cag cag ata    1575
Asn Leu Gly Asn Ser Ile Ala His Phe Gly Thr Gln Glu Gln Gln Ile
        425                 430                 435 cag caa gcc gaa aac atc gct gac act cta gtg aat ttc aaa tct aga    1623
Gln Gln Ala Glu Asn Ile Ala Asp Thr Leu Val Asn Phe Lys Ser Arg
440                 445                 450                 455 tac agc gaa tta ggc aac acc tat aac agc atc acc acc gcg ctc tcc    1671
Tyr Ser Glu Leu Gly Asn Thr Tyr Asn Ser Ile Thr Thr Ala Leu Ser
                    460                 465                 470 aaa gtc cct aac gcg caa agc ttg caa aac gtg gtg agc aaa aag aat    1719
Lys Val Pro Asn Ala Gln Ser Leu Gln Asn Val Val Ser Lys Lys Asn
                475                 480                 485 aac ccc tat agc cct caa ggc ata gag acc aat tac tac ctc aat caa    1767
Asn Pro Tyr Ser Pro Gln Gly Ile Glu Thr Asn Tyr Tyr Leu Asn Gln
            490                 495                 500 aat tct tac aac caa atc caa acc atc aac caa gaa cta ggg cgt aac    1815
Asn Ser Tyr Asn Gln Ile Gln Thr Ile Asn Gln Glu Leu Gly Arg Asn
        505                 510                 515
```

-continued

| | | |
|---|---|---|
| ccc ttt agg aaa gtg ggc atc gtc aat tct caa acc aac aat ggt gcc<br>Pro Phe Arg Lys Val Gly Ile Val Asn Ser Gln Thr Asn Asn Gly Ala<br>520                        525                      530                      535 | 1863 |
| atg aat ggg atc ggt att cag gtg ggc tat aag caa ttc ttt ggc caa<br>Met Asn Gly Ile Gly Ile Gln Val Gly Tyr Lys Gln Phe Phe Gly Gln<br>                  540                      545                      550 | 1911 |
| aaa aga aaa tgg ggc gct agg tat tac ggc ttt ttt gat tac aac cat<br>Lys Arg Lys Trp Gly Ala Arg Tyr Tyr Gly Phe Phe Asp Tyr Asn His<br>              555                      560                      565 | 1959 |
| gcg ttc atc aaa tcc agc ttt ttc aac tcg gct tct gac gtg tgg act<br>Ala Phe Ile Lys Ser Ser Phe Phe Asn Ser Ala Ser Asp Val Trp Thr<br>570                        575                      580 | 2007 |
| tat ggt ttt gga gcg gac gcg ctt tat aac ttc atc aac gat aaa gcc<br>Tyr Gly Phe Gly Ala Asp Ala Leu Tyr Asn Phe Ile Asn Asp Lys Ala<br>              585                      590                      595 | 2055 |
| acc aat ttc tta ggc aaa aac aac aag ctt tct ttg ggg ctt ttt ggc<br>Thr Asn Phe Leu Gly Lys Asn Asn Lys Leu Ser Leu Gly Leu Phe Gly<br>600                        605                      610                      615 | 2103 |
| ggg att gcg tta gcg ggc act tca tgg ctc aat tct gag tac gtg aat<br>Gly Ile Ala Leu Ala Gly Thr Ser Trp Leu Asn Ser Glu Tyr Val Asn<br>                    620                      625                      630 | 2151 |
| tta gcc acc gtg aat aac gtc tat aac gct aaa atg aat gtg gcg aat<br>Leu Ala Thr Val Asn Asn Val Tyr Asn Ala Lys Met Asn Val Ala Asn<br>635                        640                      645 | 2199 |
| ttc caa ttc tta ttc aat atg gga gtg agg atg aat tta gcc aga tcc<br>Phe Gln Phe Leu Phe Asn Met Gly Val Arg Met Asn Leu Ala Arg Ser<br>              650                      655                      660 | 2247 |
| aag aaa aaa ggc agc gat cat gca gct cag cat ggg att gag tta ggg<br>Lys Lys Lys Gly Ser Asp His Ala Ala Gln His Gly Ile Glu Leu Gly<br>665                        670                      675 | 2295 |
| ctt aaa atc ccc acc atc aac acg aac tat tat tcc ttt atg ggg gct<br>Leu Lys Ile Pro Thr Ile Asn Thr Asn Tyr Tyr Ser Phe Met Gly Ala<br>680                        685                      690                      695 | 2343 |
| gaa ctc aaa tac aga agg ctc tat agc gtg tat ttg aac tat gtg ttc<br>Glu Leu Lys Tyr Arg Arg Leu Tyr Ser Val Tyr Leu Asn Tyr Val Phe<br>                    700                      705                      710 | 2391 |
| gct tac taatgtttgg ctctttgtga aactcccttt ttaaggggtt ttttttgaa<br>Ala Tyr | 2447 |
| ctctcttttt aaattctctt tttaaagaga tttctttttt ttaagctttt ttttgaattc | 2507 |
| tttttttttg aattctttgt ttttaagctt tttttaaacc ctttcgtttt taaactccct | 2567 |
| tttttaaggg atttcttttt ttgaactccc ttttttgaac ccttttttttt aaaccctctt | 2627 |
| tttttaaggg gtttcttttt aaagcttttt tgaagtcttt ttttaaattc ttttttgggg | 2687 |
| ggtttgatct tt | 2699 |

<210> SEQ ID NO 4
<211> LENGTH: 733
<212> TYPE: PRT
<213> ORGANISM: Helicobacter pylori
<220> FEATURE:
<221> NAME/KEY: SIGNAL
<222> LOCATION: (1)...(20)

<400> SEQUENCE: 4

Met Lys Lys His Ile Leu Ser Leu Ala Leu Gly Ser Leu Leu Val Ser
-20                        -15                        -10                        -5

Thr Leu Ser Ala Glu Asp Asp Gly Phe Tyr Thr Ser Val Gly Tyr Gln
                  1                      5                            10

Ile Gly Glu Ala Ala Gln Met Val Thr Asn Thr Lys Gly Ile Gln Gln

-continued

```
            15                  20                  25
Leu Ser Asp Asn Tyr Glu Asn Leu Asn Asn Leu Leu Thr Arg Tyr Ser
    30                  35                  40

Thr Leu Asn Thr Leu Ile Lys Leu Ser Ala Asp Pro Ser Ala Ile Asn
45                  50                  55                  60

Ala Val Arg Glu Asn Leu Gly Ala Ser Ala Lys Asn Leu Ile Gly Asp
                65                  70                  75

Lys Ala Asn Ser Pro Ala Tyr Gln Ala Val Leu Leu Ala Ile Asn Ala
            80                  85                  90

Ala Val Gly Phe Trp Asn Val Gly Tyr Val Thr Gln Cys Gly Gly
                95                  100                 105

Asn Ala Asn Gly Gln Glu Ser Thr Ser Ser Thr Thr Ile Phe Asn Asn
    110                 115                 120

Glu Pro Gly Tyr Arg Ser Thr Ser Ile Thr Cys Ser Leu Asn Gly His
125                 130                 135                 140

Lys Pro Gly Tyr Tyr Gly Pro Met Ser Ile Glu Asn Phe Lys Lys Leu
                145                 150                 155

Asn Glu Ala Tyr Gln Ile Leu Gln Thr Ala Leu Lys Asn Gly Leu Pro
            160                 165                 170

Ala Leu Lys Glu Asn Asn Gly Lys Val Ser Val Thr Tyr Thr Tyr Thr
    175                 180                 185

Cys Ser Gly Gln Gly Asn Asn Asn Cys Ser Pro Ser Val Asn Gly Thr
    190                 195                 200

Lys Thr Thr Thr Gln Thr Ile Asp Gly Lys Ser Val Thr Thr Thr Ile
205                 210                 215                 220

Ser Ser Lys Val Val Gly Ser Ile Ala Ser Gly Asn Thr Ser His Val
                225                 230                 235

Ile Thr Asn Lys Leu Asp Gly Val Pro Asp Ser Ala Gln Ala Leu Leu
            240                 245                 250

Ala Gln Ala Ser Thr Leu Ile Asn Thr Ile Asn Glu Ala Cys Pro Tyr
    255                 260                 265

Phe His Ala Thr Asn Ser Ser Glu Ala Asn Ala Pro Lys Phe Ser Thr
    270                 275                 280

Thr Thr Gly Lys Ile Cys Gly Ala Phe Ser Glu Glu Ile Ser Ala Ile
285                 290                 295                 300

Gln Lys Met Ile Thr Asp Ala Gln Glu Leu Val Asn Gln Thr Ser Val
                305                 310                 315

Ile Asn Ser Asn Glu Gln Ser Thr Pro Val Gly Asn Asn Gly Lys
            320                 325                 330

Pro Phe Asn Pro Phe Thr Asp Ala Ser Phe Ala Gln Gly Met Leu Ala
    335                 340                 345

Asn Ala Ser Ala Gln Ala Lys Met Leu Asn Leu Ala His Gln Val Gly
    350                 355                 360

Gln Ala Ile Asn Pro Glu Asn Leu Ser Glu Asn Phe Lys Asn Phe Val
365                 370                 375                 380

Thr Gly Phe Leu Ala Thr Cys Asn Asn Lys Ser Thr Ala Gly Thr Gly
                385                 390                 395

Gly Thr Gln Gly Ser Ala Pro Gly Thr Val Thr Thr Gln Thr Phe Ala
            400                 405                 410

Ser Gly Cys Ala Tyr Val Glu Gln Thr Leu Thr Asn Leu Gly Asn Ser
            415                 420                 425

Ile Ala His Phe Gly Thr Gln Glu Gln Gln Ile Gln Gln Ala Glu Asn
    430                 435                 440
```

Ile Ala Asp Thr Leu Val Asn Phe Lys Ser Arg Tyr Ser Glu Leu Gly
445                 450                 455                 460

Asn Thr Tyr Asn Ser Ile Thr Thr Ala Leu Ser Lys Val Pro Asn Ala
            465                 470                 475

Gln Ser Leu Gln Asn Val Val Ser Lys Lys Asn Asn Pro Tyr Ser Pro
                480                 485                 490

Gln Gly Ile Glu Thr Asn Tyr Tyr Leu Asn Gln Asn Ser Tyr Asn Gln
            495                 500                 505

Ile Gln Thr Ile Asn Gln Glu Leu Gly Arg Asn Pro Phe Arg Lys Val
    510                 515                 520

Gly Ile Val Asn Ser Gln Thr Asn Asn Gly Ala Met Asn Gly Ile Gly
525                 530                 535                 540

Ile Gln Val Gly Tyr Lys Gln Phe Phe Gly Gln Lys Arg Lys Trp Gly
                545                 550                 555

Ala Arg Tyr Tyr Gly Phe Phe Asp Tyr Asn His Ala Phe Ile Lys Ser
                560                 565                 570

Ser Phe Phe Asn Ser Ala Ser Asp Val Trp Thr Tyr Gly Phe Gly Ala
                575                 580                 585

Asp Ala Leu Tyr Asn Phe Ile Asn Asp Lys Ala Thr Asn Phe Leu Gly
590                 595                 600

Lys Asn Asn Lys Leu Ser Leu Gly Leu Phe Gly Ile Ala Leu Ala
605                 610                 615                 620

Gly Thr Ser Trp Leu Asn Ser Glu Tyr Val Asn Leu Ala Thr Val Asn
                625                 630                 635

Asn Val Tyr Asn Ala Lys Met Asn Val Ala Asn Phe Gln Phe Leu Phe
            640                 645                 650

Asn Met Gly Val Arg Met Asn Leu Ala Arg Ser Lys Lys Lys Gly Ser
            655                 660                 665

Asp His Ala Ala Gln His Gly Ile Glu Leu Gly Leu Lys Ile Pro Thr
    670                 675                 680

Ile Asn Thr Asn Tyr Tyr Ser Phe Met Gly Ala Glu Leu Lys Tyr Arg
685                 690                 695                 700

Arg Leu Tyr Ser Val Tyr Leu Asn Tyr Val Phe Ala Tyr
                705                 710

<210> SEQ ID NO 5
<211> LENGTH: 2915
<212> TYPE: DNA
<213> ORGANISM: Helicobacter pylori
<220> FEATURE:
<221> NAME/KEY: CDS
<222> LOCATION: (365)...(2599)
<220> FEATURE:
<221> NAME/KEY: sig_peptide
<222> LOCATION: (365)...(425)
<220> FEATURE:
<221> NAME/KEY: misc_feature
<222> LOCATION: 2585
<223> OTHER INFORMATION: n = A,T,C or G

<400> SEQUENCE: 5
ttttaggcga caaaatcgct tatgttgggg ataaaggcaa cccgcacaat ttcgctcaca      60
agaaataaac cgctcataag gggcaaacgc cccaaaaaag cgattttta agaggttacg     120 gcaaatcaa gctctttagt atttaatctt aaaaaatgct aaaagccttt ttatgggcta     180
acaccacaca aaagcatca aatcaaaaa aatgacaaaa ttttaagaa aatgacaaaa      240 aaaacgctt tatgctataa taccccaaat acattctaat agcaaatgcg ttctaatgca     300

-continued

```
aatgcattcc aatgtatgaa atccctaata ctaaatccaa tttaatccaa aaaggagaaa        360 aaac atg aaa aaa cac atc ctt tca tta gct tta ggc tcg ctt tta gtt        409
     Met Lys Lys His Ile Leu Ser Leu Ala Leu Gly Ser Leu Leu Val
         -20             -15             -10 tcc act ttg agc gct gaa gac gac ggc ttt tac aca agc gta ggc tat        457
Ser Thr Leu Ser Ala Glu Asp Asp Gly Phe Tyr Thr Ser Val Gly Tyr
-5                   1               5                   10 cag atc ggt gaa gcc gct caa atg gta aca aac acc aaa ggc atc caa        505
Gln Ile Gly Glu Ala Ala Gln Met Val Thr Asn Thr Lys Gly Ile Gln
            15                  20                  25 cag ctt tca gac aat tat gaa aat ttg aac aac ctt tta acg aga tac        553
Gln Leu Ser Asp Asn Tyr Glu Asn Leu Asn Asn Leu Leu Thr Arg Tyr
        30                  35                  40 agc acc cta aac acc ctt atc aaa ttg tcc gct gat ccg agc gca att        601
Ser Thr Leu Asn Thr Leu Ile Lys Leu Ser Ala Asp Pro Ser Ala Ile
    45                  50                  55 aat gcg gtg cgg gaa aat ctg ggc gcg agc acg aag aat ttg atc ggc        649
Asn Ala Val Arg Glu Asn Leu Gly Ala Ser Thr Lys Asn Leu Ile Gly
60                  65                  70                  75 gat aaa gcc aac tcc ccg gcg tat caa gcc gtg ttt tta gcg atc aac        697
Asp Lys Ala Asn Ser Pro Ala Tyr Gln Ala Val Phe Leu Ala Ile Asn
                80                  85                  90 gcg gcg gta ggg ttg tgg aat acc atc ggc tat gcg gtc atg tgc ggg        745
Ala Ala Val Gly Leu Trp Asn Thr Ile Gly Tyr Ala Val Met Cys Gly
            95                  100                 105 aac ggg aac ggc aca gag agt ggg cct ggc agc gtg atc ttt aat gac        793
Asn Gly Asn Gly Thr Glu Ser Gly Pro Gly Ser Val Ile Phe Asn Asp
        110                 115                 120 caa cca gga cag gat tcc acg caa att act tgc aac cgc ttt gaa tca        841
Gln Pro Gly Gln Asp Ser Thr Gln Ile Thr Cys Asn Arg Phe Glu Ser
    125                 130                 135 act ggg cct ggt aaa agc atg tct att gat gaa ttc aaa aaa ctc aat        889
Thr Gly Pro Gly Lys Ser Met Ser Ile Asp Glu Phe Lys Lys Leu Asn
140                 145                 150                 155 gaa gcc tat caa atc atc cag caa gct tta aaa aat caa agt ggg ttt        937
Glu Ala Tyr Gln Ile Ile Gln Gln Ala Leu Lys Asn Gln Ser Gly Phe
                160                 165                 170 cct gaa tta ggc ggg aac ggc aca aaa gtg agt gtt aat tac aat tac        985
Pro Glu Leu Gly Gly Asn Gly Thr Lys Val Ser Val Asn Tyr Asn Tyr
            175                 180                 185 gaa tgc aga caa act gct gat atc aac ggc ggt gtg tat cag ttc tgc       1033
Glu Cys Arg Gln Thr Ala Asp Ile Asn Gly Gly Val Tyr Gln Phe Cys
        190                 195                 200 aag gct aaa aat ggt agt agt agc agt agt aat ggc ggt aat ggc agt       1081
Lys Ala Lys Asn Gly Ser Ser Ser Ser Ser Asn Gly Gly Asn Gly Ser
    205                 210                 215 agc acg caa aca acc gcg aca acc acg caa gac ggc gta acg atc acc       1129
Ser Thr Gln Thr Thr Ala Thr Thr Thr Gln Asp Gly Val Thr Ile Thr
220                 225                 230                 235 act acc tat aat aat aac aaa gcc acc gtc aaa ttt gac atc acc aat       1177
Thr Thr Tyr Asn Asn Asn Lys Ala Thr Val Lys Phe Asp Ile Thr Asn
                240                 245                 250 aac gct gaa cag ctg tta aat caa gcg gca aac atc atg caa gtc ctt       1225
Asn Ala Glu Gln Leu Leu Asn Gln Ala Ala Asn Ile Met Gln Val Leu
            255                 260                 265 aat acg caa tgc cct tta gtg cgt tcc acg aat aac gaa aac act cca       1273
Asn Thr Gln Cys Pro Leu Val Arg Ser Thr Asn Asn Glu Asn Thr Pro
        270                 275                 280
```

| | |
|---|---|
| ggg ggt ggt caa cca tgg ggt tta agc aca tcc ggg aat gcg tgc agc<br>Gly Gly Gly Gln Pro Trp Gly Leu Ser Thr Ser Gly Asn Ala Cys Ser<br>285                            290                              295 | 1321 |
| atc ttc caa caa gaa ttt agc cag gtt act agc atg atc aaa aac gcc<br>Ile Phe Gln Gln Glu Phe Ser Gln Val Thr Ser Met Ile Lys Asn Ala<br>300                            305                              310              315 | 1369 |
| caa gaa ata atc gcg caa agc aaa atc gtt agt gaa aac gcg caa aat<br>Gln Glu Ile Ile Ala Gln Ser Lys Ile Val Ser Glu Asn Ala Gln Asn<br>320                        325                              330 | 1417 |
| caa aac aac ttg gat act gga aaa cca ttc aac cct tac acg gac gcc<br>Gln Asn Asn Leu Asp Thr Gly Lys Pro Phe Asn Pro Tyr Thr Asp Ala<br>                335                            340                        345 | 1465 |
| agc ttt gcg caa agc atg ctc aaa aac gct caa gcg caa gca gag atg<br>Ser Phe Ala Gln Ser Met Leu Lys Asn Ala Gln Ala Gln Ala Glu Met<br>350                            355                              360 | 1513 |
| ttc aat ttg agc gaa caa gtg aaa aag aac ttg gaa gtc atg aaa aac<br>Phe Asn Leu Ser Glu Gln Val Lys Lys Asn Leu Glu Val Met Lys Asn<br>365                            370                              375 | 1561 |
| aac aat aat gtt aac gag aaa tta gca gga ttt ggg aaa gaa gaa gta<br>Asn Asn Asn Val Asn Glu Lys Leu Ala Gly Phe Gly Lys Glu Glu Val<br>380                            385                              390              395 | 1609 |
| atg acc aat ttt gtt agc gcc ttt ttg gca agc tgc aaa gat ggt ggc<br>Met Thr Asn Phe Val Ser Ala Phe Leu Ala Ser Cys Lys Asp Gly Gly<br>                            400                              405                        410 | 1657 |
| aca ttg cct aat gca ggg gtt act tct aac act tgg ggg gcg ggt tgc<br>Thr Leu Pro Asn Ala Gly Val Thr Ser Asn Thr Trp Gly Ala Gly Cys<br>                415                            420                        425 | 1705 |
| gcg tat gtg gga gag acg ata agc gcc cta acc aac agc atc gct cac<br>Ala Tyr Val Gly Glu Thr Ile Ser Ala Leu Thr Asn Ser Ile Ala His<br>430                            435                              440 | 1753 |
| ttt ggc act caa gag cag cag ata cag caa gcc gaa aac atc gct gac<br>Phe Gly Thr Gln Glu Gln Gln Ile Gln Gln Ala Glu Asn Ile Ala Asp<br>                445                            450                        455 | 1801 |
| act cta gtg aat ttc aaa tct aga tac agc gaa tta ggc aac acc tat<br>Thr Leu Val Asn Phe Lys Ser Arg Tyr Ser Glu Leu Gly Asn Thr Tyr<br>460                            465                              470              475 | 1849 |
| aac agc atc acc acc gcg ctc tcc aaa gtc cct aac gcg caa agc ttg<br>Asn Ser Ile Thr Thr Ala Leu Ser Lys Val Pro Asn Ala Gln Ser Leu<br>                            480                              485                        490 | 1897 |
| caa aac gtg gtg agc aaa aag aat aac ccc tat agc cct caa ggc ata<br>Gln Asn Val Val Ser Lys Lys Asn Asn Pro Tyr Ser Pro Gln Gly Ile<br>                            495                              500                        505 | 1945 |
| gag acc aat tac tac ctc aat caa aat tct tac aac caa atc caa acc<br>Glu Thr Asn Tyr Tyr Leu Asn Gln Asn Ser Tyr Asn Gln Ile Gln Thr<br>                            510                              515                        520 | 1993 |
| atc aac caa gaa cta ggg cgt aac ccc ttt agg aaa gtg ggc atc gtc<br>Ile Asn Gln Glu Leu Gly Arg Asn Pro Phe Arg Lys Val Gly Ile Val<br>525                            530                              535 | 2041 |
| aat tct caa acc aac aat ggt gcc atg aat ggg atc ggc att cag gtg<br>Asn Ser Gln Thr Asn Asn Gly Ala Met Asn Gly Ile Gly Ile Gln Val<br>540                            545                              550              555 | 2089 |
| ggc tat aag caa ttc ttt ggc caa aaa aga aaa tgg ggc gct agg tat<br>Gly Tyr Lys Gln Phe Phe Gly Gln Lys Arg Lys Trp Gly Ala Arg Tyr<br>                            560                              565                        570 | 2137 |
| tac ggc ttt ttt gat tac aac cat gcg ttc atc aaa tcc agc ttt ttc<br>Tyr Gly Phe Phe Asp Tyr Asn His Ala Phe Ile Lys Ser Ser Phe Phe<br>                575                            580                        585 | 2185 |
| aac tcg gct tct gac gtg tgg act tat ggt ttt gga gcg gac gcg ctt<br>Asn Ser Ala Ser Asp Val Trp Thr Tyr Gly Phe Gly Ala Asp Ala Leu<br>590                            595                              600 | 2233 |

```
tat aac ttc atc aac gat aaa gcc acc aat ttc tta ggc aaa aac aac   2281
Tyr Asn Phe Ile Asn Asp Lys Ala Thr Asn Phe Leu Gly Lys Asn Asn
        605                 610                 615 aag ctt tct ttg ggg ctt ttt ggc ggg att gcg tta gcg ggc act tca   2329
Lys Leu Ser Leu Gly Leu Phe Gly Gly Ile Ala Leu Ala Gly Thr Ser
620                 625                 630                 635 tgg ctc aat tct gag tac gtg aat tta gcc acc gtg aat aac gtc tat   2377
Trp Leu Asn Ser Glu Tyr Val Asn Leu Ala Thr Val Asn Asn Val Tyr
                640                 645                 650 aac gct aaa atg aat gtg gcg aat ttc caa ttc tta ttc aat atg gga   2425
Asn Ala Lys Met Asn Val Ala Asn Phe Gln Phe Leu Phe Asn Met Gly
            655                 660                 665 gtg agg atg aat tta gcc aga tcc aag aaa aaa ggc agc gat cat gca   2473
Val Arg Met Asn Leu Ala Arg Ser Lys Lys Lys Gly Ser Asp His Ala
        670                 675                 680 gct cag cat ggg att gag tta ggg ctt aaa atc ccc acc atc aac acg   2521
Ala Gln His Gly Ile Glu Leu Gly Leu Lys Ile Pro Thr Ile Asn Thr
    685                 690                 695 aac tat tat tcc ttt atg ggg gct gaa ctc aaa tac aga agg ctc tat   2569
Asn Tyr Tyr Ser Phe Met Gly Ala Glu Leu Lys Tyr Arg Arg Leu Tyr
700                 705                 710                 715 agc gtg tat ttg aat nat gtg ttc gct tac taagctttt gtgaaactcc     2619
Ser Val Tyr Leu Asn Xaa Val Phe Ala Tyr
                720                 725 ctttttaagg ggttttttt tgaactctct tttaaattct cttttaaag agatttcttt   2679 ttttaagctt tttttgaac tttttttga attctttgtt tttaagcttt ttttaaaccc   2739
tttcgttttt aaactccctt ttttaaggga tttcttttt tgaactccct ttttgaacc   2799 ctttttttta aaccctcttt ttttaagggg tttcttttta aagctttttt gaagtctttt 2859 tttaaattct tttttgggg gtttgatctt tcttttgcc aatccccact actttc       2915

<210> SEQ ID NO 6
<211> LENGTH: 745
<212> TYPE: PRT
<213> ORGANISM: Helicobacter pylori
<220> FEATURE:
<221> NAME/KEY: SIGNAL
<222> LOCATION: (1)...(20)
<220> FEATURE:
<221> NAME/KEY: VARIANT
<222> LOCATION: 721
<223> OTHER INFORMATION: Xaa = Any Amino Acid

<400> SEQUENCE: 6

Met Lys Lys His Ile Leu Ser Leu Ala Leu Gly Ser Leu Leu Val Ser
-20                 -15                 -10                 -5

Thr Leu Ser Ala Glu Asp Asp Gly Phe Tyr Thr Ser Val Gly Tyr Gln
                1                   5                   10

Ile Gly Glu Ala Ala Gln Met Val Thr Asn Thr Lys Gly Ile Gln Gln
        15                  20                  25

Leu Ser Asp Asn Tyr Glu Asn Leu Asn Asn Leu Leu Thr Arg Tyr Ser
    30                  35                  40

Thr Leu Asn Thr Leu Ile Lys Leu Ser Ala Asp Pro Ser Ala Ile Asn
45                  50                  55                  60

Ala Val Arg Glu Asn Leu Gly Ala Ser Thr Lys Asn Leu Ile Gly Asp
                65                  70                  75

Lys Ala Asn Ser Pro Ala Tyr Gln Ala Val Phe Leu Ala Ile Asn Ala
            80                  85                  90
```

-continued

```
Ala Val Gly Leu Trp Asn Thr Ile Gly Tyr Ala Val Met Cys Gly Asn
             95                  100                 105
Gly Asn Gly Thr Glu Ser Gly Pro Gly Ser Val Ile Phe Asn Asp Gln
        110                 115                 120
Pro Gly Gln Asp Ser Thr Gln Ile Thr Cys Asn Arg Phe Glu Ser Thr
125                 130                 135                 140
Gly Pro Gly Lys Ser Met Ser Ile Asp Glu Phe Lys Lys Leu Asn Glu
                145                 150                 155
Ala Tyr Gln Ile Ile Gln Gln Ala Leu Lys Asn Gln Ser Gly Phe Pro
            160                 165                 170
Glu Leu Gly Gly Asn Gly Thr Lys Val Ser Val Asn Tyr Asn Tyr Glu
            175                 180                 185
Cys Arg Gln Thr Ala Asp Ile Asn Gly Gly Val Tyr Gln Phe Cys Lys
        190                 195                 200
Ala Lys Asn Gly Ser Ser Ser Ser Asn Gly Gly Asn Gly Ser Ser
205                 210                 215                 220
Thr Gln Thr Thr Ala Thr Thr Gln Asp Gly Val Thr Ile Thr Thr
                225                 230                 235
Thr Tyr Asn Asn Asn Lys Ala Thr Val Lys Phe Asp Ile Thr Asn Asn
            240                 245                 250
Ala Glu Gln Leu Leu Asn Gln Ala Ala Asn Ile Met Gln Val Leu Asn
        255                 260                 265
Thr Gln Cys Pro Leu Val Arg Ser Thr Asn Asn Glu Asn Thr Pro Gly
    270                 275                 280
Gly Gly Gln Pro Trp Gly Leu Ser Thr Ser Gly Asn Ala Cys Ser Ile
285                 290                 295                 300
Phe Gln Gln Glu Phe Ser Gln Val Thr Ser Met Ile Lys Asn Ala Gln
                305                 310                 315
Glu Ile Ile Ala Gln Ser Lys Ile Val Ser Glu Asn Ala Gln Asn Gln
            320                 325                 330
Asn Asn Leu Asp Thr Gly Lys Pro Phe Asn Pro Tyr Thr Asp Ala Ser
        335                 340                 345
Phe Ala Gln Ser Met Leu Lys Asn Ala Gln Ala Gln Ala Glu Met Phe
350                 355                 360
Asn Leu Ser Glu Gln Val Lys Lys Asn Leu Glu Val Met Lys Asn Asn
365                 370                 375                 380
Asn Asn Val Asn Glu Lys Leu Ala Gly Phe Gly Lys Glu Glu Val Met
                385                 390                 395
Thr Asn Phe Val Ser Ala Phe Leu Ala Ser Cys Lys Asp Gly Gly Thr
            400                 405                 410
Leu Pro Asn Ala Gly Val Thr Ser Asn Thr Trp Gly Ala Gly Cys Ala
        415                 420                 425
Tyr Val Gly Glu Thr Ile Ser Ala Leu Thr Asn Ser Ile Ala His Phe
    430                 435                 440
Gly Thr Gln Glu Gln Gln Ile Gln Gln Ala Glu Asn Ile Ala Asp Thr
445                 450                 455                 460
Leu Val Asn Phe Lys Ser Arg Tyr Ser Glu Leu Gly Asn Thr Tyr Asn
                465                 470                 475
Ser Ile Thr Thr Ala Leu Ser Lys Val Pro Asn Ala Gln Ser Leu Gln
            480                 485                 490
Asn Val Val Ser Lys Lys Asn Asn Pro Tyr Ser Pro Gln Gly Ile Glu
        495                 500                 505
Thr Asn Tyr Tyr Leu Asn Gln Asn Ser Tyr Asn Gln Ile Gln Thr Ile
```

-continued

```
                                510                 515                 520
Asn Gln Glu Leu Gly Arg Asn Pro Phe Arg Lys Val Gly Ile Val Asn
525                 530                 535                 540

Ser Gln Thr Asn Asn Gly Ala Met Asn Gly Ile Gly Ile Gln Val Gly
                545                 550                 555

Tyr Lys Gln Phe Phe Gly Gln Lys Arg Lys Trp Gly Ala Arg Tyr Tyr
            560                 565                 570

Gly Phe Phe Asp Tyr Asn His Ala Phe Ile Lys Ser Ser Phe Phe Asn
        575                 580                 585

Ser Ala Ser Asp Val Trp Thr Tyr Gly Phe Gly Ala Asp Ala Leu Tyr
590                 595                 600

Asn Phe Ile Asn Asp Lys Ala Thr Asn Phe Leu Gly Lys Asn Asn Lys
605                 610                 615                 620

Leu Ser Leu Gly Leu Phe Gly Gly Ile Ala Leu Ala Gly Thr Ser Trp
                625                 630                 635

Leu Asn Ser Glu Tyr Val Asn Leu Ala Thr Val Asn Asn Val Tyr Asn
            640                 645                 650

Ala Lys Met Asn Val Ala Asn Phe Gln Phe Leu Phe Asn Met Gly Val
        655                 660                 665

Arg Met Asn Leu Ala Arg Ser Lys Lys Gly Ser Asp His Ala Ala
    670                 675                 680

Gln His Gly Ile Glu Leu Gly Leu Lys Ile Pro Thr Ile Asn Thr Asn
685                 690                 695                 700

Tyr Tyr Ser Phe Met Gly Ala Glu Leu Lys Tyr Arg Arg Leu Tyr Ser
                705                 710                 715

Val Tyr Leu Asn Xaa Val Phe Ala Tyr
            720                 725
```

<210> SEQ ID NO 7
<211> LENGTH: 2603
<212> TYPE: DNA
<213> ORGANISM: Helicobacter pylori
<220> FEATURE:
<221> NAME/KEY: CDS
<222> LOCATION: (210)...(2342)
<220> FEATURE:
<221> NAME/KEY: sig_peptide
<222> LOCATION: (210)...(270)

<400> SEQUENCE: 7

```
atgaccttta ttggtttaat atttgtttag aaataacaca aaaacctttt ttttttttt        60 tgaaagggca aaaacgccta attaatatca aaatcccatg aatttatact atattaacga      120
aagcttgcgg tatggtttca cctaaagaca cacttccgca agatttacta acaatttcaa      180
tcttatttca agtaataaaa ggagaaaac atg aag aaa aaa ttt ctg tca tta       233
                                 Met Lys Lys Lys Phe Leu Ser Leu
                                 -20                 -15 acc tta ggt tcg ctt tta gtt tcc gct tta agc gct gaa gac aac ggc       281
Thr Leu Gly Ser Leu Leu Val Ser Ala Leu Ser Ala Glu Asp Asn Gly
        -10                 -5                   1 ttt ttt gtg agt gcg ggc tat caa atc ggt gaa tcc gct caa atg gtg       329
Phe Phe Val Ser Ala Gly Tyr Gln Ile Gly Glu Ser Ala Gln Met Val
 5                  10                  15                  20 aaa aac act aaa ggc att caa gat ctt tca gat agc tat gaa aga ctg       377
Lys Asn Thr Lys Gly Ile Gln Asp Leu Ser Asp Ser Tyr Glu Arg Leu
                25                  30                  35 aac aat ctt tta acg agt tat agt gcc cta aac act ctt att agg cag       425
Asn Asn Leu Leu Thr Ser Tyr Ser Ala Leu Asn Thr Leu Ile Arg Gln
```

|  |  |  |  |  |  |  |  |  |  |  |  |  |  |
|---|---|---|---|---|---|---|---|---|---|---|---|---|---|
|  |  | 40 |  |  |  | 45 |  |  |  | 50 |  |  |  |

```
tcc gcc gac ccc aac gct atc aat aac gca agg ggc aat ttg aac gct     473
Ser Ala Asp Pro Asn Ala Ile Asn Asn Ala Arg Gly Asn Leu Asn Ala
             55                  60                  65 agt gcg aag aat ttg atc aat gat aaa aag aat tcc ccg gcg tat caa     521
Ser Ala Lys Asn Leu Ile Asn Asp Lys Lys Asn Ser Pro Ala Tyr Gln
     70                  75                  80 gcg gtg ctt tta gcc ttg aat gcg gca gcg ggg ttg tgg caa gtc atg     569
Ala Val Leu Leu Ala Leu Asn Ala Ala Ala Gly Leu Trp Gln Val Met
 85                  90                  95                 100 agc tat tcg atc agc gtt tgt ggc cct ggc tct gac aaa aat aaa aat     617
Ser Tyr Ser Ile Ser Val Cys Gly Pro Gly Ser Asp Lys Asn Lys Asn
                    105                 110                 115 ggg ggc gtc caa acc ttt gaa aat gtg ccg tca aat ggg ggg act acc     665
Gly Gly Val Gln Thr Phe Glu Asn Val Pro Ser Asn Gly Gly Thr Thr
                120                 125                 130 att gct tgc gat tca ttt tat gaa cca gga aag tgg agc ggt ata tcc     713
Ile Ala Cys Asp Ser Phe Tyr Glu Pro Gly Lys Trp Ser Gly Ile Ser
            135                 140                 145 act gaa aat tac gca aaa atc aat aaa gcc tat caa atc atc caa aag     761
Thr Glu Asn Tyr Ala Lys Ile Asn Lys Ala Tyr Gln Ile Ile Gln Lys
        150                 155                 160 gct ttt gga gca agc ggg caa gat att cct gcc tta agc gac acc aaa     809
Ala Phe Gly Ala Ser Gly Gln Asp Ile Pro Ala Leu Ser Asp Thr Lys
165                 170                 175                 180 gaa ctt aat ttt gaa att aaa ggg aaa aaa aat gat agc gtc cag cca     857
Glu Leu Asn Phe Glu Ile Lys Gly Lys Lys Asn Asp Ser Val Gln Pro
                    185                 190                 195 gga gaa aga tgg aaa ttc cca tgg act aat gga aaa ttt gtt tca gtc     905
Gly Glu Arg Trp Lys Phe Pro Trp Thr Asn Gly Lys Phe Val Ser Val
                200                 205                 210 aag tgg gtg aat ggg aag tat gaa gaa att aaa gaa gac atc aaa gtg     953
Lys Trp Val Asn Gly Lys Tyr Glu Glu Ile Lys Glu Asp Ile Lys Val
            215                 220                 225 tca aat aac gct caa gag ctt tta aaa cag gct agc act att tta acc    1001
Ser Asn Asn Ala Gln Glu Leu Leu Lys Gln Ala Ser Thr Ile Leu Thr
        230                 235                 240 act ctt aat gaa gca tgc cca tgg ttg agt aat ggt ggt gca ggc aat    1049
Thr Leu Asn Glu Ala Cys Pro Trp Leu Ser Asn Gly Gly Ala Gly Asn
245                 250                 255                 260 gtg gcc ggt ggc aat agt tta tgg gcc gga ata gat aaa ggc gac ggg    1097
Val Ala Gly Gly Asn Ser Leu Trp Ala Gly Ile Asp Lys Gly Asp Gly
                    265                 270                 275 agc gca tgc ggg att ttt aaa aat gaa atc agc gcg att caa gac atg    1145
Ser Ala Cys Gly Ile Phe Lys Asn Glu Ile Ser Ala Ile Gln Asp Met
                280                 285                 290 atc aaa aac gct gaa ata gcc gta gag caa tcc aaa atc gtt acc gcc    1193
Ile Lys Asn Ala Glu Ile Ala Val Glu Gln Ser Lys Ile Val Thr Ala
            295                 300                 305 aac gcg caa aac cag cac aac cta gac act ggg aaa gca ttc aac ccc    1241
Asn Ala Gln Asn Gln His Asn Leu Asp Thr Gly Lys Ala Phe Asn Pro
        310                 315                 320 tat aaa gac gcc aac ttc gcc caa agc atg ttc gct aac gct aga gcg    1289
Tyr Lys Asp Ala Asn Phe Ala Gln Ser Met Phe Ala Asn Ala Arg Ala
325                 330                 335                 340 caa gcg gag att tta aac cgc gct caa gca gtg gtg aag gac ttt gaa    1337
Gln Ala Glu Ile Leu Asn Arg Ala Gln Ala Val Val Lys Asp Phe Glu
                    345                 350                 355 aga atc cct gca gcg ttc gtg aaa gac tct tta gga gta tgc cat gaa    1385
```

```
                                                            -continued

Arg Ile Pro Ala Ala Phe Val Lys Asp Ser Leu Gly Val Cys His Glu
        360                 365                 370 aag ggt agc gac ggc aat ctc cgt ggc acg cca tct ggc acg gtt act      1433
Lys Gly Ser Asp Gly Asn Leu Arg Gly Thr Pro Ser Gly Thr Val Thr
        375                 380                 385 tct aac act tgg gga gcc ggc tgc gcg tat gtg gga gaa acc gta acg      1481
Ser Asn Thr Trp Gly Ala Gly Cys Ala Tyr Val Gly Glu Thr Val Thr
        390                 395                 400 aat cta aaa aac agc atc gct cat ttt ggc gac caa gcg gag cga atc      1529
Asn Leu Lys Asn Ser Ile Ala His Phe Gly Asp Gln Ala Glu Arg Ile
405                 410                 415                 420 cat aat gcg cga aat ctc gcc tac act tta gcg aat ttc agc ggc cag      1577
His Asn Ala Arg Asn Leu Ala Tyr Thr Leu Ala Asn Phe Ser Gly Gln
            425                 430                 435 tac aaa aag cta ggc gaa cac tat gac agc atc aca gcg gcg ctc tct      1625
Tyr Lys Lys Leu Gly Glu His Tyr Asp Ser Ile Thr Ala Ala Leu Ser
        440                 445                 450 agc ttg cct gat gcg caa tct tta caa aat gtg gtg agc aaa aag act      1673
Ser Leu Pro Asp Ala Gln Ser Leu Gln Asn Val Val Ser Lys Lys Thr
        455                 460                 465 aac cct aac agc ccg caa ggc ata cag gat aat tac tac att gac tcc      1721
Asn Pro Asn Ser Pro Gln Gly Ile Gln Asp Asn Tyr Tyr Ile Asp Ser
        470                 475                 480 aac atc cat tct caa gtg caa tct agg agt caa gaa ctc ggc agt aac      1769
Asn Ile His Ser Gln Val Gln Ser Arg Ser Gln Glu Leu Gly Ser Asn
485                 490                 495                 500 cct ttc aga cgc gcc ggg cta atc gcc gct tct acc acc aat aac ggc      1817
Pro Phe Arg Arg Ala Gly Leu Ile Ala Ala Ser Thr Thr Asn Asn Gly
            505                 510                 515 gcg atg aat ggg att ggc ttt caa gtg ggc tat aag caa ttc ttt ggg      1865
Ala Met Asn Gly Ile Gly Phe Gln Val Gly Tyr Lys Gln Phe Phe Gly
        520                 525                 530 aaa aac aaa cga tgg ggc gcg aga tac tac ggc ttt gtg gat tac aac      1913
Lys Asn Lys Arg Trp Gly Ala Arg Tyr Tyr Gly Phe Val Asp Tyr Asn
        535                 540                 545 cac acc tat aac aag tcc caa ttt ttc aac tcc gat tct gat gtt tgg      1961
His Thr Tyr Asn Lys Ser Gln Phe Phe Asn Ser Asp Ser Asp Val Trp
        550                 555                 560 act tat ggc gtg ggg agc gat ttg tta gtg aat ttc atc aac gat aaa      2009
Thr Tyr Gly Val Gly Ser Asp Leu Leu Val Asn Phe Ile Asn Asp Lys
565                 570                 575                 580 gcc act aaa cac aat aaa att tct ttt ggc gcg ttt ggc ggt atc caa      2057
Ala Thr Lys His Asn Lys Ile Ser Phe Gly Ala Phe Gly Gly Ile Gln
            585                 590                 595 cta gcc ggg act tca tgg ctt aat tct cag tat gtg aat tta gcg aat      2105
Leu Ala Gly Thr Ser Trp Leu Asn Ser Gln Tyr Val Asn Leu Ala Asn
        600                 605                 610 gtg aac aat tat tat aaa gct aaa atc aac acc tct aac ttc caa ttc      2153
Val Asn Asn Tyr Tyr Lys Ala Lys Ile Asn Thr Ser Asn Phe Gln Phe
        615                 620                 625 tta ttc aat ctg ggc tta agg acc aat ctc gcc aga aat aaa aga ata      2201
Leu Phe Asn Leu Gly Leu Arg Thr Asn Leu Ala Arg Asn Lys Arg Ile
        630                 635                 640 ggc gct gat cat agc gcg caa cat ggc atg gaa tta ggc gtg aag atc      2249
Gly Ala Asp His Ser Ala Gln His Gly Met Glu Leu Gly Val Lys Ile
645                 650                 655                 660 ccc acg atc aac aca aat tac tat tct ttg cta ggc act acc ttg caa      2297
Pro Thr Ile Asn Thr Asn Tyr Tyr Ser Leu Leu Gly Thr Thr Leu Gln
            665                 670                 675
```

-continued

```
tac aga agg ctt tat agc gtg tat ctc aac tat gtg ttt gct tac    2342
Tyr Arg Arg Leu Tyr Ser Val Tyr Leu Asn Tyr Val Phe Ala Tyr
            680                 685                 690 taaaagctta aactcctttt taaactccct ttttaggggg tttaatctttt ttaactgact   2402 tttcttttag cttttttttaa ttttttccac caaacaaagt ttttttgactt caagcgttaa   2462 tcacaaaaaa tactcaaagg cgttttttgc aatctaaata aaaaattagc gttattcaag   2522
cgatcatttt aaaccaccca agcaagaaac cccaaacatc tttagcgttc gcgcgctcca   2582
ctaaccaaaa aacgccccaa a                                             2603
```

<210> SEQ ID NO 8
<211> LENGTH: 711
<212> TYPE: PRT
<213> ORGANISM: Helicobacter pylori
<220> FEATURE:
<221> NAME/KEY: SIGNAL
<222> LOCATION: (1)...(20)

<400> SEQUENCE: 8

```
Met Lys Lys Phe Leu Ser Leu Thr Leu Gly Ser Leu Leu Val Ser
-20             -15                 -10                 -5

Ala Leu Ser Ala Glu Asp Asn Gly Phe Phe Val Ser Ala Gly Tyr Gln
                1                   5                   10

Ile Gly Glu Ser Ala Gln Met Val Lys Asn Thr Lys Gly Ile Gln Asp
        15                  20                  25

Leu Ser Asp Ser Tyr Glu Arg Leu Asn Asn Leu Leu Thr Ser Tyr Ser
    30                  35                  40

Ala Leu Asn Thr Leu Ile Arg Gln Ser Ala Asp Pro Asn Ala Ile Asn
45                  50                  55                  60

Asn Ala Arg Gly Asn Leu Asn Ala Ser Ala Lys Asn Leu Ile Asn Asp
                65                  70                  75

Lys Lys Asn Ser Pro Ala Tyr Gln Ala Val Leu Leu Ala Leu Asn Ala
            80                  85                  90

Ala Ala Gly Leu Trp Gln Val Met Ser Tyr Ser Ile Ser Val Cys Gly
        95                  100                 105

Pro Gly Ser Asp Lys Asn Lys Asn Gly Gly Val Gln Thr Phe Glu Asn
    110                 115                 120

Val Pro Ser Asn Gly Gly Thr Thr Ile Ala Cys Asp Ser Phe Tyr Glu
125                 130                 135                 140

Pro Gly Lys Trp Ser Gly Ile Ser Thr Glu Asn Tyr Ala Lys Ile Asn
                145                 150                 155

Lys Ala Tyr Gln Ile Ile Gln Lys Ala Phe Gly Ala Ser Gly Gln Asp
            160                 165                 170

Ile Pro Ala Leu Ser Asp Thr Lys Glu Leu Asn Phe Glu Ile Lys Gly
        175                 180                 185

Lys Lys Asn Asp Ser Val Gln Pro Gly Glu Arg Trp Lys Phe Pro Trp
    190                 195                 200

Thr Asn Gly Lys Phe Val Ser Val Lys Trp Val Asn Gly Lys Tyr Glu
205                 210                 215                 220

Glu Ile Lys Glu Asp Ile Lys Val Ser Asn Asn Ala Gln Glu Leu Leu
                225                 230                 235

Lys Gln Ala Ser Thr Ile Leu Thr Thr Leu Asn Glu Ala Cys Pro Trp
            240                 245                 250

Leu Ser Asn Gly Gly Ala Gly Asn Val Ala Gly Gly Asn Ser Leu Trp
        255                 260                 265
```

-continued

```
Ala Gly Ile Asp Lys Gly Asp Gly Ser Ala Cys Gly Ile Phe Lys Asn
270                 275                 280

Glu Ile Ser Ala Ile Gln Asp Met Ile Lys Asn Ala Glu Ile Ala Val
285                 290                 295                 300

Glu Gln Ser Lys Ile Val Thr Ala Asn Ala Gln Asn Gln His Asn Leu
                305                 310                 315

Asp Thr Gly Lys Ala Phe Asn Pro Tyr Lys Asp Ala Asn Phe Ala Gln
                320                 325                 330

Ser Met Phe Ala Asn Ala Arg Ala Gln Ala Glu Ile Leu Asn Arg Ala
            335                 340                 345

Gln Ala Val Val Lys Asp Phe Glu Arg Ile Pro Ala Ala Phe Val Lys
            350                 355                 360

Asp Ser Leu Gly Val Cys His Glu Lys Gly Ser Asp Gly Asn Leu Arg
365                 370                 375                 380

Gly Thr Pro Ser Gly Thr Val Thr Ser Asn Thr Trp Gly Ala Gly Cys
                385                 390                 395

Ala Tyr Val Gly Glu Thr Val Thr Asn Leu Lys Asn Ser Ile Ala His
                400                 405                 410

Phe Gly Asp Gln Ala Glu Arg Ile His Asn Ala Arg Asn Leu Ala Tyr
            415                 420                 425

Thr Leu Ala Asn Phe Ser Gly Gln Tyr Lys Lys Leu Gly Glu His Tyr
    430                 435                 440

Asp Ser Ile Thr Ala Ala Leu Ser Ser Leu Pro Asp Ala Gln Ser Leu
445                 450                 455                 460

Gln Asn Val Val Ser Lys Lys Thr Asn Pro Asn Ser Pro Gln Gly Ile
                465                 470                 475

Gln Asp Asn Tyr Tyr Ile Asp Ser Asn Ile His Ser Gln Val Gln Ser
                480                 485                 490

Arg Ser Gln Glu Leu Gly Ser Asn Pro Phe Arg Arg Ala Gly Leu Ile
            495                 500                 505

Ala Ala Ser Thr Thr Asn Asn Gly Ala Met Asn Gly Ile Gly Phe Gln
            510                 515                 520

Val Gly Tyr Lys Gln Phe Phe Gly Lys Asn Lys Arg Trp Gly Ala Arg
525                 530                 535                 540

Tyr Tyr Gly Phe Val Asp Tyr Asn His Thr Tyr Asn Lys Ser Gln Phe
                545                 550                 555

Phe Asn Ser Asp Ser Asp Val Trp Thr Tyr Gly Val Gly Ser Asp Leu
                560                 565                 570

Leu Val Asn Phe Ile Asn Asp Lys Ala Thr Lys His Asn Lys Ile Ser
            575                 580                 585

Phe Gly Ala Phe Gly Gly Ile Gln Leu Ala Gly Thr Ser Trp Leu Asn
            590                 595                 600

Ser Gln Tyr Val Asn Leu Ala Asn Val Asn Asn Tyr Lys Ala Lys
605                 610                 615                 620

Ile Asn Thr Ser Asn Phe Gln Phe Leu Phe Asn Leu Gly Leu Arg Thr
                625                 630                 635

Asn Leu Ala Arg Asn Lys Arg Ile Gly Ala Asp His Ser Ala Gln His
            640                 645                 650

Gly Met Glu Leu Gly Val Lys Ile Pro Thr Ile Asn Thr Asn Tyr Tyr
            655                 660                 665

Ser Leu Leu Gly Thr Thr Leu Gln Tyr Arg Arg Leu Tyr Ser Val Tyr
670                 675                 680

Leu Asn Tyr Val Phe Ala Tyr
```

<210> SEQ ID NO 9
<211> LENGTH: 2427
<212> TYPE: DNA
<213> ORGANISM: Helicobacter pylori
<220> FEATURE:
<221> NAME/KEY: CDS
<222> LOCATION: (232)...(2247)
<220> FEATURE:
<221> NAME/KEY: sig_peptide
<222> LOCATION: (232)...(292)

<400> SEQUENCE: 9

| | | |
|---|---|---|
| aaaacgcgca gcaaaaaatc tctgttaagc ttttatcatt agcgttccat tgaaacaaaa | 60 |
| tctaaaaacc ctttccaata ccacccaaac aaacgcgcaa aaaatgcaaa aattctaaat | 120 |
| tttctccaaa tgacaaaaaa aaaaaaaacg attttatgct acaatgcttt taatacattc | 180 |
| ttacttaatg tataaaatct caatcactca atttaatttc aaaggatatt t atg aaa | 237 |
| Met Lys -20 | |

| aaa acc ctt tta ctc tct ctc tct ctc tct ctc tcg tca tcg ctt tta | 285 |
|---|---|
| Lys Thr Leu Leu Leu Ser Leu Ser Leu Ser Leu Ser Ser Ser Leu Leu | |
| -15 -10 -5 | |

| aac gct gaa gac aac ggc ttt ttt atc agc gcg ggc tat caa atc ggt | 333 |
|---|---|
| Asn Ala Glu Asp Asn Gly Phe Phe Ile Ser Ala Gly Tyr Gln Ile Gly | |
| 1 5 10 | |

| gaa gcc gct caa atg gtg aaa aac acc ggc gaa ttg aaa aaa ctt tca | 381 |
|---|---|
| Glu Ala Ala Gln Met Val Lys Asn Thr Gly Glu Leu Lys Lys Leu Ser | |
| 15 20 25 30 | |

| gac act tat gag aat ttg agc aac ctt tta acc aat ttt aac aac ctc | 429 |
|---|---|
| Asp Thr Tyr Glu Asn Leu Ser Asn Leu Leu Thr Asn Phe Asn Asn Leu | |
| 35 40 45 | |

| aat caa gcg gta acg aac gcg agc agc cct tca gaa atc aat gcc acg | 477 |
|---|---|
| Asn Gln Ala Val Thr Asn Ala Ser Ser Pro Ser Glu Ile Asn Ala Thr | |
| 50 55 60 | |

| atc gat aat tta aaa gca aac acg caa ggg ctg att ggc gaa aaa acc | 525 |
|---|---|
| Ile Asp Asn Leu Lys Ala Asn Thr Gln Gly Leu Ile Gly Glu Lys Thr | |
| 65 70 75 | |

| aat tcc ccg gcg tat caa gcg gtg tat ttg gcg ctc aat gcg gcg gtg | 573 |
|---|---|
| Asn Ser Pro Ala Tyr Gln Ala Val Tyr Leu Ala Leu Asn Ala Ala Val | |
| 80 85 90 | |

| ggg ctg tgg aat gtg ata gcc tat aat gtc caa tgc ggt cct ggt aag | 621 |
|---|---|
| Gly Leu Trp Asn Val Ile Ala Tyr Asn Val Gln Cys Gly Pro Gly Lys | |
| 95 100 105 110 | |

| agt ggg gat caa agc gta att ttt gat ggc caa cca gga cat gat tca | 669 |
|---|---|
| Ser Gly Asp Gln Ser Val Ile Phe Asp Gly Gln Pro Gly His Asp Ser | |
| 115 120 125 | |

| aga tcc att aat tgc aat tta acc ggt tat aac aac ggg gtt agc ggc | 717 |
|---|---|
| Arg Ser Ile Asn Cys Asn Leu Thr Gly Tyr Asn Asn Gly Val Ser Gly | |
| 130 135 140 | |

| cct tta tcc att gac aat ttt aaa acg ctt aat caa gct tat caa act | 765 |
|---|---|
| Pro Leu Ser Ile Asp Asn Phe Lys Thr Leu Asn Gln Ala Tyr Gln Thr | |
| 145 150 155 | |

| atc caa caa gct tta aaa caa gat agc gga ttt cct gtt ttg gat agt | 813 |
|---|---|
| Ile Gln Gln Ala Leu Lys Gln Asp Ser Gly Phe Pro Val Leu Asp Ser | |
| 160 165 170 | |

| aaa gga aaa caa gta act ata aaa ata aca aca caa act aat gga gct | 861 |
|---|---|
| Lys Gly Lys Gln Val Thr Ile Lys Ile Thr Thr Gln Thr Asn Gly Ala | |
| 175 180 185 190 | |

| aat aaa agt gaa act act act act act act act aat gac gct caa | 909 |
|---|---|

```
                                                            -continued

Asn Lys Ser Glu Thr Thr Thr Thr Thr Thr Thr Asn Asp Ala Gln
            195                 200                 205 acc ctt ttg caa gaa gcc agt aaa atg ata agc gtc ctc act aca aac         957
Thr Leu Leu Gln Glu Ala Ser Lys Met Ile Ser Val Leu Thr Thr Asn
            210                 215                 220 tgc cca tgg gta aat acc gct cat aac tca aac ggg ggt gca ccg tgg        1005
Cys Pro Trp Val Asn Thr Ala His Asn Ser Asn Gly Gly Ala Pro Trp
            225                 230                 235 aat tta aat acg aca ggg aat gtg tgt cag gtt ttt gcc acg gag ttt        1053
Asn Leu Asn Thr Thr Gly Asn Val Cys Gln Val Phe Ala Thr Glu Phe
            240                 245                 250 agc gcc gtt act agc atg atc aaa aac gcg caa gaa atc gta acg caa        1101
Ser Ala Val Thr Ser Met Ile Lys Asn Ala Gln Glu Ile Val Thr Gln
255                 260                 265                 270 gct caa agc ctt aac aac ccg caa agc aat caa aac gcg ccg aaa gat        1149
Ala Gln Ser Leu Asn Asn Pro Gln Ser Asn Gln Asn Ala Pro Lys Asp
            275                 280                 285 ttc aat cct tac acc tct gct gat agg gct ttc gct caa aac atg ctc        1197
Phe Asn Pro Tyr Thr Ser Ala Asp Arg Ala Phe Ala Gln Asn Met Leu
            290                 295                 300 aat cac gcg caa gcg caa gcc aag atg ctt gaa cta gcc gat caa atg        1245
Asn His Ala Gln Ala Gln Ala Lys Met Leu Glu Leu Ala Asp Gln Met
            305                 310                 315 aaa aaa gac ctt aac act atc cca aaa caa ttt atc aca aac tac ttg        1293
Lys Lys Asp Leu Asn Thr Ile Pro Lys Gln Phe Ile Thr Asn Tyr Leu
320                 325                 330 gca gct tgc cgc aat ggg ggt ggg aca tta cct gat gca ggg gtt act        1341
Ala Ala Cys Arg Asn Gly Gly Gly Thr Leu Pro Asp Ala Gly Val Thr
335                 340                 345                 350 tct aac act tgg ggg gcc ggt tgc gcc tat gtg gaa gag acg ata acc        1389
Ser Asn Thr Trp Gly Ala Gly Cys Ala Tyr Val Glu Glu Thr Ile Thr
            355                 360                 365 gcc cta aat aac agc ctt gcg cat ttt ggc act caa gcc gat caa atc        1437
Ala Leu Asn Asn Ser Leu Ala His Phe Gly Thr Gln Ala Asp Gln Ile
            370                 375                 380 aag caa tct gag ttg ttg gcg cgc acg ata ctt gat ttt aga ggc agc        1485
Lys Gln Ser Glu Leu Leu Ala Arg Thr Ile Leu Asp Phe Arg Gly Ser
            385                 390                 395 ctt aag gat tta aac aac act tat aac agc atc acc acg acc gct tca        1533
Leu Lys Asp Leu Asn Asn Thr Tyr Asn Ser Ile Thr Thr Thr Ala Ser
            400                 405                 410 aac acg ccc aat tcc cca ttc ctt aaa aat ttg ata agc caa tcc act        1581
Asn Thr Pro Asn Ser Pro Phe Leu Lys Asn Leu Ile Ser Gln Ser Thr
415                 420                 425                 430 aac cct aat aac ccc ggg ggc tta cag gcc gtt tat caa gtc aac caa        1629
Asn Pro Asn Asn Pro Gly Gly Leu Gln Ala Val Tyr Gln Val Asn Gln
            435                 440                 445 agc gct tat tcg caa tta tta agc gcc acg caa gaa tta ggg cat aac        1677
Ser Ala Tyr Ser Gln Leu Leu Ser Ala Thr Gln Glu Leu Gly His Asn
            450                 455                 460 cct ttc aga cgc gtt ggc tta atc agc tct caa acc aac aac ggt gcg        1725
Pro Phe Arg Arg Val Gly Leu Ile Ser Ser Gln Thr Asn Asn Gly Ala
            465                 470                 475 atg aat ggg atc ggc gtg caa ata ggg tat aaa caa ttt ttt ggt gaa        1773
Met Asn Gly Ile Gly Val Gln Ile Gly Tyr Lys Gln Phe Phe Gly Glu
            480                 485                 490 aaa aga aga tgg ggg tta agg tat tat ggt ttt ttt gat tac aac cat        1821
Lys Arg Arg Trp Gly Leu Arg Tyr Tyr Gly Phe Phe Asp Tyr Asn His
495                 500                 505                 510
```

-continued

| | | | | | | | | | | | | | | |
|---|---|---|---|---|---|---|---|---|---|---|---|---|---|---|
| gct | tat | atc | aaa | tcc | agc | ttt | ttc | aac | tcc | gcc | tct | gat | gtg | ttc act | 1869 |
| Ala | Tyr | Ile | Lys | Ser | Ser | Phe | Phe | Asn | Ser | Ala | Ser | Asp | Val | Phe Thr |
| | | | 515 | | | | 520 | | | | | 525 | | |

| tat | ggg | gta | gga | aca | gat | gtc | ctc | tat | aac | ttt | atc | aac | gat | aaa gcc | 1917 |
| Tyr | Gly | Val | Gly | Thr | Asp | Val | Leu | Tyr | Asn | Phe | Ile | Asn | Asp | Lys Ala |
| | | 530 | | | | | 535 | | | | | 540 | | |

| acc | aaa | aac | aat | aag | att | tct | ttt | ggg | gtg | ttt | ggg | ggg | att | gcg tta | 1965 |
| Thr | Lys | Asn | Asn | Lys | Ile | Ser | Phe | Gly | Val | Phe | Gly | Gly | Ile | Ala Leu |
| | | | 545 | | | | 550 | | | | | 555 | | |

| gct | ggc | act | tcg | tgg | ctt | aat | tct | caa | tac | gtg | aat | tta | gcg | aca ttc | 2013 |
| Ala | Gly | Thr | Ser | Trp | Leu | Asn | Ser | Gln | Tyr | Val | Asn | Leu | Ala | Thr Phe |
| | | 560 | | | | | 565 | | | | | 570 | | |

| aat | aat | ttt | tac | agc | gct | aaa | atg | aat | gtg | gcg | aat | ttc | caa | ttc tta | 2061 |
| Asn | Asn | Phe | Tyr | Ser | Ala | Lys | Met | Asn | Val | Ala | Asn | Phe | Gln | Phe Leu |
| 575 | | | | 580 | | | | 585 | | | | | 590 | |

| ttc | aac | ttg | ggc | ttg | aga | atg | aat | ctc | gct | aaa | aac | aaa | aag | aaa gcg | 2109 |
| Phe | Asn | Leu | Gly | Leu | Arg | Met | Asn | Leu | Ala | Lys | Asn | Lys | Lys | Lys Ala |
| | | | 595 | | | | 600 | | | | | 605 | | |

| agc | gat | cat | gta | gct | cag | cat | ggc | gtg | gaa | cta | ggc | gtg | aag | atc cct | 2157 |
| Ser | Asp | His | Val | Ala | Gln | His | Gly | Val | Glu | Leu | Gly | Val | Lys | Ile Pro |
| | | 610 | | | | | 615 | | | | | 620 | | |

| acg | atc | aac | acg | aat | tac | tat | tct | ttg | cta | ggc | act | caa | ctc | caa tac | 2205 |
| Thr | Ile | Asn | Thr | Asn | Tyr | Tyr | Ser | Leu | Leu | Gly | Thr | Gln | Leu | Gln Tyr |
| | | | 625 | | | | 630 | | | | | 635 | | |

| cgc | agg | ctt | tat | agc | gtg | tat | ttg | aat | tat | gtg | ttt | gct | tac | | 2247 |
| Arg | Arg | Leu | Tyr | Ser | Val | Tyr | Leu | Asn | Tyr | Val | Phe | Ala | Tyr | |
| | 640 | | | | | 645 | | | | | 650 | | | | taatatctgt cttttttgtga aactcccttt ttaagggatt tttttttgaag cctttctttt    2307 tttaaaccct ctttttttggg ggtcaagcgt aaaattcacc cctatcccttt taagaaaata    2367 aaataaaaga aaatgcgttt tataacaaaa taagatctaa aacaataaaa caaaaaccca    2427

<210> SEQ ID NO 10
<211> LENGTH: 672
<212> TYPE: PRT
<213> ORGANISM: Helicobacter pylori
<220> FEATURE:
<221> NAME/KEY: SIGNAL
<222> LOCATION: (1)...(20)

<400> SEQUENCE: 10

Met Lys Lys Thr Leu Leu Leu Ser Leu Ser Leu Ser Ser
-20              -15              -10              -5

Leu Leu Asn Ala Glu Asp Asn Gly Phe Phe Ile Ser Ala Gly Tyr Gln
                 1               5                   10

Ile Gly Glu Ala Ala Gln Met Val Lys Asn Thr Gly Glu Leu Lys Lys
         15                  20                  25

Leu Ser Asp Thr Tyr Glu Asn Leu Ser Asn Leu Thr Asn Phe Asn
     30                  35                  40

Asn Leu Asn Gln Ala Val Thr Asn Ala Ser Ser Pro Ser Glu Ile Asn
45                  50                  55                  60

Ala Thr Ile Asp Asn Leu Lys Ala Asn Thr Gln Gly Leu Ile Gly Glu
             65                  70                  75

Lys Thr Asn Ser Pro Ala Tyr Gln Ala Val Tyr Leu Ala Leu Asn Ala
         80                  85                  90

Ala Val Gly Leu Trp Asn Val Ile Ala Tyr Asn Val Gln Cys Gly Pro
     95                  100                 105

Gly Lys Ser Gly Asp Gln Ser Val Ile Phe Asp Gly Gln Pro Gly His
     110                 115                 120

-continued

```
Asp Ser Arg Ser Ile Asn Cys Asn Leu Thr Gly Tyr Asn Asn Gly Val
125                 130                 135                 140

Ser Gly Pro Leu Ser Ile Asp Asn Phe Lys Thr Leu Asn Gln Ala Tyr
            145                 150                 155

Gln Thr Ile Gln Gln Ala Leu Lys Gln Asp Ser Gly Phe Pro Val Leu
        160                 165                 170

Asp Ser Lys Gly Lys Gln Val Thr Ile Lys Ile Thr Thr Gln Thr Asn
        175                 180                 185

Gly Ala Asn Lys Ser Glu Thr Thr Thr Thr Thr Thr Thr Thr Asn Asp
    190                 195                 200

Ala Gln Thr Leu Leu Gln Glu Ala Ser Lys Met Ile Ser Val Leu Thr
205                 210                 215                 220

Thr Asn Cys Pro Trp Val Asn Thr Ala His Asn Ser Asn Gly Gly Ala
                225                 230                 235

Pro Trp Asn Leu Asn Thr Thr Gly Asn Val Cys Gln Val Phe Ala Thr
            240                 245                 250

Glu Phe Ser Ala Val Thr Ser Met Ile Lys Asn Ala Gln Glu Ile Val
        255                 260                 265

Thr Gln Ala Gln Ser Leu Asn Asn Pro Gln Ser Asn Gln Asn Ala Pro
        270                 275                 280

Lys Asp Phe Asn Pro Tyr Thr Ser Ala Asp Arg Ala Phe Ala Gln Asn
285                 290                 295                 300

Met Leu Asn His Ala Gln Ala Gln Ala Lys Met Leu Glu Leu Ala Asp
                305                 310                 315

Gln Met Lys Lys Asp Leu Asn Thr Ile Pro Lys Gln Phe Ile Thr Asn
            320                 325                 330

Tyr Leu Ala Ala Cys Arg Asn Gly Gly Thr Leu Pro Asp Ala Gly
        335                 340                 345

Val Thr Ser Asn Thr Trp Gly Ala Gly Cys Ala Tyr Val Glu Glu Thr
        350                 355                 360

Ile Thr Ala Leu Asn Asn Ser Leu Ala His Phe Gly Thr Gln Ala Asp
365                 370                 375                 380

Gln Ile Lys Gln Ser Glu Leu Leu Ala Arg Thr Ile Leu Asp Phe Arg
                385                 390                 395

Gly Ser Leu Lys Asp Leu Asn Asn Thr Tyr Asn Ser Ile Thr Thr Thr
            400                 405                 410

Ala Ser Asn Thr Pro Asn Ser Pro Phe Leu Lys Asn Leu Ile Ser Gln
        415                 420                 425

Ser Thr Asn Pro Asn Asn Pro Gly Gly Leu Gln Ala Val Tyr Gln Val
        430                 435                 440

Asn Gln Ser Ala Tyr Ser Gln Leu Leu Ser Ala Thr Gln Glu Leu Gly
445                 450                 455                 460

His Asn Pro Phe Arg Arg Val Gly Leu Ile Ser Ser Gln Thr Asn Asn
                465                 470                 475

Gly Ala Met Asn Gly Ile Gly Val Gln Ile Gly Tyr Lys Gln Phe Phe
            480                 485                 490

Gly Glu Lys Arg Arg Trp Gly Leu Arg Tyr Tyr Gly Phe Phe Asp Tyr
        495                 500                 505

Asn His Ala Tyr Ile Lys Ser Ser Phe Phe Asn Ser Ala Ser Asp Val
        510                 515                 520

Phe Thr Tyr Gly Val Gly Thr Asp Val Leu Tyr Asn Phe Ile Asn Asp
525                 530                 535                 540
```

```
Lys Ala Thr Lys Asn Asn Lys Ile Ser Phe Gly Val Phe Gly Gly Ile
                545                 550                 555

Ala Leu Ala Gly Thr Ser Trp Leu Asn Ser Gln Tyr Val Asn Leu Ala
            560                 565                 570

Thr Phe Asn Asn Phe Tyr Ser Ala Lys Met Asn Val Ala Asn Phe Gln
        575                 580                 585

Phe Leu Phe Asn Leu Gly Leu Arg Met Asn Leu Ala Lys Asn Lys Lys
    590                 595                 600

Lys Ala Ser Asp His Val Ala Gln His Gly Val Glu Leu Gly Val Lys
605                 610                 615                 620

Ile Pro Thr Ile Asn Thr Asn Tyr Tyr Ser Leu Leu Gly Thr Gln Leu
                625                 630                 635

Gln Tyr Arg Arg Leu Tyr Ser Val Tyr Leu Asn Tyr Val Phe Ala Tyr
            640                 645                 650

<210> SEQ ID NO 11
<211> LENGTH: 2429
<212> TYPE: DNA
<213> ORGANISM: Helicobacter pylori
<220> FEATURE:
<221> NAME/KEY: CDS
<222> LOCATION: (205)...(2277)
<220> FEATURE:
<221> NAME/KEY: sig_peptide
<222> LOCATION: (205)...(259)

<400> SEQUENCE: 11
tgaaagaaga ctgattagtc tttcttttag gggcgattca agccttaaaa gccgggtcaa      60
aatccccatt tttcccaatt tttacaaaaa aaaaaaaaac aaaatctcta aaatttagag     120
ctaaaattag ccataaaatt ccatttattg cttataatat gaagtttctt tgtatcaaag     180
aaaaatctat taaaggaga aaac atg aaa aaa tcc ctc tta ctc tct ctt         231
                         Met Lys Lys Ser Leu Leu Leu Ser Leu
                             -15                 -10 tct ctc atc gct tcc tta tca aga gct gaa gat gac gga ttt tat acg      279
Ser Leu Ile Ala Ser Leu Ser Arg Ala Glu Asp Asp Gly Phe Tyr Thr
            -5                  1               5 agt gtg ggc tat cag atc ggt gaa gcg gtc caa caa gtg aaa aac aca      327
Ser Val Gly Tyr Gln Ile Gly Glu Ala Val Gln Gln Val Lys Asn Thr
        10                  15                  20 gga gca ttg caa aat ctt gca gac aga tac gat aac tta aac aac ctt      375
Gly Ala Leu Gln Asn Leu Ala Asp Arg Tyr Asp Asn Leu Asn Asn Leu
    25                  30                  35 tta aac caa tac aat tat tta aat tcc tta gtc aat tta gcc agc acg      423
Leu Asn Gln Tyr Asn Tyr Leu Asn Ser Leu Val Asn Leu Ala Ser Thr
40                  45                  50                  55 ccg agc gcg atc acc ggt gcg att gat aat tta agc tca agc gcg att      471
Pro Ser Ala Ile Thr Gly Ala Ile Asp Asn Leu Ser Ser Ser Ala Ile
                60                  65                  70 aac ctc act agc gcc acc acc act tcc ccc gcc tat caa gct gtg gct      519
Asn Leu Thr Ser Ala Thr Thr Thr Ser Pro Ala Tyr Gln Ala Val Ala
            75                  80                  85 tta gcg ctc aat gcc gct gtg ggc atg tgg caa gtc ata gcc ctt ttt      567
Leu Ala Leu Asn Ala Ala Val Gly Met Trp Gln Val Ile Ala Leu Phe
        90                  95                  100 att ggc tgt ggc cct ggc cct acc aat aat caa agc tat caa tcg ttt      615
Ile Gly Cys Gly Pro Gly Pro Thr Asn Asn Gln Ser Tyr Gln Ser Phe
    105                 110                 115 ggt aac aca cca gcc ctt aat ggg acc acc acc act tgc aat caa gca      663
Gly Asn Thr Pro Ala Leu Asn Gly Thr Thr Thr Thr Cys Asn Gln Ala
```

|   |   |   |   |   |   |   |   |   |   |   |   |   |   |   |   |     |
|---|---|---|---|---|---|---|---|---|---|---|---|---|---|---|---|-----|
| 120 |   |   |   |   | 125 |   |   |   |   | 130 |   |   |   |   | 135 |     |
| tat | ggg | aca | ggc | cct | aat | ggc | atc | cta | tct | att | gat | gaa | tac | caa | aaa | 711 |
| Tyr | Gly | Thr | Gly | Pro | Asn | Gly | Ile | Leu | Ser | Ile | Asp | Glu | Tyr | Gln | Lys |     |
|   |   |   |   | 140 |   |   |   |   | 145 |   |   |   |   | 150 |   |     |
| ctc | aac | caa | gct | tat | cag | atc | atc | caa | acc | gct | tta | aac | caa | aat | caa | 759 |
| Leu | Asn | Gln | Ala | Tyr | Gln | Ile | Ile | Gln | Thr | Ala | Leu | Asn | Gln | Asn | Gln |     |
|   |   |   |   | 155 |   |   |   |   | 160 |   |   |   |   | 165 |   |     |
| ggg | ggt | ggg | atg | cct | gcc | ttg | aat | gac | acc | acc | aaa | aca | ggg | gta | gtc | 807 |
| Gly | Gly | Gly | Met | Pro | Ala | Leu | Asn | Asp | Thr | Thr | Lys | Thr | Gly | Val | Val |     |
|   |   |   |   | 170 |   |   |   |   | 175 |   |   |   |   | 180 |   |     |
| aac | ata | caa | caa | acc | aat | tat | agg | acc | acc | aca | caa | aac | aat | atc | ata | 855 |
| Asn | Ile | Gln | Gln | Thr | Asn | Tyr | Arg | Thr | Thr | Thr | Gln | Asn | Asn | Ile | Ile |     |
|   |   |   |   | 185 |   |   |   |   | 190 |   |   |   |   | 195 |   |     |
| gag | cat | tat | tat | aca | gag | aat | ggg | aaa | gag | atc | cca | gtc | tct | tat | tca | 903 |
| Glu | His | Tyr | Tyr | Thr | Glu | Asn | Gly | Lys | Glu | Ile | Pro | Val | Ser | Tyr | Ser |     |
| 200 |   |   |   |   | 205 |   |   |   |   | 210 |   |   |   |   | 215 |     |
| ggc | gga | tca | tca | ttc | tcg | cct | aca | ata | caa | ttg | aca | tac | cat | aat | aac | 951 |
| Gly | Gly | Ser | Ser | Phe | Ser | Pro | Thr | Ile | Gln | Leu | Thr | Tyr | His | Asn | Asn |     |
|   |   |   |   | 220 |   |   |   |   | 225 |   |   |   |   | 230 |   |     |
| gct | gaa | aac | ctt | ttg | caa | caa | gcc | gcc | act | atc | atg | caa | gtc | ctt | att | 999 |
| Ala | Glu | Asn | Leu | Leu | Gln | Gln | Ala | Ala | Thr | Ile | Met | Gln | Val | Leu | Ile |     |
|   |   |   |   | 235 |   |   |   |   | 240 |   |   |   |   | 245 |   |     |
| act | caa | aag | ccg | cat | gtg | caa | acg | agc | aat | ggc | ggt | aaa | gcg | tgg | ggg | 1047 |
| Thr | Gln | Lys | Pro | His | Val | Gln | Thr | Ser | Asn | Gly | Gly | Lys | Ala | Trp | Gly |     |
|   |   |   |   | 250 |   |   |   |   | 255 |   |   |   |   | 260 |   |     |
| ttg | agt | tct | acg | cct | ggg | aat | gtg | atg | gat | att | ttt | ggt | cct | tct | ttt | 1095 |
| Leu | Ser | Ser | Thr | Pro | Gly | Asn | Val | Met | Asp | Ile | Phe | Gly | Pro | Ser | Phe |     |
| 265 |   |   |   |   | 270 |   |   |   |   | 275 |   |   |   |   |   |     |
| aac | gct | att | aat | gag | atg | att | aaa | aac | gct | caa | aca | gcc | cta | gca | aaa | 1143 |
| Asn | Ala | Ile | Asn | Glu | Met | Ile | Lys | Asn | Ala | Gln | Thr | Ala | Leu | Ala | Lys |     |
| 280 |   |   |   |   | 285 |   |   |   |   | 290 |   |   |   |   | 295 |     |
| acc | caa | cag | ctt | aac | gct | aat | gaa | aac | gcc | caa | atc | acg | caa | ccc | aac | 1191 |
| Thr | Gln | Gln | Leu | Asn | Ala | Asn | Glu | Asn | Ala | Gln | Ile | Thr | Gln | Pro | Asn |     |
|   |   |   |   | 300 |   |   |   |   | 305 |   |   |   |   | 310 |   |     |
| aat | ttc | aac | ccc | tac | acc | tct | aaa | gac | aaa | ggg | ttc | gct | caa | gaa | atg | 1239 |
| Asn | Phe | Asn | Pro | Tyr | Thr | Ser | Lys | Asp | Lys | Gly | Phe | Ala | Gln | Glu | Met |     |
|   |   |   |   | 315 |   |   |   |   | 320 |   |   |   |   | 325 |   |     |
| ctc | aat | aga | gct | gaa | gct | caa | gca | gag | att | tta | aat | tta | gct | aag | caa | 1287 |
| Leu | Asn | Arg | Ala | Glu | Ala | Gln | Ala | Glu | Ile | Leu | Asn | Leu | Ala | Lys | Gln |     |
|   |   |   |   | 330 |   |   |   |   | 335 |   |   |   |   | 340 |   |     |
| gta | gcg | aac | aat | ttc | cac | agc | att | caa | ggg | cct | att | caa | ggg | gat | tta | 1335 |
| Val | Ala | Asn | Asn | Phe | His | Ser | Ile | Gln | Gly | Pro | Ile | Gln | Gly | Asp | Leu |     |
|   |   |   |   | 345 |   |   |   |   | 350 |   |   |   |   | 355 |   |     |
| gaa | gaa | tgt | aaa | gca | gga | tcg | gct | ggc | gtg | atc | act | aat | aac | act | tgg | 1383 |
| Glu | Glu | Cys | Lys | Ala | Gly | Ser | Ala | Gly | Val | Ile | Thr | Asn | Asn | Thr | Trp |     |
| 360 |   |   |   |   | 365 |   |   |   |   | 370 |   |   |   |   | 375 |     |
| ggt | tca | ggt | tgc | gcg | ttt | gtg | aaa | gaa | act | tta | aac | tct | tta | gag | caa | 1431 |
| Gly | Ser | Gly | Cys | Ala | Phe | Val | Lys | Glu | Thr | Leu | Asn | Ser | Leu | Glu | Gln |     |
|   |   |   |   | 380 |   |   |   |   | 385 |   |   |   |   | 390 |   |     |
| cac | acc | gct | tat | tac | ggc | aac | cag | gtc | aat | cag | gat | agg | gct | ttg | gct | 1479 |
| His | Thr | Ala | Tyr | Tyr | Gly | Asn | Gln | Val | Asn | Gln | Asp | Arg | Ala | Leu | Ala |     |
|   |   |   |   | 395 |   |   |   |   | 400 |   |   |   |   | 405 |   |     |
| caa | acc | att | ttg | aat | ttt | aaa | gaa | gcc | ctt | aac | acc | ctg | aat | aaa | gac | 1527 |
| Gln | Thr | Ile | Leu | Asn | Phe | Lys | Glu | Ala | Leu | Asn | Thr | Leu | Asn | Lys | Asp |     |
|   |   |   |   | 410 |   |   |   |   | 415 |   |   |   |   | 420 |   |     |
| tca | aaa | gcg | atc | aat | agc | ggt | atc | tcc | aac | ttg | cct | aac | gct | aaa | tct | 1575 |
| Ser | Lys | Ala | Ile | Asn | Ser | Gly | Ile | Ser | Asn | Leu | Pro | Asn | Ala | Lys | Ser |     |
|   |   |   |   | 425 |   |   |   |   | 430 |   |   |   |   | 435 |   |     |
| ctt | caa | aac | atg | acg | cat | gcc | act | caa | aac | cct | aat | tcc | cca | gaa | ggt | 1623 |

```
                                                  -continued

Leu Gln Asn Met Thr His Ala Thr Gln Asn Pro Asn Ser Pro Glu Gly
440                 445                 450                 455 ctg ctc act tat tct ttg gat tca agc aaa tac aac cag ctc caa acc    1671
Leu Leu Thr Tyr Ser Leu Asp Ser Ser Lys Tyr Asn Gln Leu Gln Thr
                460                 465                 470 atc gcg caa gaa ttg ggc aaa aac cct ttc agg cgc ttt ggc gtg att    1719
Ile Ala Gln Glu Leu Gly Lys Asn Pro Phe Arg Arg Phe Gly Val Ile
            475                 480                 485 gac ttt caa aac aac aac ggc gca atg aac ggg atc ggc gtg caa gtg    1767
Asp Phe Gln Asn Asn Asn Gly Ala Met Asn Gly Ile Gly Val Gln Val
        490                 495                 500 ggt tat aaa caa ttc ttt ggt aaa aaa agg aat tgg ggg tta agg tat    1815
Gly Tyr Lys Gln Phe Phe Gly Lys Lys Arg Asn Trp Gly Leu Arg Tyr
    505                 510                 515 tat ggt ttc ttt gat tat aac cat gct tat atc aaa tct aat ttt ttc    1863
Tyr Gly Phe Phe Asp Tyr Asn His Ala Tyr Ile Lys Ser Asn Phe Phe
520                 525                 530                 535 aac tcc gct tct gat gtg tgg act tat ggg gtg ggt atg gac gct ctc    1911
Asn Ser Ala Ser Asp Val Trp Thr Tyr Gly Val Gly Met Asp Ala Leu
                540                 545                 550 tat aac ttc atc aac gat aaa aac acc aac ttt tta ggc aag aac aac    1959
Tyr Asn Phe Ile Asn Asp Lys Asn Thr Asn Phe Leu Gly Lys Asn Asn
            555                 560                 565 aag ctt tca gta ggg ctt ttt gga ggc ttt gcg tta gcc ggg act tcg    2007
Lys Leu Ser Val Gly Leu Phe Gly Gly Phe Ala Leu Ala Gly Thr Ser
        570                 575                 580 tgg ctt aat tcc caa caa gtg aat ttg acc atg atg aat ggc att tat    2055
Trp Leu Asn Ser Gln Gln Val Asn Leu Thr Met Met Asn Gly Ile Tyr
    585                 590                 595 aac gct aat gtc agc act tct aac ttc caa ttt ttg ttt gat tta ggc    2103
Asn Ala Asn Val Ser Thr Ser Asn Phe Gln Phe Leu Phe Asp Leu Gly
600                 605                 610                 615 ttg aga atg aac ctc gct agg cct aag aaa aaa gac agc gat cat gcc    2151
Leu Arg Met Asn Leu Ala Arg Pro Lys Lys Lys Asp Ser Asp His Ala
                620                 625                 630 gct cag cat ggc att gaa cta ggt ttt aag atc ccc acg atc aac acc    2199
Ala Gln His Gly Ile Glu Leu Gly Phe Lys Ile Pro Thr Ile Asn Thr
            635                 640                 645 aac tat tat tct ttc atg ggc gct aaa cta gaa tac aga agg atg tat    2247
Asn Tyr Tyr Ser Phe Met Gly Ala Lys Leu Glu Tyr Arg Arg Met Tyr
        650                 655                 660 agc ctt ttt ctc aat tat gtg ttt gct tac taaaaattct ttttgaaccc      2297
Ser Leu Phe Leu Asn Tyr Val Phe Ala Tyr
    665                 670 ctctttttt gggggagtgt tgcaaaaatg ccccctatt tgcttgtgag ttttggttaa    2357
aattttagtt acccacgctt aaaaagcgcc aagcctttta cacacaactc ctttaatttt  2417 gttttttaaga aa                                                      2429

<210> SEQ ID NO 12
<211> LENGTH: 691
<212> TYPE: PRT
<213> ORGANISM: Helicobacter pylori
<220> FEATURE:
<221> NAME/KEY: SIGNAL
<222> LOCATION: (1)...(18)

<400> SEQUENCE: 12

Met Lys Lys Ser Leu Leu Leu Ser Leu Ser Leu Ile Ala Ser Leu Ser
                -15                 -10                 -5
```

-continued

```
Arg Ala Glu Asp Asp Gly Phe Tyr Thr Ser Val Gly Tyr Gln Ile Gly
            1               5                   10

Glu Ala Val Gln Gln Val Lys Asn Thr Gly Ala Leu Gln Asn Leu Ala
 15              20                  25                      30

Asp Arg Tyr Asp Asn Leu Asn Leu Leu Asn Gln Tyr Asn Tyr Leu
                35              40                  45

Asn Ser Leu Val Asn Leu Ala Ser Thr Pro Ser Ala Ile Thr Gly Ala
             50                  55                  60

Ile Asp Asn Leu Ser Ser Ser Ala Ile Asn Leu Thr Ser Ala Thr Thr
         65                  70              75

Thr Ser Pro Ala Tyr Gln Ala Val Ala Leu Ala Leu Asn Ala Ala Val
         80              85                  90

Gly Met Trp Gln Val Ile Ala Leu Phe Ile Gly Cys Gly Pro Gly Pro
 95                 100                 105                 110

Thr Asn Asn Gln Ser Tyr Gln Ser Phe Gly Asn Thr Pro Ala Leu Asn
                115                 120                 125

Gly Thr Thr Thr Thr Cys Asn Gln Ala Tyr Gly Thr Gly Pro Asn Gly
             130                 135                 140

Ile Leu Ser Ile Asp Glu Tyr Gln Lys Leu Asn Gln Ala Tyr Gln Ile
         145                 150                 155

Ile Gln Thr Ala Leu Asn Gln Asn Gly Gly Met Pro Ala Leu
         160                 165                 170

Asn Asp Thr Thr Lys Thr Gly Val Val Asn Ile Gln Gln Thr Asn Tyr
175                 180                 185                     190

Arg Thr Thr Thr Gln Asn Asn Ile Ile Glu His Tyr Tyr Thr Glu Asn
                195                 200                 205

Gly Lys Glu Ile Pro Val Ser Tyr Ser Gly Ser Ser Phe Ser Pro
                210                 215                 220

Thr Ile Gln Leu Thr Tyr His Asn Asn Ala Glu Asn Leu Leu Gln Gln
                225                 230                 235

Ala Ala Thr Ile Met Gln Val Leu Ile Thr Gln Lys Pro His Val Gln
         240                 245                 250

Thr Ser Asn Gly Gly Lys Ala Trp Gly Leu Ser Ser Thr Pro Gly Asn
255                 260                 265                 270

Val Met Asp Ile Phe Gly Pro Ser Phe Asn Ala Ile Asn Glu Met Ile
                275                 280                 285

Lys Asn Ala Gln Thr Ala Leu Ala Lys Thr Gln Gln Leu Asn Ala Asn
                290                 295                 300

Glu Asn Ala Gln Ile Thr Gln Pro Asn Asn Phe Asn Pro Tyr Thr Ser
                305                 310                 315

Lys Asp Lys Gly Phe Ala Gln Glu Met Leu Asn Arg Ala Glu Ala Gln
         320                 325                 330

Ala Glu Ile Leu Asn Leu Ala Lys Gln Val Ala Asn Asn Phe His Ser
335                 340                 345                 350

Ile Gln Gly Pro Ile Gln Gly Asp Leu Glu Glu Cys Lys Ala Gly Ser
                355                 360                 365

Ala Gly Val Ile Thr Asn Asn Thr Trp Gly Ser Gly Cys Ala Phe Val
             370                 375                 380

Lys Glu Thr Leu Asn Ser Leu Glu Gln His Thr Ala Tyr Tyr Gly Asn
         385                 390                 395

Gln Val Asn Gln Asp Arg Ala Leu Ala Gln Thr Ile Leu Asn Phe Lys
         400                 405                 410

Glu Ala Leu Asn Thr Leu Asn Lys Asp Ser Lys Ala Ile Asn Ser Gly
```

```
                 415                 420                 425                 430
Ile Ser Asn Leu Pro Asn Ala Lys Ser Leu Gln Asn Met Thr His Ala
                435                 440                 445

Thr Gln Asn Pro Asn Ser Pro Glu Gly Leu Leu Thr Tyr Ser Leu Asp
            450                 455                 460

Ser Ser Lys Tyr Asn Gln Leu Gln Thr Ile Ala Gln Glu Leu Gly Lys
        465                 470                 475

Asn Pro Phe Arg Arg Phe Gly Val Ile Asp Phe Gln Asn Asn Asn Gly
    480                 485                 490

Ala Met Asn Gly Ile Gly Val Gln Val Gly Tyr Lys Gln Phe Phe Gly
495                 500                 505                 510

Lys Lys Arg Asn Trp Gly Leu Arg Tyr Tyr Gly Phe Phe Asp Tyr Asn
                515                 520                 525

His Ala Tyr Ile Lys Ser Asn Phe Phe Asn Ser Ala Ser Asp Val Trp
            530                 535                 540

Thr Tyr Gly Val Gly Met Asp Ala Leu Tyr Asn Phe Ile Asn Asp Lys
        545                 550                 555

Asn Thr Asn Phe Leu Gly Lys Asn Asn Lys Leu Ser Val Gly Leu Phe
    560                 565                 570

Gly Gly Phe Ala Leu Ala Gly Thr Ser Trp Leu Asn Ser Gln Gln Val
575                 580                 585                 590

Asn Leu Thr Met Met Asn Gly Ile Tyr Asn Ala Asn Val Ser Thr Ser
                595                 600                 605

Asn Phe Gln Phe Leu Phe Asp Leu Gly Leu Arg Met Asn Leu Ala Arg
            610                 615                 620

Pro Lys Lys Lys Asp Ser Asp His Ala Ala Gln His Gly Ile Glu Leu
        625                 630                 635

Gly Phe Lys Ile Pro Thr Ile Asn Thr Asn Tyr Tyr Ser Phe Met Gly
    640                 645                 650

Ala Lys Leu Glu Tyr Arg Arg Met Tyr Ser Leu Phe Leu Asn Tyr Val
655                 660                 665                 670

Phe Ala Tyr

<210> SEQ ID NO 13
<211> LENGTH: 2270
<212> TYPE: DNA
<213> ORGANISM: Helicobacter pylori
<220> FEATURE:
<221> NAME/KEY: CDS
<222> LOCATION: (130)...(2049)
<220> FEATURE:
<221> NAME/KEY: sig_peptide
<222> LOCATION: (130)...(193)

<400> SEQUENCE: 13
attgagcgca tcaaaacacc ctaaaacttt tttgaaatcc aataaattta tgttataatt      60
aaacgcattg taaataaatt ctcattttga tacatttta caataaaaca ttactttaag     120 gaacatctt atg aaa aaa acg aaa aaa acg att ctg ctt tct cta act ctc    171
           Met Lys Lys Thr Lys Lys Thr Ile Leu Leu Ser Leu Thr Leu
              -20                 -15                 -10 gcg gcg tca ttg ctc cat gct gaa gac aac ggc gtt ttt tta agc gtg     219
Ala Ala Ser Leu Leu His Ala Glu Asp Asn Gly Val Phe Leu Ser Val
        -5                   1                   5 ggt tat caa atc ggt gaa gcg gtt caa aaa gtg aaa aac gcc gac aag     267
Gly Tyr Gln Ile Gly Glu Ala Val Gln Lys Val Lys Asn Ala Asp Lys
 10                  15                  20                  25
```

-continued

| | |
|---|---|
| gtg caa aaa ctt tca gac act tat gaa caa tta agc cgg ctt tta acc<br>Val Gln Lys Leu Ser Asp Thr Tyr Glu Gln Leu Ser Arg Leu Leu Thr<br>　　　　　　30　　　　　　　　　　35　　　　　　　　　　40 | 315 |
| aac gat aat ggc aca aac tca aag aca agc gcg caa atc aac caa gcg<br>Asn Asp Asn Gly Thr Asn Ser Lys Thr Ser Ala Gln Ile Asn Gln Ala<br>　　　　45　　　　　　　　　　50　　　　　　　　　　55 | 363 |
| gtt aat aat ttg aac gaa cgc gca aaa act tta gcc ggt ggg aca acc<br>Val Asn Asn Leu Asn Glu Arg Ala Lys Thr Leu Ala Gly Gly Thr Thr<br>　　60　　　　　　　　　　65　　　　　　　　　　70 | 411 |
| aat tcc cct gcc tat caa gcc acg ctt tta gcg ttg aga tcg gtg tta<br>Asn Ser Pro Ala Tyr Gln Ala Thr Leu Leu Ala Leu Arg Ser Val Leu<br>75　　　　　　　　　　80　　　　　　　　　　85 | 459 |
| ggg cta tgg aat agc atg ggt tat gcg gtc ata tgc gga ggt tat acc<br>Gly Leu Trp Asn Ser Met Gly Tyr Ala Val Ile Cys Gly Gly Tyr Thr<br>90　　　　　　　　　　95　　　　　　　　　　100　　　　　　　　　　105 | 507 |
| aaa agt cca ggc gaa aac aat caa aaa gat ttc cac tac acc gat gag<br>Lys Ser Pro Gly Glu Asn Asn Gln Lys Asp Phe His Tyr Thr Asp Glu<br>　　　　　　　　　　110　　　　　　　　　　115　　　　　　　　　　120 | 555 |
| aat ggc aat ggc act aca atc aat tgc ggt ggg agc aca aat agt aat<br>Asn Gly Asn Gly Thr Thr Ile Asn Cys Gly Gly Ser Thr Asn Ser Asn<br>　　　　　　125　　　　　　　　　　130　　　　　　　　　　135 | 603 |
| ggc act cat agt tct agt ggc aca aat aca tta aaa gca gac aaa aat<br>Gly Thr His Ser Ser Ser Gly Thr Asn Thr Leu Lys Ala Asp Lys Asn<br>　　　　140　　　　　　　　　　145　　　　　　　　　　150 | 651 |
| gtt tct cta tct att gag caa tat gaa aaa atc cat gaa gct tat cag<br>Val Ser Leu Ser Ile Glu Gln Tyr Glu Lys Ile His Glu Ala Tyr Gln<br>155　　　　　　　　　　160　　　　　　　　　　165 | 699 |
| att ctt tca aaa gct tta aaa caa gcc ggg ctt gct cct tta aat agc<br>Ile Leu Ser Lys Ala Leu Lys Gln Ala Gly Leu Ala Pro Leu Asn Ser<br>170　　　　　　　　　　175　　　　　　　　　　180　　　　　　　　　　185 | 747 |
| aaa ggg gaa aag tta gaa gcg cat gta acc aca tca aaa cca gaa aat<br>Lys Gly Glu Lys Leu Glu Ala His Val Thr Thr Ser Lys Pro Glu Asn<br>　　　　　　　　　　190　　　　　　　　　　195　　　　　　　　　　200 | 795 |
| aat agt caa act aaa acg aca act tct gtt att gat acg act aat gat<br>Asn Ser Gln Thr Lys Thr Thr Thr Ser Val Ile Asp Thr Thr Asn Asp<br>　　　　　　205　　　　　　　　　　210　　　　　　　　　　215 | 843 |
| gcg caa aat ctt ttg act caa gcg caa acg att gtc aat acc ctt aaa<br>Ala Gln Asn Leu Leu Thr Gln Ala Gln Thr Ile Val Asn Thr Leu Lys<br>　　　　220　　　　　　　　　　225　　　　　　　　　　230 | 891 |
| gat tat tgc ccc atg ttg ata gcg aaa tct agt agt gaa agt agt ggc<br>Asp Tyr Cys Pro Met Leu Ile Ala Lys Ser Ser Ser Glu Ser Ser Gly<br>235　　　　　　　　　　240　　　　　　　　　　245 | 939 |
| gca gct act aca aac gcc cct tca tgg caa aca gcc ggt ggc ggc aaa<br>Ala Ala Thr Thr Asn Ala Pro Ser Trp Gln Thr Ala Gly Gly Gly Lys<br>250　　　　　　　　　　255　　　　　　　　　　260　　　　　　　　　　265 | 987 |
| aat tca tgt gcg act ttt ggt gcg gag ttt agt gcc gct tca gac atg<br>Asn Ser Cys Ala Thr Phe Gly Ala Glu Phe Ser Ala Ala Ser Asp Met<br>　　　　　　　　　　270　　　　　　　　　　275　　　　　　　　　　280 | 1035 |
| att aat aat gcg caa aaa atc gtt caa gaa acc caa caa ctc agc gcc<br>Ile Asn Asn Ala Gln Lys Ile Val Gln Glu Thr Gln Gln Leu Ser Ala<br>　　　　　　285　　　　　　　　　　290　　　　　　　　　　295 | 1083 |
| aac caa cca aaa aat atc aca caa ccc cat aat ctc aac ctt aac acc<br>Asn Gln Pro Lys Asn Ile Thr Gln Pro His Asn Leu Asn Leu Asn Thr<br>　　　　300　　　　　　　　　　305　　　　　　　　　　310 | 1131 |
| cct agc agt ctt acg gct tta gct caa aaa atg ctc aaa aat gcg caa<br>Pro Ser Ser Leu Thr Ala Leu Ala Gln Lys Met Leu Lys Asn Ala Gln<br>315　　　　　　　　　　320　　　　　　　　　　325 | 1179 |
| tct caa gca gaa att tta aaa cta gcc aat caa gtg gag agc gat ttt<br>Ser Gln Ala Glu Ile Leu Lys Leu Ala Asn Gln Val Glu Ser Asp Phe<br>330　　　　　　　　　　335　　　　　　　　　　340　　　　　　　　　　345 | 1227 |

-continued

| | |
|---|---|
| aac aaa ctt tct tca ggc cat ctt aaa gac tac ata ggg aaa tgc gat<br>Asn Lys Leu Ser Ser Gly His Leu Lys Asp Tyr Ile Gly Lys Cys Asp<br>350             355             360 | 1275 |
| gcg agc gct ata agc agt gcg aat atg aca atg caa aat caa aag aac<br>Ala Ser Ala Ile Ser Ser Ala Asn Met Thr Met Gln Asn Gln Lys Asn<br>    365             370             375 | 1323 |
| aat tgg ggg aac ggg tgt gct ggc gtg gaa gaa act ctg tct tca tta<br>Asn Trp Gly Asn Gly Cys Ala Gly Val Glu Glu Thr Leu Ser Ser Leu<br>        380             385             390 | 1371 |
| aaa aca agt gcc gct gat ttt aac aac caa acg cca caa atc aat caa<br>Lys Thr Ser Ala Ala Asp Phe Asn Asn Gln Thr Pro Gln Ile Asn Gln<br>    395             400             405 | 1419 |
| gcg caa aac cta gcc aac acc ctt att caa gaa ctt ggc aac aac cct<br>Ala Gln Asn Leu Ala Asn Thr Leu Ile Gln Glu Leu Gly Asn Asn Pro<br>410             415             420             425 | 1467 |
| ttt agg aat atg ggc atg atc gct tct tca acc acg aat aac ggc gcc<br>Phe Arg Asn Met Gly Met Ile Ala Ser Ser Thr Thr Asn Asn Gly Ala<br>            430             435             440 | 1515 |
| ttg aat ggc ctt ggg gtg caa gtg ggt tat aag caa ttt ttt ggg gaa<br>Leu Asn Gly Leu Gly Val Gln Val Gly Tyr Lys Gln Phe Phe Gly Glu<br>        445             450             455 | 1563 |
| aag aaa aga tgg ggg tta agg tat tat ggt ttc ttt gat tac aac cac<br>Lys Lys Arg Trp Gly Leu Arg Tyr Tyr Gly Phe Phe Asp Tyr Asn His<br>460             465             470 | 1611 |
| gcc tat atc aaa tcc aat ttc ttt aac tcg gct tct gat gtg tgg act<br>Ala Tyr Ile Lys Ser Asn Phe Phe Asn Ser Ala Ser Asp Val Trp Thr<br>    475             480             485 | 1659 |
| tat ggg gtg ggc agc gat tta ttg ttt aat ttc atc aat gat aaa aac<br>Tyr Gly Val Gly Ser Asp Leu Leu Phe Asn Phe Ile Asn Asp Lys Asn<br>490             495             500             505 | 1707 |
| acc aac ttt tta ggc aag aat aac aag att tca gtg gga ttt ttt gga<br>Thr Asn Phe Leu Gly Lys Asn Asn Lys Ile Ser Val Gly Phe Phe Gly<br>            510             515             520 | 1755 |
| ggt atc gcc tta gca ggg act tca tgg ctt aat tct caa ttc gtg aat<br>Gly Ile Ala Leu Ala Gly Thr Ser Trp Leu Asn Ser Gln Phe Val Asn<br>        525             530             535 | 1803 |
| tta aaa acc atc agc aat gtt tat agc gct aaa gtg aat acg gct aac<br>Leu Lys Thr Ile Ser Asn Val Tyr Ser Ala Lys Val Asn Thr Ala Asn<br>    540             545             550 | 1851 |
| ttc caa ttt tta ttc aat ttg ggc ttg aga acc aat ctc gct aga cct<br>Phe Gln Phe Leu Phe Asn Leu Gly Leu Arg Thr Asn Leu Ala Arg Pro<br>555             560             565 | 1899 |
| aag aaa aaa gat agt cat cat gcg gct caa cat ggc atg gaa ttg ggc<br>Lys Lys Lys Asp Ser His His Ala Ala Gln His Gly Met Glu Leu Gly<br>570             575             580             585 | 1947 |
| gtg aaa atc cct acc att aac acg aat tat tat tct ttt cta gac act<br>Val Lys Ile Pro Thr Ile Asn Thr Asn Tyr Tyr Ser Phe Leu Asp Thr<br>            590             595             600 | 1995 |
| aaa cta gaa tat cga agg ctt tat agc gtg tat ctc aat tat gtg ttt<br>Lys Leu Glu Tyr Arg Arg Leu Tyr Ser Val Tyr Leu Asn Tyr Val Phe<br>        605             610             615 | 2043 |
| gcc tat taaaaaccct ctttttaaaa aaggggggggc tttaaaaaac ctctaaagat<br>Ala Tyr | 2099 |
| aaaaattttc aaaaaacaat cattaaaccc taaaaagaa attttaaggt ataatgcttt | 2159 |
| cgccattttt aattttccat ggcaaactcc tttttagaat ttatccccat aatcgctctt | 2219 |
| atggggcgtt tgttttgcaa caatcttttc gaaactatcc aacaagcttt a | 2270 |

<210> SEQ ID NO 14
<211> LENGTH: 640
<212> TYPE: PRT
<213> ORGANISM: Helicobacter pylori
<220> FEATURE:
<221> NAME/KEY: SIGNAL
<222> LOCATION: (1)...(21)

<400> SEQUENCE: 14

```
Met Lys Lys Thr Lys Lys Thr Ile Leu Leu Ser Leu Thr Leu Ala Ala
    -20              -15                 -10
Ser Leu Leu His Ala Glu Asp Asn Gly Val Phe Leu Ser Val Gly Tyr
 -5               1                5                   10
Gln Ile Gly Glu Ala Val Gln Lys Val Lys Asn Ala Asp Lys Val Gln
            15                  20                  25
Lys Leu Ser Asp Thr Tyr Glu Gln Leu Ser Arg Leu Leu Thr Asn Asp
             30                  35                  40
Asn Gly Thr Asn Ser Lys Thr Ser Ala Gln Ile Asn Gln Ala Val Asn
         45                  50                  55
Asn Leu Asn Glu Arg Ala Lys Thr Leu Ala Gly Gly Thr Thr Asn Ser
 60                  65                  70                  75
Pro Ala Tyr Gln Ala Thr Leu Leu Ala Leu Arg Ser Val Leu Gly Leu
                 80                  85                  90
Trp Asn Ser Met Gly Tyr Ala Val Ile Cys Gly Gly Tyr Thr Lys Ser
                 95                  100                 105
Pro Gly Glu Asn Asn Gln Lys Asp Phe His Tyr Thr Asp Glu Asn Gly
             110                 115                 120
Asn Gly Thr Thr Ile Asn Cys Gly Gly Ser Thr Asn Ser Asn Gly Thr
         125                 130                 135
His Ser Ser Ser Gly Thr Asn Thr Leu Lys Ala Asp Lys Asn Val Ser
140                 145                 150                 155
Leu Ser Ile Glu Gln Tyr Glu Lys Ile His Glu Ala Tyr Gln Ile Leu
                 160                 165                 170
Ser Lys Ala Leu Lys Gln Ala Gly Leu Ala Pro Leu Asn Ser Lys Gly
             175                 180                 185
Glu Lys Leu Glu Ala His Val Thr Thr Ser Lys Pro Glu Asn Asn Ser
         190                 195                 200
Gln Thr Lys Thr Thr Thr Ser Val Ile Asp Thr Thr Asn Asp Ala Gln
     205                 210                 215
Asn Leu Leu Thr Gln Ala Gln Thr Ile Val Asn Thr Leu Lys Asp Tyr
220                 225                 230                 235
Cys Pro Met Leu Ile Ala Lys Ser Ser Glu Ser Ser Gly Ala Ala
                 240                 245                 250
Thr Thr Asn Ala Pro Ser Trp Gln Thr Ala Gly Gly Lys Asn Ser
             255                 260                 265
Cys Ala Thr Phe Gly Ala Glu Phe Ser Ala Ala Ser Asp Met Ile Asn
             270                 275                 280
Asn Ala Gln Lys Ile Val Gln Glu Thr Gln Gln Leu Ser Ala Asn Gln
         285                 290                 295
Pro Lys Asn Ile Thr Gln Pro His Asn Leu Asn Leu Asn Thr Pro Ser
300                 305                 310                 315
Ser Leu Thr Ala Leu Ala Gln Lys Met Leu Lys Asn Ala Gln Ser Gln
                 320                 325                 330
Ala Glu Ile Leu Lys Leu Ala Asn Gln Val Glu Ser Asp Phe Asn Lys
             335                 340                 345
```

```
Leu Ser Ser Gly His Leu Lys Asp Tyr Ile Gly Lys Cys Asp Ala Ser
        350                 355                 360

Ala Ile Ser Ser Ala Asn Met Thr Met Gln Asn Gln Lys Asn Asn Trp
    365                 370                 375

Gly Asn Gly Cys Ala Gly Val Glu Glu Thr Leu Ser Ser Leu Lys Thr
380                 385                 390                 395

Ser Ala Ala Asp Phe Asn Asn Gln Thr Pro Gln Ile Asn Gln Ala Gln
                400                 405                 410

Asn Leu Ala Asn Thr Leu Ile Gln Glu Leu Gly Asn Asn Pro Phe Arg
            415                 420                 425

Asn Met Gly Met Ile Ala Ser Thr Thr Asn Asn Gly Ala Leu Asn
                430                 435                 440

Gly Leu Gly Val Gln Val Gly Tyr Lys Gln Phe Phe Gly Glu Lys Lys
    445                 450                 455

Arg Trp Gly Leu Arg Tyr Tyr Gly Phe Phe Asp Tyr Asn His Ala Tyr
460                 465                 470                 475

Ile Lys Ser Asn Phe Phe Asn Ser Ala Ser Asp Val Trp Thr Tyr Gly
                480                 485                 490

Val Gly Ser Asp Leu Leu Phe Asn Phe Ile Asn Asp Lys Asn Thr Asn
                495                 500                 505

Phe Leu Gly Lys Asn Asn Lys Ile Ser Val Gly Phe Phe Gly Gly Ile
        510                 515                 520

Ala Leu Ala Gly Thr Ser Trp Leu Asn Ser Gln Phe Val Asn Leu Lys
    525                 530                 535

Thr Ile Ser Asn Val Tyr Ser Ala Lys Val Asn Thr Ala Asn Phe Gln
540                 545                 550                 555

Phe Leu Phe Asn Leu Gly Leu Arg Thr Asn Leu Ala Arg Pro Lys Lys
                560                 565                 570

Lys Asp Ser His His Ala Ala Gln His Gly Met Glu Leu Gly Val Lys
            575                 580                 585

Ile Pro Thr Ile Asn Thr Asn Tyr Tyr Ser Phe Leu Asp Thr Lys Leu
        590                 595                 600

Glu Tyr Arg Arg Leu Tyr Ser Val Tyr Leu Asn Tyr Val Phe Ala Tyr
        605                 610                 615

<210> SEQ ID NO 15
<211> LENGTH: 2248
<212> TYPE: DNA
<213> ORGANISM: Helicobacter pylori
<220> FEATURE:
<221> NAME/KEY: CDS
<222> LOCATION: (173)...(2128)
<220> FEATURE:
<221> NAME/KEY: sig_peptide
<222> LOCATION: (173)...(224)

<400> SEQUENCE: 15
tggttttatc gttacaaaat tcaacatttc aaagataaat aagttaaaat accccaaaat      60
cttttttttt tttttgaaat ccaatcaatt tatagtaaaa ttaggttcat tgtaaatata     120
ttatcacttc atgatattct tacaacaaaa acattacttt aaggaacatt tt atg aaa     178
                                                          Met Lys aag aca att ctg ctc tct ctc tct gct tca tcg ctc ttg cac gct gaa     226
Lys Thr Ile Leu Leu Ser Leu Ser Ala Ser Ser Leu Leu His Ala Glu
    -15             -10                 -5                  1 gac aac ggc ttt ttt gtg agc gcc ggc tat caa atc ggc gaa gcg gtg     274
Asp Asn Gly Phe Phe Val Ser Ala Gly Tyr Gln Ile Gly Glu Ala Val
            5                   10                  15
```

```
caa atg gtc aaa aac acc ggt gaa ttg aaa aac ttg aac gaa aaa tac    322
Gln Met Val Lys Asn Thr Gly Glu Leu Lys Asn Leu Asn Glu Lys Tyr
        20                  25                  30 gag caa tta agc cag tat tta aat caa gtg gct tcg ttg aag caa agc    370
Glu Gln Leu Ser Gln Tyr Leu Asn Gln Val Ala Ser Leu Lys Gln Ser
 35                  40                  45 att caa aac gcc aac aac att gag ctg gtc aat agc tct tta aac tat    418
Ile Gln Asn Ala Asn Asn Ile Glu Leu Val Asn Ser Ser Leu Asn Tyr
 50                  55                  60                  65 tta aaa agc ttt acc aac aac aac tat aac agc acc acc caa tcg ccc    466
Leu Lys Ser Phe Thr Asn Asn Asn Tyr Asn Ser Thr Thr Gln Ser Pro
                 70                  75                  80 atc ttt aat gcc gtg caa gcc gtt atc act tcg gta ttg ggt ttt tgg    514
Ile Phe Asn Ala Val Gln Ala Val Ile Thr Ser Val Leu Gly Phe Trp
             85                  90                  95 agt ctt tat gcg ggg aat tac ttc act ttt ttt gtg ggt aaa aag gtg    562
Ser Leu Tyr Ala Gly Asn Tyr Phe Thr Phe Phe Val Gly Lys Lys Val
                100                 105                 110 ggt gat agt ggg caa ccc gct agt gtc cag ggt aac cct cct ttt aaa    610
Gly Asp Ser Gly Gln Pro Ala Ser Val Gln Gly Asn Pro Pro Phe Lys
            115                 120                 125 acg att ata gag aac tgc tca gga att gaa aac tgc gct atg gat caa    658
Thr Ile Ile Glu Asn Cys Ser Gly Ile Glu Asn Cys Ala Met Asp Gln
130                 135                 140                 145 acc act tat gat aag atg aaa aaa ctc gct gaa gac ctc caa gcg gct    706
Thr Thr Tyr Asp Lys Met Lys Lys Leu Ala Glu Asp Leu Gln Ala Ala
                150                 155                 160 caa aca aac tct gcc act aaa ggc aac aat ctt tgc gct tta tcc ggg    754
Gln Thr Asn Ser Ala Thr Lys Gly Asn Asn Leu Cys Ala Leu Ser Gly
            165                 170                 175 tgt gct gca aca gac tca aca tca aac cca cca aac tca acc gtg agc    802
Cys Ala Ala Thr Asp Ser Thr Ser Asn Pro Pro Asn Ser Thr Val Ser
        180                 185                 190 aac gct ctt aat ttg gcg caa cag ctt atg gat tta atc gca aac act    850
Asn Ala Leu Asn Leu Ala Gln Gln Leu Met Asp Leu Ile Ala Asn Thr
    195                 200                 205 aaa acg gct atg atg tgg aaa aat atc gtc atc agt ggc gtt tca aac    898
Lys Thr Ala Met Met Trp Lys Asn Ile Val Ile Ser Gly Val Ser Asn
210                 215                 220                 225 aca tcc ggt gct atc aca tcc act aat tac cca acg caa tac gcg gtg    946
Thr Ser Gly Ala Ile Thr Ser Thr Asn Tyr Pro Thr Gln Tyr Ala Val
                230                 235                 240 ttt aac aac att aag gcg atg ata ccc att ttg caa caa gcg gtt acg    994
Phe Asn Asn Ile Lys Ala Met Ile Pro Ile Leu Gln Gln Ala Val Thr
            245                 250                 255 ctt tct caa agc aac cac acc cta tct gct agc ttg caa gct caa gcc   1042
Leu Ser Gln Ser Asn His Thr Leu Ser Ala Ser Leu Gln Ala Gln Ala
        260                 265                 270 aca gga tct caa aca aac cct aaa ttc gct aaa gac atc tac act ttc   1090
Thr Gly Ser Gln Thr Asn Pro Lys Phe Ala Lys Asp Ile Tyr Thr Phe
    275                 280                 285 gct caa aac caa aag caa gtc atc tct tac gct caa gac att ttc aac   1138
Ala Gln Asn Gln Lys Gln Val Ile Ser Tyr Ala Gln Asp Ile Phe Asn
290                 295                 300                 305 ctc ttt aat tct atc cct gca gag cag tat aag tat cta gag aaa gct   1186
Leu Phe Asn Ser Ile Pro Ala Glu Gln Tyr Lys Tyr Leu Glu Lys Ala
                310                 315                 320 tac ttg aaa ata ccc aat gcg ggt tca acg cct act aac cct tac aga   1234
Tyr Leu Lys Ile Pro Asn Ala Gly Ser Thr Pro Thr Asn Pro Tyr Arg
```

-continued

```
                325                 330                 335
caa gtg gtg aat tta aac caa gaa gtt cag acg att aaa aac aat gtg    1282
Gln Val Val Asn Leu Asn Gln Glu Val Gln Thr Ile Lys Asn Asn Val
            340                 345                 350 agt tat tat ggt aac cgg gtg gat gcg gct tta agc gtg gct aga gat    1330
Ser Tyr Tyr Gly Asn Arg Val Asp Ala Ala Leu Ser Val Ala Arg Asp
355                 360                 365 gtt tat aac cta aaa tcc aat caa gca gaa atc gta acc gcc tat aac    1378
Val Tyr Asn Leu Lys Ser Asn Gln Ala Glu Ile Val Thr Ala Tyr Asn
370                 375                 380                 385 gac gct aag act ttg agc gaa gag att tct aaa ctc ccg cac aat caa    1426
Asp Ala Lys Thr Leu Ser Glu Glu Ile Ser Lys Leu Pro His Asn Gln
                390                 395                 400 gtc aat aca aaa gac att gtt aca cta cct tac gat aaa aac gcc cca    1474
Val Asn Thr Lys Asp Ile Val Thr Leu Pro Tyr Asp Lys Asn Ala Pro
            405                 410                 415 gca gca ggc caa tcc aac tac caa atc aac cca gag cag caa tcc aat    1522
Ala Ala Gly Gln Ser Asn Tyr Gln Ile Asn Pro Glu Gln Gln Ser Asn
        420                 425                 430 ctt aac caa gct tta gca gcg atg agc aat aac ccc ttt aaa aaa gtg    1570
Leu Asn Gln Ala Leu Ala Ala Met Ser Asn Asn Pro Phe Lys Lys Val
435                 440                 445 ggc atg atc agc tct caa aac aat aac ggc gct ttg aac ggg ctt ggc    1618
Gly Met Ile Ser Ser Gln Asn Asn Asn Gly Ala Leu Asn Gly Leu Gly
450                 455                 460                 465 gtg caa gtg ggt tat aag caa ttc ttt ggc gaa agc aaa aga tgg ggg    1666
Val Gln Val Gly Tyr Lys Gln Phe Phe Gly Glu Ser Lys Arg Trp Gly
                470                 475                 480 tta agg tat tac gga ttc ttt gat tac aac cac ggc tac atc aaa tcc    1714
Leu Arg Tyr Tyr Gly Phe Phe Asp Tyr Asn His Gly Tyr Ile Lys Ser
            485                 490                 495 agc ttc ttt aac tct tct tct gat ata tgg act tat ggc ggt ggg agc    1762
Ser Phe Phe Asn Ser Ser Ser Asp Ile Trp Thr Tyr Gly Gly Gly Ser
        500                 505                 510 gat ttg tta gtg aat att atc aac gat agc atc aca aga aag aac aac    1810
Asp Leu Leu Val Asn Ile Ile Asn Asp Ser Ile Thr Arg Lys Asn Asn
515                 520                 525 aag ctc tcc gtg ggt ctt ttt gga ggc atc caa cta gca ggg act aca    1858
Lys Leu Ser Val Gly Leu Phe Gly Gly Ile Gln Leu Ala Gly Thr Thr
530                 535                 540                 545 tgg ctt aat tct caa tac gtg aat tta acc gcg ttc aat aac cct tac    1906
Trp Leu Asn Ser Gln Tyr Val Asn Leu Thr Ala Phe Asn Asn Pro Tyr
                550                 555                 560 agc gcg aaa gtc aat gct acc aat ttc caa ttc ttg ttc aat ctc ggc    1954
Ser Ala Lys Val Asn Ala Thr Asn Phe Gln Phe Leu Phe Asn Leu Gly
            565                 570                 575 ttg agg acg aat ctc gct aca gct agg aaa aaa gac agc gaa cat tcc    2002
Leu Arg Thr Asn Leu Ala Thr Ala Arg Lys Lys Asp Ser Glu His Ser
        580                 585                 590 gcg caa cat ggc att gaa ttg ggt att aaa atc ccc acc att acc acg    2050
Ala Gln His Gly Ile Glu Leu Gly Ile Lys Ile Pro Thr Ile Thr Thr
595                 600                 605 aat tac tat tct ttt cta ggc act caa ttg caa tac aga agg ctc tat    2098
Asn Tyr Tyr Ser Phe Leu Gly Thr Gln Leu Gln Tyr Arg Arg Leu Tyr
610                 615                 620                 625 agc gtg tat ctc aat tat gtg ttc gct tac tgagtgattc aagctctctt     2148
Ser Val Tyr Leu Asn Tyr Val Phe Ala Tyr
                630                 635 ctttaagggg gtttagaaaa atcgcaacgc caagctttt atcgttggtg ataaaatcta   2208
```

```
caaaactaac ggcgcgacaa caaaccctaa cgctacgctc                            2248
```

<210> SEQ ID NO 16
<211> LENGTH: 652
<212> TYPE: PRT
<213> ORGANISM: Helicobacter pylori
<220> FEATURE:
<221> NAME/KEY: SIGNAL
<222> LOCATION: (1)...(17)

<400> SEQUENCE: 16

```
Met Lys Lys Thr Ile Leu Leu Ser Leu Ser Ala Ser Ser Leu Leu His
        -15                 -10                  -5

Ala Glu Asp Asn Gly Phe Phe Val Ser Ala Gly Tyr Gln Ile Gly Glu
  1               5                  10                  15

Ala Val Gln Met Val Lys Asn Thr Gly Glu Leu Lys Asn Leu Asn Glu
             20                  25                  30

Lys Tyr Glu Gln Leu Ser Gln Tyr Leu Asn Gln Val Ala Ser Leu Lys
         35                  40                  45

Gln Ser Ile Gln Asn Ala Asn Asn Ile Glu Leu Val Asn Ser Ser Leu
     50                  55                  60

Asn Tyr Leu Lys Ser Phe Thr Asn Asn Tyr Asn Ser Thr Thr Gln
 65                  70                  75

Ser Pro Ile Phe Asn Ala Val Gln Ala Val Ile Thr Ser Val Leu Gly
 80                  85                  90                  95

Phe Trp Ser Leu Tyr Ala Gly Asn Tyr Phe Thr Phe Val Gly Lys
                100                 105                 110

Lys Val Gly Asp Ser Gly Gln Pro Ala Ser Val Gln Gly Asn Pro Pro
             115                 120                 125

Phe Lys Thr Ile Ile Glu Asn Cys Ser Gly Ile Glu Asn Cys Ala Met
         130                 135                 140

Asp Gln Thr Thr Tyr Asp Lys Met Lys Lys Leu Ala Glu Asp Leu Gln
     145                 150                 155

Ala Ala Gln Thr Asn Ser Ala Thr Lys Gly Asn Asn Leu Cys Ala Leu
160                 165                 170                 175

Ser Gly Cys Ala Ala Thr Asp Ser Thr Ser Asn Pro Pro Asn Ser Thr
                180                 185                 190

Val Ser Asn Ala Leu Asn Leu Ala Gln Gln Leu Met Asp Leu Ile Ala
             195                 200                 205

Asn Thr Lys Thr Ala Met Met Trp Lys Asn Ile Val Ile Ser Gly Val
         210                 215                 220

Ser Asn Thr Ser Gly Ala Ile Thr Ser Thr Asn Tyr Pro Thr Gln Tyr
 225                 230                 235

Ala Val Phe Asn Asn Ile Lys Ala Met Ile Pro Ile Leu Gln Gln Ala
240                 245                 250                 255

Val Thr Leu Ser Gln Ser Asn His Thr Leu Ser Ala Ser Leu Gln Ala
                260                 265                 270

Gln Ala Thr Gly Ser Gln Thr Asn Pro Lys Phe Ala Lys Asp Ile Tyr
             275                 280                 285

Thr Phe Ala Gln Asn Gln Lys Gln Val Ile Ser Tyr Ala Gln Asp Ile
         290                 295                 300

Phe Asn Leu Phe Asn Ser Ile Pro Ala Glu Gln Tyr Lys Tyr Leu Glu
     305                 310                 315

Lys Ala Tyr Leu Lys Ile Pro Asn Ala Gly Ser Thr Pro Thr Asn Pro
320                 325                 330                 335
```

```
Tyr Arg Gln Val Val Asn Leu Asn Gln Glu Val Gln Thr Ile Lys Asn
                340                 345                 350
Asn Val Ser Tyr Tyr Gly Asn Arg Val Asp Ala Ala Leu Ser Val Ala
                355                 360                 365
Arg Asp Val Tyr Asn Leu Lys Ser Asn Gln Ala Glu Ile Val Thr Ala
                370                 375                 380
Tyr Asn Asp Ala Lys Thr Leu Ser Glu Glu Ile Ser Lys Leu Pro His
                385                 390                 395
Asn Gln Val Asn Thr Lys Asp Ile Val Thr Leu Pro Tyr Asp Lys Asn
400                 405                 410                 415
Ala Pro Ala Ala Gly Gln Ser Asn Tyr Gln Ile Asn Pro Gln Gln
                420                 425                 430
Ser Asn Leu Asn Gln Ala Leu Ala Ala Met Ser Asn Asn Pro Phe Lys
                435                 440                 445
Lys Val Gly Met Ile Ser Ser Gln Asn Asn Asn Gly Ala Leu Asn Gly
                450                 455                 460
Leu Gly Val Gln Val Gly Tyr Lys Gln Phe Phe Gly Glu Ser Lys Arg
                465                 470                 475
Trp Gly Leu Arg Tyr Tyr Gly Phe Phe Asp Tyr Asn His Gly Tyr Ile
480                 485                 490                 495
Lys Ser Ser Phe Phe Asn Ser Ser Ser Asp Ile Trp Thr Tyr Gly Gly
                500                 505                 510
Gly Ser Asp Leu Leu Val Asn Ile Ile Asn Asp Ser Ile Thr Arg Lys
                515                 520                 525
Asn Asn Lys Leu Ser Val Gly Leu Phe Gly Gly Ile Gln Leu Ala Gly
                530                 535                 540
Thr Thr Trp Leu Asn Ser Gln Tyr Val Asn Leu Thr Ala Phe Asn Asn
                545                 550                 555
Pro Tyr Ser Ala Lys Val Asn Ala Thr Asn Phe Gln Phe Leu Phe Asn
560                 565                 570                 575
Leu Gly Leu Arg Thr Asn Leu Ala Thr Ala Arg Lys Lys Asp Ser Glu
                580                 585                 590
His Ser Ala Gln His Gly Ile Glu Leu Gly Ile Lys Ile Pro Thr Ile
                595                 600                 605
Thr Thr Asn Tyr Tyr Ser Phe Leu Gly Thr Gln Leu Gln Tyr Arg Arg
                610                 615                 620
Leu Tyr Ser Val Tyr Leu Asn Tyr Val Phe Ala Tyr
                625                 630                 635

<210> SEQ ID NO 17
<211> LENGTH: 2161
<212> TYPE: DNA
<213> ORGANISM: Helicobacter pylori
<220> FEATURE:
<221> NAME/KEY: CDS
<222> LOCATION: (122)...(2056)
<220> FEATURE:
<221> NAME/KEY: sig_peptide
<222> LOCATION: (122)...(179)

<400> SEQUENCE: 17 caaaatctt  tttttttttt  ttttgaaatc  caataaattt  atggtaaagt  taaacatatt    60
gtaaataaat tttaatttct attcatgttt acaataaaaa aattacttta aggaacattt    120 t atg aaa aag aca att cta ctc tct ctc tct ctc tcg ctt tca tcg ctc    169
  Met Lys Lys Thr Ile Leu Leu Ser Leu Ser Leu Ser Leu Ser Ser Leu
          -15                 -10                  -5
```

```
ttg cac gct gaa gac aac ggc ttt ttt gtg agc gcc ggc tat caa atc    217
Leu His Ala Glu Asp Asn Gly Phe Phe Val Ser Ala Gly Tyr Gln Ile
         1               5                  10 ggc gaa cgg gtg caa atg gtc aaa aac acc ggc gaa ttg aaa aac ttg    265
Gly Glu Arg Val Gln Met Val Lys Asn Thr Gly Glu Leu Lys Asn Leu
     15                  20                  25 aac gaa aaa tac gag caa tta agc caa tct tta gcc caa ctg gct tcg    313
Asn Glu Lys Tyr Glu Gln Leu Ser Gln Ser Leu Ala Gln Leu Ala Ser
 30                  35                  40                  45 tta aaa aaa agc att caa acg gcg aac aac att cag gct gtc aac aat    361
Leu Lys Lys Ser Ile Gln Thr Ala Asn Asn Ile Gln Ala Val Asn Asn
                 50                  55                  60 gct tta agc gat tta aaa agc ttt gcg agt aac aac cac aca aac aaa    409
Ala Leu Ser Asp Leu Lys Ser Phe Ala Ser Asn Asn His Thr Asn Lys
             65                  70                  75 gaa aca tcg ccc atc tac aac acc gcg caa gct gtt atc act tca gta    457
Glu Thr Ser Pro Ile Tyr Asn Thr Ala Gln Ala Val Ile Thr Ser Val
         80                  85                  90 ttg gct ttt tgg agt ctt tat gca ggg aac gct acc agt ttt cat gtg    505
Leu Ala Phe Trp Ser Leu Tyr Ala Gly Asn Ala Thr Ser Phe His Val
     95                 100                 105 acc ggt ttg aat gat gga tct aat gct cct ctt gga aga atc cat caa    553
Thr Gly Leu Asn Asp Gly Ser Asn Ala Pro Leu Gly Arg Ile His Gln
110                 115                 120                 125 gat ggg aac tgc aca gga tta caa caa tgt ttt atg aat aaa gaa act    601
Asp Gly Asn Cys Thr Gly Leu Gln Gln Cys Phe Met Asn Lys Glu Thr
                130                 135                 140 tat gat aaa atg aaa gcg ctt gcc gaa aat ctc caa aaa gct caa ggc    649
Tyr Asp Lys Met Lys Ala Leu Ala Glu Asn Leu Gln Lys Ala Gln Gly
            145                 150                 155 aat ctc tgt gcc tta tca gaa tgc cct agc gat caa tta aat gga aac    697
Asn Leu Cys Ala Leu Ser Glu Cys Pro Ser Asp Gln Leu Asn Gly Asn
        160                 165                 170 aat gga aac aaa act tcc atg act aaa gct ctt gaa acc gcg caa cag    745
Asn Gly Asn Lys Thr Ser Met Thr Lys Ala Leu Glu Thr Ala Gln Gln
    175                 180                 185 ctt atg gat tta atc gca aac act aaa acg gct atg atg tgg aaa aat    793
Leu Met Asp Leu Ile Ala Asn Thr Lys Thr Ala Met Met Trp Lys Asn
190                 195                 200                 205 atc gtc atc gca ggt gtt aca aac aga ccc ggt ggt gct ggc gct atc    841
Ile Val Ile Ala Gly Val Thr Asn Arg Pro Gly Gly Ala Gly Ala Ile
                210                 215                 220 aca tcc act ggt cct gta acc gac tat gcg gtg ttt aac aac att aag    889
Thr Ser Thr Gly Pro Val Thr Asp Tyr Ala Val Phe Asn Asn Ile Lys
            225                 230                 235 gcg atg ata ccc att ttg caa caa gcg gtt acg ctt tct caa agc aac    937
Ala Met Ile Pro Ile Leu Gln Gln Ala Val Thr Leu Ser Gln Ser Asn
        240                 245                 250 cac acc cta tct gct agc ttg caa gct caa gcc aca gga tct caa aca    985
His Thr Leu Ser Ala Ser Leu Gln Ala Gln Ala Thr Gly Ser Gln Thr
    255                 260                 265 aac cct aaa ttc gct aaa gac atc tac act ttc gct caa aac caa aag   1033
Asn Pro Lys Phe Ala Lys Asp Ile Tyr Thr Phe Ala Gln Asn Gln Lys
270                 275                 280                 285 caa gtc atc tct tac gct caa gac att ttc aac ctc ttt aat tct atc   1081
Gln Val Ile Ser Tyr Ala Gln Asp Ile Phe Asn Leu Phe Asn Ser Ile
                290                 295                 300 cct gca gag cag tat aag tat cta gag aaa gct tac ttg aaa ata ccc   1129
Pro Ala Glu Gln Tyr Lys Tyr Leu Glu Lys Ala Tyr Leu Lys Ile Pro
```

```
                    305                 310                 315
aat gcg ggt tca acg cct act aac cct tac aga caa gtg gtg aat tta    1177
Asn Ala Gly Ser Thr Pro Thr Asn Pro Tyr Arg Gln Val Val Asn Leu
        320                 325                 330 aac caa gaa gtt cag acg att aaa aac aat gtg agt tat tat ggt aac    1225
Asn Gln Glu Val Gln Thr Ile Lys Asn Asn Val Ser Tyr Tyr Gly Asn
335                 340                 345 cgg gtg gat gcg gct tta agc gtg gct aga gat gtt tat aac cta aaa    1273
Arg Val Asp Ala Ala Leu Ser Val Ala Arg Asp Val Tyr Asn Leu Lys
350                 355                 360                 365 tcc aat caa gca gaa atc gta acc gcc tat aac gac gct aag act ttg    1321
Ser Asn Gln Ala Glu Ile Val Thr Ala Tyr Asn Asp Ala Lys Thr Leu
        370                 375                 380 agc gaa gag att tct aaa ctc ccg cac aat caa gtc aat aca aaa gac    1369
Ser Glu Glu Ile Ser Lys Leu Pro His Asn Gln Val Asn Thr Lys Asp
        385                 390                 395 att gtt aca cta cct tac gat aaa aac gcc cca gca gca ggc caa tcc    1417
Ile Val Thr Leu Pro Tyr Asp Lys Asn Ala Pro Ala Ala Gly Gln Ser
        400                 405                 410 aac tac caa atc aac cca gag cag caa tcc aat ctt aac caa gct tta    1465
Asn Tyr Gln Ile Asn Pro Glu Gln Gln Ser Asn Leu Asn Gln Ala Leu
        415                 420                 425 gca gcg atg agc aat aac ccc ttt aaa aaa gtg ggc atg atc agc tct    1513
Ala Ala Met Ser Asn Asn Pro Phe Lys Lys Val Gly Met Ile Ser Ser
430                 435                 440                 445 caa aac aat aac ggc gct ttg aac ggg ctt ggc gtg caa gtg ggt tat    1561
Gln Asn Asn Asn Gly Ala Leu Asn Gly Leu Gly Val Gln Val Gly Tyr
                450                 455                 460 aag caa ttc ttt ggc gaa agc aaa aga tgg ggg tta agg tat tac gga    1609
Lys Gln Phe Phe Gly Glu Ser Lys Arg Trp Gly Leu Arg Tyr Tyr Gly
            465                 470                 475 ttc ttt gat tac aac cac ggc tac atc aaa tcc agc ttc ttt aac tct    1657
Phe Phe Asp Tyr Asn His Gly Tyr Ile Lys Ser Ser Phe Phe Asn Ser
        480                 485                 490 tct tct gat ata tgg act tat ggc ggt ggg agc gat ttg tta gtg aat    1705
Ser Ser Asp Ile Trp Thr Tyr Gly Gly Gly Ser Asp Leu Leu Val Asn
        495                 500                 505 att atc aac gat agc atc aca aga aag aac aac aag ctc tcc gtg ggt    1753
Ile Ile Asn Asp Ser Ile Thr Arg Lys Asn Asn Lys Leu Ser Val Gly
510                 515                 520                 525 ctt ttt gga ggc atc caa cta gca gga act aca tgg ctt aat tct caa    1801
Leu Phe Gly Gly Ile Gln Leu Ala Gly Thr Thr Trp Leu Asn Ser Gln
                530                 535                 540 tac gtg aat tta acc gcg ttc aat aac cct tac agc gcg aaa gtc aat    1849
Tyr Val Asn Leu Thr Ala Phe Asn Asn Pro Tyr Ser Ala Lys Val Asn
            545                 550                 555 gct acc aat ttc caa ttc ttg ttc aat ctc ggc ttg agg acg aat ctc    1897
Ala Thr Asn Phe Gln Phe Leu Phe Asn Leu Gly Leu Arg Thr Asn Leu
        560                 565                 570 gct aca gct agg aaa aaa gac agc gaa cat tcc gcg caa cat ggc att    1945
Ala Thr Ala Arg Lys Lys Asp Ser Glu His Ser Ala Gln His Gly Ile
        575                 580                 585 gaa ttg ggt att aaa atc ccc acc att acc acg aat tac tat tct ttt    1993
Glu Leu Gly Ile Lys Ile Pro Thr Ile Thr Thr Asn Tyr Tyr Ser Phe
590                 595                 600                 605 cta ggc act caa ttg caa tac aga agg ctc tat agc gtg tat ctc aat    2041
Leu Gly Thr Gln Leu Gln Tyr Arg Arg Leu Tyr Ser Val Tyr Leu Asn
                610                 615                 620 tat gtg ttc gct tat taaaaaatct tcttttaaa atagggggag cttcatcaaa    2096
Tyr Val Phe Ala Tyr
```

-continued

```
Tyr Val Phe Ala Tyr
            625 tctattttga tagttatcaa tatttgatga aaataaagtc aaaaacaaaa taaaccaaat    2156 caccc                                                               2161

<210> SEQ ID NO 18
<211> LENGTH: 645
<212> TYPE: PRT
<213> ORGANISM: Helicobacter pylori
<220> FEATURE:
<221> NAME/KEY: SIGNAL
<222> LOCATION: (1)...(19)

<400> SEQUENCE: 18

Met Lys Lys Thr Ile Leu Leu Ser Leu Ser Leu Ser Ser Leu
                -15                 -10                 -5

Leu His Ala Glu Asp Asn Gly Phe Phe Val Ser Ala Gly Tyr Gln Ile
                 1               5                  10

Gly Glu Arg Val Gln Met Val Lys Asn Thr Gly Glu Leu Lys Asn Leu
         15                  20                  25

Asn Glu Lys Tyr Glu Gln Leu Ser Gln Ser Leu Ala Gln Leu Ala Ser
 30                  35                  40                  45

Leu Lys Lys Ser Ile Gln Thr Ala Asn Asn Ile Gln Ala Val Asn Asn
                 50                  55                  60

Ala Leu Ser Asp Leu Lys Ser Phe Ala Ser Asn Asn His Thr Asn Lys
             65                  70                  75

Glu Thr Ser Pro Ile Tyr Asn Thr Ala Gln Ala Val Ile Thr Ser Val
             80                  85                  90

Leu Ala Phe Trp Ser Leu Tyr Ala Gly Asn Ala Thr Ser Phe His Val
     95                 100                 105

Thr Gly Leu Asn Asp Gly Ser Asn Ala Pro Leu Gly Arg Ile His Gln
110                 115                 120                 125

Asp Gly Asn Cys Thr Gly Leu Gln Gln Cys Phe Met Asn Lys Glu Thr
                130                 135                 140

Tyr Asp Lys Met Lys Ala Leu Ala Glu Asn Leu Gln Lys Ala Gln Gly
                145                 150                 155

Asn Leu Cys Ala Leu Ser Glu Cys Pro Ser Asp Gln Leu Asn Gly Asn
                160                 165                 170

Asn Gly Asn Lys Thr Ser Met Thr Lys Ala Leu Glu Thr Ala Gln Gln
            175                 180                 185

Leu Met Asp Leu Ile Ala Asn Thr Lys Thr Ala Met Met Trp Lys Asn
190                 195                 200                 205

Ile Val Ile Ala Gly Val Thr Asn Arg Pro Gly Gly Ala Gly Ala Ile
                210                 215                 220

Thr Ser Thr Gly Pro Val Thr Asp Tyr Ala Val Phe Asn Asn Ile Lys
            225                 230                 235

Ala Met Ile Pro Ile Leu Gln Gln Ala Val Thr Leu Ser Gln Ser Asn
        240                 245                 250

His Thr Leu Ser Ala Ser Leu Gln Ala Gln Ala Thr Gly Ser Gln Thr
        255                 260                 265

Asn Pro Lys Phe Ala Lys Asp Ile Tyr Thr Phe Ala Gln Asn Gln Lys
270                 275                 280                 285

Gln Val Ile Ser Tyr Ala Gln Asp Ile Phe Asn Leu Phe Asn Ser Ile
                290                 295                 300

Pro Ala Glu Gln Tyr Lys Tyr Leu Glu Lys Ala Tyr Leu Lys Ile Pro
```

```
                    305                 310                 315
Asn Ala Gly Ser Thr Pro Thr Asn Pro Tyr Arg Gln Val Val Asn Leu
            320                 325                 330
Asn Gln Glu Val Gln Thr Ile Lys Asn Asn Val Ser Tyr Tyr Gly Asn
        335                 340                 345
Arg Val Asp Ala Ala Leu Ser Val Ala Arg Asp Val Tyr Asn Leu Lys
350                 355                 360                 365
Ser Asn Gln Ala Glu Ile Val Thr Ala Tyr Asn Asp Ala Lys Thr Leu
                370                 375                 380
Ser Glu Glu Ile Ser Lys Leu Pro His Asn Gln Val Asn Thr Lys Asp
            385                 390                 395
Ile Val Thr Leu Pro Tyr Asp Lys Asn Ala Pro Ala Gly Gln Ser
        400                 405                 410
Asn Tyr Gln Ile Asn Pro Glu Gln Gln Ser Asn Leu Asn Gln Ala Leu
        415                 420                 425
Ala Ala Met Ser Asn Asn Pro Phe Lys Lys Val Gly Met Ile Ser Ser
430                 435                 440                 445
Gln Asn Asn Asn Gly Ala Leu Asn Gly Leu Gly Val Gln Val Gly Tyr
                450                 455                 460
Lys Gln Phe Phe Gly Glu Ser Lys Arg Trp Gly Leu Arg Tyr Tyr Gly
                465                 470                 475
Phe Phe Asp Tyr Asn His Gly Tyr Ile Lys Ser Ser Phe Phe Asn Ser
                480                 485                 490
Ser Ser Asp Ile Trp Thr Tyr Gly Gly Gly Ser Asp Leu Leu Val Asn
            495                 500                 505
Ile Ile Asn Asp Ser Ile Thr Arg Lys Asn Asn Lys Leu Ser Val Gly
510                 515                 520                 525
Leu Phe Gly Gly Ile Gln Leu Ala Gly Thr Thr Trp Leu Asn Ser Gln
                530                 535                 540
Tyr Val Asn Leu Thr Ala Phe Asn Asn Pro Tyr Ser Ala Lys Val Asn
            545                 550                 555
Ala Thr Asn Phe Gln Phe Leu Phe Asn Leu Gly Leu Arg Thr Asn Leu
            560                 565                 570
Ala Thr Ala Arg Lys Lys Asp Ser Glu His Ser Ala Gln His Gly Ile
575                 580                 585
Glu Leu Gly Ile Lys Ile Pro Thr Ile Thr Asn Tyr Tyr Ser Phe
590                 595                 600                 605
Leu Gly Thr Gln Leu Gln Tyr Arg Arg Leu Tyr Ser Val Tyr Leu Asn
                610                 615                 620
Tyr Val Phe Ala Tyr
            625

<210> SEQ ID NO 19
<211> LENGTH: 1799
<212> TYPE: DNA
<213> ORGANISM: Helicobacter pylori
<220> FEATURE:
<221> NAME/KEY: CDS
<222> LOCATION: (185)...(1633)
<220> FEATURE:
<221> NAME/KEY: sig_peptide
<222> LOCATION: (185)...(233)

<400> SEQUENCE: 19
tactcaaaac attttccact atcaaaaacc ttttttttaa atccaaaaaa aaagcaaaat      60
ttcttaattt ttgctcaatt ttattaaaaa ttcaataaat ttatggcaca atttaaactt    120
```

```
attgtaaata aagtttcaat ttgatacgat tttacaaaca aaacattact ttaaggaaca      180 tttt atg aaa aaa acg att tta ctt tct ctt atg gtt tca tcg ctc ctc      229
     Met Lys Lys Thr Ile Leu Leu Ser Leu Met Val Ser Ser Leu Leu
         -15                 -10                 -5 gct gaa aat gac ggc gtt ttt atg agc gtg ggc tat caa atc ggc gaa      277
Ala Glu Asn Asp Gly Val Phe Met Ser Val Gly Tyr Gln Ile Gly Glu
1                   5                   10                  15 gcg gtt caa caa gtg aaa aac acc ggc gaa atc caa aaa gtc tcc aac      325
Ala Val Gln Gln Val Lys Asn Thr Gly Glu Ile Gln Lys Val Ser Asn
                20                  25                  30 gct tac gaa aat ttg aac aat ctt tta acc cgc tat aac gaa ctc aaa      373
Ala Tyr Glu Asn Leu Asn Asn Leu Leu Thr Arg Tyr Asn Glu Leu Lys
            35                  40                  45 caa acg gcc tct aac acc aat tca agt acc gct caa gcg att gat aat      421
Gln Thr Ala Ser Asn Thr Asn Ser Ser Thr Ala Gln Ala Ile Asp Asn
        50                  55                  60 cta aaa gag agc gct agc cga ttg aaa acg acc ccc aat agc gct aat      469
Leu Lys Glu Ser Ala Ser Arg Leu Lys Thr Thr Pro Asn Ser Ala Asn
    65                  70                  75 caa gcc gtg tct tca gcg ctc agc tct gcg gta gcc atg tgg caa gta      517
Gln Ala Val Ser Ser Ala Leu Ser Ser Ala Val Ala Met Trp Gln Val
80                  85                  90                  95 ata gtc tct aat tta gcc aat aac tcg cta ccc act agt gaa tac aac      565
Ile Val Ser Asn Leu Ala Asn Asn Ser Leu Pro Thr Ser Glu Tyr Asn
                100                 105                 110 aaa atc aat gcg att tct caa tcg ctc caa aac acc cta gaa aat aaa      613
Lys Ile Asn Ala Ile Ser Gln Ser Leu Gln Asn Thr Leu Glu Asn Lys
            115                 120                 125 aac aat gat ctt aaa att gaa aat gac tac gac cat ctt tta act caa      661
Asn Asn Asp Leu Lys Ile Glu Asn Asp Tyr Asp His Leu Leu Thr Gln
        130                 135                 140 gct agc acc att att aat acc ctt caa agc caa tgc cca ggc ata gac      709
Ala Ser Thr Ile Ile Asn Thr Leu Gln Ser Gln Cys Pro Gly Ile Asp
    145                 150                 155 gga ggc aat ggc aaa cca tgg ggc att aat gca agc ggg aac gca tgc      757
Gly Gly Asn Gly Lys Pro Trp Gly Ile Asn Ala Ser Gly Asn Ala Cys
160                 165                 170                 175 aat att ttt ggc aac acc ttt aac gcc atc act agc atg ata gat agc      805
Asn Ile Phe Gly Asn Thr Phe Asn Ala Ile Thr Ser Met Ile Asp Ser
                180                 185                 190 gct aaa aaa gcc gcc gca gat gcc cga aga act gcc cca gaa agt cca      853
Ala Lys Lys Ala Ala Ala Asp Ala Arg Arg Thr Ala Pro Glu Ser Pro
            195                 200                 205 aac caa cca agt gcg ttt aac aac gct gat ttc aat aaa aac ctt aat      901
Asn Gln Pro Ser Ala Phe Asn Asn Ala Asp Phe Asn Lys Asn Leu Asn
        210                 215                 220 caa gtc tca agc gtt att aat gac acg atc tct tac ctc aaa ggg gac      949
Gln Val Ser Ser Val Ile Asn Asp Thr Ile Ser Tyr Leu Lys Gly Asp
    225                 230                 235 aat tta gca acc atc tac aac acc ctt caa aaa acg ccc gat tct aaa      997
Asn Leu Ala Thr Ile Tyr Asn Thr Leu Gln Lys Thr Pro Asp Ser Lys
240                 245                 250                 255 ggg ttt caa agt ttg gtg agc cga tct agc tat agt tat tcc ctc aac     1045
Gly Phe Gln Ser Leu Val Ser Arg Ser Ser Tyr Ser Tyr Ser Leu Asn
                260                 265                 270 gaa acc caa tat tct gaa ttc caa act acc acc aaa gag ttt ggc cat     1093
Glu Thr Gln Tyr Ser Glu Phe Gln Thr Thr Thr Lys Glu Phe Gly His
            275                 280                 285
```

```
aac cct ttt aga agc gtg ggt tta atc aac tct caa agc aat aac gga    1141
Asn Pro Phe Arg Ser Val Gly Leu Ile Asn Ser Gln Ser Asn Asn Gly
        290                 295                 300 gcg atg aat ggc gtg ggc gtg caa tta ggc tat aag caa ttc ttt ggg    1189
Ala Met Asn Gly Val Gly Val Gln Leu Gly Tyr Lys Gln Phe Phe Gly
    305                 310                 315 aaa aat aaa ttt ttt ggg atc cgt tat tat gcc ttt ttt gat tac aac    1237
Lys Asn Lys Phe Phe Gly Ile Arg Tyr Tyr Ala Phe Phe Asp Tyr Asn
320                 325                 330                 335 cat gcc tat atc aaa tcc aac ttt ttc aac tcc gct tcc aat gtt ttc    1285
His Ala Tyr Ile Lys Ser Asn Phe Phe Asn Ser Ala Ser Asn Val Phe
            340                 345                 350 act tat ggc gca ggc agt gat ctt tta ttg aat ttc atc aat ggc gga    1333
Thr Tyr Gly Ala Gly Ser Asp Leu Leu Leu Asn Phe Ile Asn Gly Gly
                355                 360                 365 tcc gat aaa aac cgc aaa gtc tct ttt ggc att ttt gga ggc atc gct    1381
Ser Asp Lys Asn Arg Lys Val Ser Phe Gly Ile Phe Gly Gly Ile Ala
        370                 375                 380 cta gca ggc acg aca tgg ctt aat tcc caa ttt atg aat tta aaa acc    1429
Leu Ala Gly Thr Thr Trp Leu Asn Ser Gln Phe Met Asn Leu Lys Thr
385                 390                 395 acc aat agc gcc tac agc gct aag atc aac aac acc aat ttc caa ttc    1477
Thr Asn Ser Ala Tyr Ser Ala Lys Ile Asn Asn Thr Asn Phe Gln Phe
400                 405                 410                 415 tta ttc aat act ggt tta agg ctt caa ggg att cac cat ggc gtt gaa    1525
Leu Phe Asn Thr Gly Leu Arg Leu Gln Gly Ile His His Gly Val Glu
            420                 425                 430 tta ggc gtg aaa atc ccc acc atc aac acg aat tac tat tct ttc atg    1573
Leu Gly Val Lys Ile Pro Thr Ile Asn Thr Asn Tyr Tyr Ser Phe Met
                435                 440                 445 ggc gct aaa tta gca tac cga aga ctt tat agc gtg tat ttc aat tat    1621
Gly Ala Lys Leu Ala Tyr Arg Arg Leu Tyr Ser Val Tyr Phe Asn Tyr
        450                 455                 460 gtt ttg gcc tat tgatattgaa tcggttctca ttactaatga ggacaaagcc        1673
Val Leu Ala Tyr
        465 aaacttttg gctctcaatg aataacggca tcattttact tgactttta caaaaaacac    1733 actaaaattt cttttcttt tttgagcgaa attccagatt agctcagcgg tagagtaggc   1793
ggctgt                                                              1799

<210> SEQ ID NO 20
<211> LENGTH: 483
<212> TYPE: PRT
<213> ORGANISM: Helicobacter pylori
<220> FEATURE:
<221> NAME/KEY: SIGNAL
<222> LOCATION: (1)...(16)

<400> SEQUENCE: 20

Met Lys Lys Thr Ile Leu Leu Ser Leu Met Val Ser Ser Leu Leu Ala
        -15                 -10                 -5

Glu Asn Asp Gly Val Phe Met Ser Val Gly Tyr Gln Ile Gly Glu Ala
1               5                   10                  15

Val Gln Gln Val Lys Asn Thr Gly Glu Ile Gln Lys Val Ser Asn Ala
            20                  25                  30

Tyr Glu Asn Leu Asn Asn Leu Leu Thr Arg Tyr Asn Glu Leu Lys Gln
        35                  40                  45

Thr Ala Ser Asn Thr Asn Ser Ser Thr Ala Gln Ala Ile Asp Asn Leu
    50                  55                  60
```

```
Lys Glu Ser Ala Ser Arg Leu Lys Thr Thr Pro Asn Ser Ala Asn Gln
 65                  70                  75                  80

Ala Val Ser Ser Ala Leu Ser Ser Ala Val Ala Met Trp Gln Val Ile
                 85                  90                  95

Val Ser Asn Leu Ala Asn Asn Ser Leu Pro Thr Ser Glu Tyr Asn Lys
            100                 105                 110

Ile Asn Ala Ile Ser Gln Ser Leu Gln Asn Thr Leu Glu Asn Lys Asn
            115                 120                 125

Asn Asp Leu Lys Ile Glu Asn Asp Tyr Asp His Leu Leu Thr Gln Ala
    130                 135                 140

Ser Thr Ile Ile Asn Thr Leu Gln Ser Gln Cys Pro Gly Ile Asp Gly
145                 150                 155                 160

Gly Asn Gly Lys Pro Trp Gly Ile Asn Ala Ser Gly Asn Ala Cys Asn
                165                 170                 175

Ile Phe Gly Asn Thr Phe Asn Ala Ile Thr Ser Met Ile Asp Ser Ala
            180                 185                 190

Lys Lys Ala Ala Ala Asp Ala Arg Arg Thr Ala Pro Glu Ser Pro Asn
            195                 200                 205

Gln Pro Ser Ala Phe Asn Asn Ala Asp Phe Asn Lys Asn Leu Asn Gln
    210                 215                 220

Val Ser Ser Val Ile Asn Asp Thr Ile Ser Tyr Leu Lys Gly Asp Asn
225                 230                 235                 240

Leu Ala Thr Ile Tyr Asn Thr Leu Gln Lys Thr Pro Asp Ser Lys Gly
                245                 250                 255

Phe Gln Ser Leu Val Ser Arg Ser Ser Tyr Ser Tyr Ser Leu Asn Glu
            260                 265                 270

Thr Gln Tyr Ser Glu Phe Gln Thr Thr Thr Lys Glu Phe Gly His Asn
            275                 280                 285

Pro Phe Arg Ser Val Gly Leu Ile Asn Ser Gln Ser Asn Asn Gly Ala
    290                 295                 300

Met Asn Gly Val Gly Val Gln Leu Gly Tyr Lys Gln Phe Phe Gly Lys
305                 310                 315                 320

Asn Lys Phe Phe Gly Ile Arg Tyr Tyr Ala Phe Phe Asp Tyr Asn His
                325                 330                 335

Ala Tyr Ile Lys Ser Asn Phe Phe Asn Ser Ala Ser Asn Val Phe Thr
            340                 345                 350

Tyr Gly Ala Gly Ser Asp Leu Leu Leu Asn Phe Ile Asn Gly Gly Ser
            355                 360                 365

Asp Lys Asn Arg Lys Val Ser Phe Gly Ile Phe Gly Gly Ile Ala Leu
    370                 375                 380

Ala Gly Thr Thr Trp Leu Asn Ser Gln Phe Met Asn Leu Lys Thr Thr
385                 390                 395                 400

Asn Ser Ala Tyr Ser Ala Lys Ile Asn Asn Thr Asn Phe Gln Phe Leu
                405                 410                 415

Phe Asn Thr Gly Leu Arg Leu Gln Gly Ile His His Gly Val Glu Leu
            420                 425                 430

Gly Val Lys Ile Pro Thr Ile Asn Thr Asn Tyr Tyr Ser Phe Met Gly
            435                 440                 445

Ala Lys Leu Ala Tyr Arg Arg Leu Tyr Ser Val Tyr Phe Asn Tyr Val
    450                 455                 460

Leu Ala Tyr
465
```

-continued

```
<210> SEQ ID NO 21
<211> LENGTH: 2338
<212> TYPE: DNA
<213> ORGANISM: Helicobacter pylori
<220> FEATURE:
<221> NAME/KEY: CDS
<222> LOCATION: (146)...(2218)
<220> FEATURE:
<221> NAME/KEY: sig_peptide
<222> LOCATION: (146)...(200)

<400> SEQUENCE: 21
acttaaaatt gttttttttt tttttcaaaa tataaatttt aagccaaaaa taagcatttt      60
atggtaaaat ggcgaacttt cataaacatg actattatgg gaatgtcatg ggaatgtgaa     120
gaaaaatcta ttaaaaggag aaaac atg aaa aaa tcc ctc tta ctc tct ctt      172
                            Met Lys Lys Ser Leu Leu Leu Ser Leu
                                -15                 -10 tct ctc atc gct tcc tta tca aga gct gaa gat gac gga ttt tat acg      220
Ser Leu Ile Ala Ser Leu Ser Arg Ala Glu Asp Asp Gly Phe Tyr Thr
            -5                  1               5 agt gtg ggc tat cag atc ggt gaa gcg gtc caa caa gtg aaa aac aca      268
Ser Val Gly Tyr Gln Ile Gly Glu Ala Val Gln Gln Val Lys Asn Thr
        10                  15                  20 gga gca ttg caa aat ctt gca gac aga tac gat aac tta aac aac ctt      316
Gly Ala Leu Gln Asn Leu Ala Asp Arg Tyr Asp Asn Leu Asn Asn Leu
    25                  30                  35 tta aac caa tac aat tat tta aat tcc tta gtc aat tta gcc agc acg      364
Leu Asn Gln Tyr Asn Tyr Leu Asn Ser Leu Val Asn Leu Ala Ser Thr
 40                  45                  50                  55 ccg agc gcg atc acc ggt gcg att gat aat tta agc tca agc gcg att      412
Pro Ser Ala Ile Thr Gly Ala Ile Asp Asn Leu Ser Ser Ser Ala Ile
                60                  65                  70 aac ctc act agc gcc acc acc act tcc ccc gcc tat caa gct gtg gct      460
Asn Leu Thr Ser Ala Thr Thr Thr Ser Pro Ala Tyr Gln Ala Val Ala
        75                  80                  85 tta gcg ctc aat gcc gct gtg ggc atg tgg caa gtc ata gcc ctt ttt      508
Leu Ala Leu Asn Ala Ala Val Gly Met Trp Gln Val Ile Ala Leu Phe
    90                  95                 100 att ggc tgt ggc cct ggc cct acc aat aat caa agc tat caa tcg ttt      556
Ile Gly Cys Gly Pro Gly Pro Thr Asn Asn Gln Ser Tyr Gln Ser Phe
105                 110                 115 ggt aac aca cca gcc ctt aat ggg acc acc acc act tgc aat caa gca      604
Gly Asn Thr Pro Ala Leu Asn Gly Thr Thr Thr Thr Cys Asn Gln Ala
120                 125                 130                 135 tat ggg aca ggc cct aat ggc atc cta tct att gat gaa tac caa aaa      652
Tyr Gly Thr Gly Pro Asn Gly Ile Leu Ser Ile Asp Glu Tyr Gln Lys
            140                 145                 150 ctc aac caa gct tat cag atc atc caa acc gct tta aac caa aat caa      700
Leu Asn Gln Ala Tyr Gln Ile Ile Gln Thr Ala Leu Asn Gln Asn Gln
        155                 160                 165 ggg ggt ggg atg cct gcc ttg aat gac acc acc aaa aca ggg gta gtc      748
Gly Gly Gly Met Pro Ala Leu Asn Asp Thr Thr Lys Thr Gly Val Val
    170                 175                 180 aac ata caa caa acc aat tat agg acc acc aca caa aac aat atc ata      796
Asn Ile Gln Gln Thr Asn Tyr Arg Thr Thr Thr Gln Asn Asn Ile Ile
185                 190                 195 gag cat tat tat aca gag aat ggg aaa gag atc cca gtc tct tat tca      844
Glu His Tyr Tyr Thr Glu Asn Gly Lys Glu Ile Pro Val Ser Tyr Ser
200                 205                 210                 215 ggc gga tca tca ttc tcg cct aca ata caa ttg aca tac cat aat aac      892
```

```
                Gly Gly Ser Ser Phe Ser Pro Thr Ile Gln Leu Thr Tyr His Asn Asn
                            220                 225                 230 gct gaa aac ctt ttg caa caa gcc gcc act atc atg caa gtc ctt att        940
Ala Glu Asn Leu Leu Gln Gln Ala Ala Thr Ile Met Gln Val Leu Ile
            235                 240                 245 act caa aag ccg cat gtg caa acg agc aat ggc ggt aaa gcg tgg ggg        988
Thr Gln Lys Pro His Val Gln Thr Ser Asn Gly Gly Lys Ala Trp Gly
        250                 255                 260 ttg agt tct acg cct ggg aat gtg atg gat att ttt ggt cct tct ttt       1036
Leu Ser Ser Thr Pro Gly Asn Val Met Asp Ile Phe Gly Pro Ser Phe
    265                 270                 275 aac gct att aat gag atg att aaa aac gct caa aca gcc cta gca aaa       1084
Asn Ala Ile Asn Glu Met Ile Lys Asn Ala Gln Thr Ala Leu Ala Lys
280                 285                 290                 295 acc caa cag ctt aac gct aat gaa aac gcc caa atc acg caa ccc aac       1132
Thr Gln Gln Leu Asn Ala Asn Glu Asn Ala Gln Ile Thr Gln Pro Asn
                300                 305                 310 aat ttc aac ccc tac acc tct aaa gac aaa ggg ttc gct caa gaa atg       1180
Asn Phe Asn Pro Tyr Thr Ser Lys Asp Lys Gly Phe Ala Gln Glu Met
            315                 320                 325 ctc aat aga gct gaa gct caa gca gag att tta aat tta gct aag caa       1228
Leu Asn Arg Ala Glu Ala Gln Ala Glu Ile Leu Asn Leu Ala Lys Gln
        330                 335                 340 gta gcg aac aat ttc cac agc att caa ggg cct att caa ggg gat tta       1276
Val Ala Asn Asn Phe His Ser Ile Gln Gly Pro Ile Gln Gly Asp Leu
    345                 350                 355 gaa gaa tgt aaa gca gga tcg gct ggc gtg atc act aat aac act tgg       1324
Glu Glu Cys Lys Ala Gly Ser Ala Gly Val Ile Thr Asn Asn Thr Trp
360                 365                 370                 375 ggt tca ggt tgc gcg ttt gtg aaa gaa act tta aac tct tta gag caa       1372
Gly Ser Gly Cys Ala Phe Val Lys Glu Thr Leu Asn Ser Leu Glu Gln
                380                 385                 390 cac acc gct tat tac ggc aac cag gtc aat cag gat agg gct ttg gct       1420
His Thr Ala Tyr Tyr Gly Asn Gln Val Asn Gln Asp Arg Ala Leu Ala
            395                 400                 405 caa acc att ttg aat ttt aaa gaa gcc ctt aac acc ctg aat aaa gac       1468
Gln Thr Ile Leu Asn Phe Lys Glu Ala Leu Asn Thr Leu Asn Lys Asp
        410                 415                 420 tca aaa gcg atc aat agc ggt atc tcc aac ttg cct aac gct aaa tct       1516
Ser Lys Ala Ile Asn Ser Gly Ile Ser Asn Leu Pro Asn Ala Lys Ser
    425                 430                 435 ctt caa aac atg acg cat gcc act caa aac cct aat tcc cca gaa ggt       1564
Leu Gln Asn Met Thr His Ala Thr Gln Asn Pro Asn Ser Pro Glu Gly
440                 445                 450                 455 ctg ctc act tat tct ttg gat tca agc aaa tac aac cag ctc caa acc       1612
Leu Leu Thr Tyr Ser Leu Asp Ser Ser Lys Tyr Asn Gln Leu Gln Thr
                460                 465                 470 atc gcg caa gaa ttg ggc aaa aac cct ttc agg cgc ttt ggc gtg att       1660
Ile Ala Gln Glu Leu Gly Lys Asn Pro Phe Arg Arg Phe Gly Val Ile
            475                 480                 485 gac ttt caa aac aac aac ggc gca atg aac ggg atc ggc gtg caa gtg       1708
Asp Phe Gln Asn Asn Asn Gly Ala Met Asn Gly Ile Gly Val Gln Val
        490                 495                 500 ggt tat aaa caa ttc ttt ggt aaa aaa agg aat tgg ggg tta agg tat       1756
Gly Tyr Lys Gln Phe Phe Gly Lys Lys Arg Asn Trp Gly Leu Arg Tyr
    505                 510                 515 tat ggt ttc ttt gat tat aac cat gct tat atc aaa tct aat ttt ttc       1804
Tyr Gly Phe Phe Asp Tyr Asn His Ala Tyr Ile Lys Ser Asn Phe Phe
520                 525                 530                 535
```

```
aac tcc gct tct gat gtg tgg act tat ggg gtg ggt atg gac gct ctc   1852
Asn Ser Ala Ser Asp Val Trp Thr Tyr Gly Val Gly Met Asp Ala Leu
                540                 545                 550 tat aac ttc atc aac gat aaa aac acc aac ttt tta ggc aag aac aac   1900
Tyr Asn Phe Ile Asn Asp Lys Asn Thr Asn Phe Leu Gly Lys Asn Asn
            555                 560                 565 aag ctt tca gta ggg ctt ttt gga ggc ttt gcg tta gcc ggg act tcg   1948
Lys Leu Ser Val Gly Leu Phe Gly Gly Phe Ala Leu Ala Gly Thr Ser
        570                 575                 580 tgg ctt aat tcc caa caa gtg aat ttg acc atg atg aat ggc att tat   1996
Trp Leu Asn Ser Gln Gln Val Asn Leu Thr Met Met Asn Gly Ile Tyr
    585                 590                 595 aac gct aat gtc agc act tct aac ttc caa ttt ttg ttt gat tta ggc   2044
Asn Ala Asn Val Ser Thr Ser Asn Phe Gln Phe Leu Phe Asp Leu Gly
600                 605                 610                 615 ttg aga atg aac ctc gct agg cct aag aaa aaa gac agc gat cat gcc   2092
Leu Arg Met Asn Leu Ala Arg Pro Lys Lys Lys Asp Ser Asp His Ala
                620                 625                 630 gct cag cat ggc att gaa cta ggt ttt aag atc ccc acg atc aac acc   2140
Ala Gln His Gly Ile Glu Leu Gly Phe Lys Ile Pro Thr Ile Asn Thr
            635                 640                 645 aac tat tat tct ttc atg ggc gct aaa cta gaa tac aga agg atg tat   2188
Asn Tyr Tyr Ser Phe Met Gly Ala Lys Leu Glu Tyr Arg Arg Met Tyr
        650                 655                 660 agc ctt ttt ctc aat tat gtg ttt gct tac taaaaactct ctttaaaaaa    2238
Ser Leu Phe Leu Asn Tyr Val Phe Ala Tyr
    665                 670 ggggtttgtt taaaaacgct taaaagcatt tttaaaatta agcagtaaag agcctagata  2298
atctcttgca accgctctca agcgataaaa ttaaagtgat                       2338

<210> SEQ ID NO 22
<211> LENGTH: 690
<212> TYPE: PRT
<213> ORGANISM: Helicobacter pylori
<220> FEATURE:
<221> NAME/KEY: SIGNAL
<222> LOCATION: (1)...(18)

<400> SEQUENCE: 22

Met Lys Lys Ser Leu Leu Leu Ser Leu Ser Leu Ile Ala Ser Leu Ser
                -15                 -10                 -5

Ala Glu Asp Asp Gly Phe Tyr Thr Ser Val Gly Tyr Gln Ile Gly Glu
  1               5                  10

Ala Val Gln Gln Val Lys Asn Thr Gly Ala Leu Gln Asn Leu Ala Asp
 15                 20                 25                  30

Arg Tyr Asp Asn Leu Asn Asn Leu Leu Asn Gln Tyr Asn Tyr Leu Asn
                35                  40                  45

Ser Leu Val Asn Leu Ala Ser Thr Pro Ser Ala Ile Thr Gly Ala Ile
            50                  55                  60

Asp Asn Leu Ser Ser Ser Ala Ile Asn Leu Thr Ser Ala Thr Thr Thr
            65                  70                  75

Ser Pro Ala Tyr Gln Ala Val Ala Leu Ala Leu Asn Ala Ala Val Gly
     80                  85                  90

Met Trp Gln Val Ile Ala Leu Phe Ile Gly Cys Gly Pro Gly Pro Thr
 95                 100                 105                 110

Asn Asn Gln Ser Tyr Gln Ser Phe Gly Asn Thr Pro Ala Leu Asn Gly
                115                 120                 125

Thr Thr Thr Thr Cys Asn Gln Ala Tyr Gly Thr Gly Pro Asn Gly Ile
```

-continued

```
                130                 135                 140
Leu Ser Ile Asp Glu Tyr Gln Lys Leu Asn Gln Ala Tyr Gln Ile Ile
            145                 150                 155
Gln Thr Ala Leu Asn Gln Asn Gln Gly Gly Met Pro Ala Leu Asn
    160                 165                 170
Asp Thr Thr Lys Thr Gly Val Val Asn Ile Gln Gln Thr Asn Tyr Arg
175                 180                 185                 190
Thr Thr Thr Gln Asn Asn Ile Ile Glu His Tyr Tyr Thr Glu Asn Gly
                195                 200                 205
Lys Glu Ile Pro Val Ser Tyr Ser Gly Ser Ser Phe Ser Pro Thr
                210                 215                 220
Ile Gln Leu Thr Tyr His Asn Asn Ala Glu Asn Leu Leu Gln Gln Ala
            225                 230                 235
Ala Thr Ile Met Gln Val Leu Ile Thr Gln Lys Pro His Val Gln Thr
    240                 245                 250
Ser Asn Gly Gly Lys Ala Trp Gly Leu Ser Ser Thr Pro Gly Asn Val
255                 260                 265                 270
Met Asp Ile Phe Gly Pro Ser Phe Asn Ala Ile Asn Glu Met Ile Lys
            275                 280                 285
Asn Ala Gln Thr Ala Leu Ala Lys Thr Gln Gln Leu Asn Ala Asn Glu
            290                 295                 300
Asn Ala Gln Ile Thr Gln Pro Asn Asn Phe Asn Pro Tyr Thr Ser Lys
            305                 310                 315
Asp Lys Gly Phe Ala Gln Glu Met Leu Asn Arg Ala Glu Ala Gln Ala
            320                 325                 330
Glu Ile Leu Asn Leu Ala Lys Gln Val Ala Asn Asn Phe His Ser Ile
335                 340                 345                 350
Gln Gly Pro Ile Gln Gly Asp Leu Glu Glu Cys Lys Ala Gly Ser Ala
            355                 360                 365
Gly Val Ile Thr Asn Asn Thr Trp Gly Ser Gly Cys Ala Phe Val Lys
            370                 375                 380
Glu Thr Leu Asn Ser Leu Glu Gln His Thr Ala Tyr Tyr Gly Asn Gln
            385                 390                 395
Val Asn Gln Asp Arg Ala Leu Ala Gln Thr Ile Leu Asn Phe Lys Glu
    400                 405                 410
Ala Leu Asn Thr Leu Asn Lys Asp Ser Lys Ala Ile Asn Ser Gly Ile
415                 420                 425                 430
Ser Asn Leu Pro Asn Ala Lys Ser Leu Gln Asn Met Thr His Ala Thr
            435                 440                 445
Gln Asn Pro Asn Ser Pro Glu Gly Leu Leu Thr Tyr Ser Leu Asp Ser
            450                 455                 460
Ser Lys Tyr Asn Gln Leu Gln Thr Ile Ala Gln Glu Leu Gly Lys Asn
    465                 470                 475
Pro Phe Arg Arg Phe Gly Val Ile Asp Phe Gln Asn Asn Gly Ala
    480                 485                 490
Met Asn Gly Ile Gly Val Gln Val Gly Tyr Lys Gln Phe Phe Gly Lys
495                 500                 505                 510
Lys Arg Asn Trp Gly Leu Arg Tyr Tyr Gly Phe Phe Asp Tyr Asn His
            515                 520                 525
Ala Tyr Ile Lys Ser Asn Phe Asn Ser Ala Ser Asp Val Trp Thr
            530                 535                 540
Tyr Gly Val Gly Met Asp Ala Leu Tyr Asn Phe Ile Asn Asp Lys Asn
            545                 550                 555
```

```
Thr Asn Phe Leu Gly Lys Asn Asn Lys Leu Ser Val Gly Leu Phe Gly
    560                 565                 570

Gly Phe Ala Leu Ala Gly Thr Ser Trp Leu Asn Ser Gln Gln Val Asn
575                 580                 585                 590

Leu Thr Met Met Asn Gly Ile Tyr Asn Ala Asn Val Ser Thr Ser Asn
                595                 600                 605

Phe Gln Phe Leu Phe Asp Leu Gly Leu Arg Met Asn Leu Ala Arg Pro
            610                 615                 620

Lys Lys Lys Asp Ser Asp His Ala Ala Gln His Gly Ile Glu Leu Gly
        625                 630                 635

Phe Lys Ile Pro Thr Ile Asn Thr Asn Tyr Tyr Ser Phe Met Gly Ala
    640                 645                 650

Lys Leu Glu Tyr Arg Arg Met Tyr Ser Leu Phe Leu Asn Tyr Val Phe
655                 660                 665                 670

Ala Tyr

<210> SEQ ID NO 23
<211> LENGTH: 1149
<212> TYPE: DNA
<213> ORGANISM: Helicobacter pylori
<220> FEATURE:
<221> NAME/KEY: CDS
<222> LOCATION: (106)...(1002)
<220> FEATURE:
<221> NAME/KEY: sig_peptide
<222> LOCATION: (106)...(166)

<400> SEQUENCE: 23
ttactcttta atgtgagttt tctgtgtcat gatagctgat tttgttttaa atttgctata      60
atgtgaattt aatgatgaaa attagtttag agtggagaac acaca atg aaa aaa aat     117
                                                Met Lys Lys Asn
                                                    -20 atc tta aat tta gcg tta gtg ggt gcg ttg agc acg tcg ttt ttg atg       165
Ile Leu Asn Leu Ala Leu Val Gly Ala Leu Ser Thr Ser Phe Leu Met
    -15                 -10                 -5 gct aag ccg gct cat aac gca aat aac gct acg cat aac acg aaa aaa       213
Ala Lys Pro Ala His Asn Ala Asn Asn Ala Thr His Asn Thr Lys Lys
 1               5                  10                  15 acg act gat tct tca gca ggc gtg tta gcg aca gtg gat ggc aga cct       261
Thr Thr Asp Ser Ser Ala Gly Val Leu Ala Thr Val Asp Gly Arg Pro
            20                  25                  30 atc act aaa agc gat ttt gac atg att aag caa cga aat cct aat ttt       309
Ile Thr Lys Ser Asp Phe Asp Met Ile Lys Gln Arg Asn Pro Asn Phe
        35                  40                  45 gat ttt gac aag ctt aaa gag aaa gaa aaa gaa gcc ttg att gat caa       357
Asp Phe Asp Lys Leu Lys Glu Lys Glu Lys Glu Ala Leu Ile Asp Gln
    50                  55                  60 gct att cgc acc gcc ctt gta gaa aat gaa gct aaa acc gag aaa ttg       405
Ala Ile Arg Thr Ala Leu Val Glu Asn Glu Ala Lys Thr Glu Lys Leu
65                  70                  75                  80 gac agc act cca gaa ttt aaa gcg atg atg gaa gcg gtt aaa aaa cag       453
Asp Ser Thr Pro Glu Phe Lys Ala Met Met Glu Ala Val Lys Lys Gln
                85                  90                  95 gct tta gtg gaa ttt tgg gct aaa aaa cag gct gaa gaa gtg aaa aaa       501
Ala Leu Val Glu Phe Trp Ala Lys Lys Gln Ala Glu Glu Val Lys Lys
            100                 105                 110 gtc caa atc cca gaa aaa gaa atg caa gat ttt tac aac gct aac aaa       549
Val Gln Ile Pro Glu Lys Glu Met Gln Asp Phe Tyr Asn Ala Asn Lys
        115                 120                 125
```

```
gat cag ctt ttt gtc aag caa gaa gcc cat gct agg cat att tta gtg        597
Asp Gln Leu Phe Val Lys Gln Glu Ala His Ala Arg His Ile Leu Val
        130                 135                 140 aaa acc gaa gat gag gct aaa cgg att att tct gag att gac aaa cag        645
Lys Thr Glu Asp Glu Ala Lys Arg Ile Ile Ser Glu Ile Asp Lys Gln
145                 150                 155                 160 cca aag gct aaa aaa gaa gct aaa ttc att gag tta gcc aat cgg gat        693
Pro Lys Ala Lys Lys Glu Ala Lys Phe Ile Glu Leu Ala Asn Arg Asp
                165                 170                 175 acg att gat cct aac agc aag aac gcg caa aat ggc ggt gat ttg ggg        741
Thr Ile Asp Pro Asn Ser Lys Asn Ala Gln Asn Gly Gly Asp Leu Gly
            180                 185                 190 aaa ttc caa aag aac caa atg gct ccg gat ttt tct aaa gcc gct ttc        789
Lys Phe Gln Lys Asn Gln Met Ala Pro Asp Phe Ser Lys Ala Ala Phe
        195                 200                 205 gct tta act cct ggg gat tac act aaa acc cct gtt aaa aca gag ttt        837
Ala Leu Thr Pro Gly Asp Tyr Thr Lys Thr Pro Val Lys Thr Glu Phe
    210                 215                 220 ggt tat cat att atc tat ttg att tct aaa gat agc cct gta act tat        885
Gly Tyr His Ile Ile Tyr Leu Ile Ser Lys Asp Ser Pro Val Thr Tyr
225                 230                 235                 240 act tat gaa cag gct aaa cct acc att aag ggg atg tta caa gaa aag        933
Thr Tyr Glu Gln Ala Lys Pro Thr Ile Lys Gly Met Leu Gln Glu Lys
                245                 250                 255 ctt ttc caa gaa cgc atg aat caa cgc att gag gaa cta aga aag cac        981
Leu Phe Gln Glu Arg Met Asn Gln Arg Ile Glu Glu Leu Arg Lys His
            260                 265                 270 gct aaa att gtt atc aac aag taattgatga ggtgttatca tgttagttaa         1032
Ala Lys Ile Val Ile Asn Lys
                275 aggcaatgaa attttattga aagcccataa agaaggttat ggggtggggg cgtttaattt     1092 cgtgaatttt gaaatgctaa acgctatttt tgaagcagga aatgaggaaa attcccc        1149

<210> SEQ ID NO 24
<211> LENGTH: 299
<212> TYPE: PRT
<213> ORGANISM: Helicobacter pylori
<220> FEATURE:
<221> NAME/KEY: SIGNAL
<222> LOCATION: (1)...(20)

<400> SEQUENCE: 24

Met Lys Lys Asn Ile Leu Asn Leu Ala Leu Val Gly Ala Leu Ser Thr
-20                 -15                 -10                 -5

Ser Phe Leu Met Ala Lys Pro Ala His Asn Ala Asn Asn Ala Thr His
            1                   5                   10

Asn Thr Lys Lys Thr Thr Asp Ser Ser Ala Gly Val Leu Ala Thr Val
        15                  20                  25

Asp Gly Arg Pro Ile Thr Lys Ser Asp Phe Asp Met Ile Lys Gln Arg
    30                  35                  40

Asn Pro Asn Phe Asp Phe Asp Lys Leu Lys Lys Glu Lys Glu Ala
45                  50                  55                  60

Leu Ile Asp Gln Ala Ile Arg Thr Ala Leu Val Glu Asn Glu Ala Lys
                65                  70                  75

Thr Glu Lys Leu Asp Ser Thr Pro Glu Phe Lys Ala Met Met Glu Ala
            80                  85                  90

Val Lys Lys Gln Ala Leu Val Glu Phe Trp Ala Lys Lys Gln Ala Glu
        95                  100                 105
```

-continued

```
Glu Val Lys Lys Val Gln Ile Pro Glu Lys Glu Met Gln Asp Phe Tyr
    110             115                 120

Asn Ala Asn Lys Asp Gln Leu Phe Val Lys Gln Glu Ala His Ala Arg
125             130                 135                 140

His Ile Leu Val Lys Thr Glu Asp Glu Ala Lys Arg Ile Ile Ser Glu
                145                 150                 155

Ile Asp Lys Gln Pro Lys Ala Lys Lys Glu Ala Lys Phe Ile Glu Leu
                160             165                 170

Ala Asn Arg Asp Thr Ile Asp Pro Asn Ser Lys Asn Ala Gln Asn Gly
            175             180                 185

Gly Asp Leu Gly Lys Phe Gln Lys Asn Gln Met Ala Pro Asp Phe Ser
    190                 195                 200

Lys Ala Ala Phe Ala Leu Thr Pro Gly Asp Tyr Thr Lys Thr Pro Val
205                 210                 215                 220

Lys Thr Glu Phe Gly Tyr His Ile Ile Tyr Leu Ile Ser Lys Asp Ser
                225                 230                 235

Pro Val Thr Tyr Thr Tyr Glu Gln Ala Lys Pro Thr Ile Lys Gly Met
            240                 245                 250

Leu Gln Glu Lys Leu Phe Gln Glu Arg Met Asn Gln Arg Ile Glu Glu
            255                 260                 265

Leu Arg Lys His Ala Lys Ile Val Ile Asn Lys
    270                 275
```

LT AND CT IN PARENTERAL IMMUNIZATION METHODS AGAINST HELICOBACTER INFECTION

This is a continuation-in-part of U.S. Ser. No. 09/100,258, filed Jun. 19, 1998.

BACKGROUND OF THE INVENTION

This invention relates to methods of immunizing against Helicobacter infection.

Cholera toxin (CT) and the heat-labile-enterotoxin of *E. coli* (LT) are commonly used as immunological adjuvants for mucosal immunization. The non-toxic B subunit of LT (LTB) has also been shown to have mucosal immunomodulating activity. When delivered mucosally with urease or other Helicobacter antigens, LT and CT each induce immune responses that protect mice against infection with *Helicobacter pylori*.

Xu-Amano et al. (J. Exp. Med. 178:1309–1320, 1993) showed that mice develop specific serum IgM and IgG (but not IgA) responses following intraperitoneal immunization with tetanus toxin (TT) plus CT. TT alone gave low responses. Hornquist, et al. (Eur. J. Immunol. 23:2136–2143, 1993) showed that CT promotes priming of CD4+ T cells when delivered intravenously with Keyhole Limpet Hemocyanin (KLH). Marinaro et al. (J. Immunol. 155:4621–4629, 1995) showed that CT stimulates production of serum IgE to TT when the antigen and adjuvant are delivered subcutaneously.

SUMMARY OF THE INVENTION

We have discovered that parenterally delivered LT and LTB are effective adjuvants that enhance the immunoprotective effect of Helicobacter antigens, such as urease. We have also discovered that LT+LTB gives better results that LT alone.

Accordingly, the invention provides methods of inducing a protective or therapeutic immune response to Helicobacter infection in a mammal, in which (a) a Helicobacter antigen, and (b) an adjuvant including one or more of (i) LT, (ii) LTB, (iii) CT, and (iv) CTB (e.g., LT+LTB) is parenterally (e.g., subcutaneously, intradermally, intramuscularly, or intravenously) administered to a mammal.

The antigen and the adjuvant can be provided together in a solution, or separately. The antigen can be urease or a subunit, enzymatically inactivate derivative, or fragment thereof. The antigen can also be catalase, HspA, HspB, lactoferrin receptor, p76 (SEQ ID NOs:1–22), p32 (SEQ ID NOs:23 and 24), BabA, BabB, AlpA, AlpB, or an immunogenic fragment or derivative thereof. The methods of the invention also include the administration of more than one Helicobacter antigen.

The invention provides several advantages. For example, parenteral delivery of LT is advantageous in that the toxin does not contact the intestinal epithelial cells, and thus does not cause diarrhea. Also, the toxicity of parenterally administered LT we observed was limited to injection site swelling, and we observed no toxicity with LTB at high doses (see below), which matched the effectiveness of LT in augmenting protective immunity. Also, our observation of the heightened effect of parenterally administering LT (low dose)+LTB (high dose) minimizes the possibility of any potential side effects.

Other features and advantages of the invention are apparent from the following detailed description, the drawings, and the claims.

DETAILED DESCRIPTION

Figure 1:
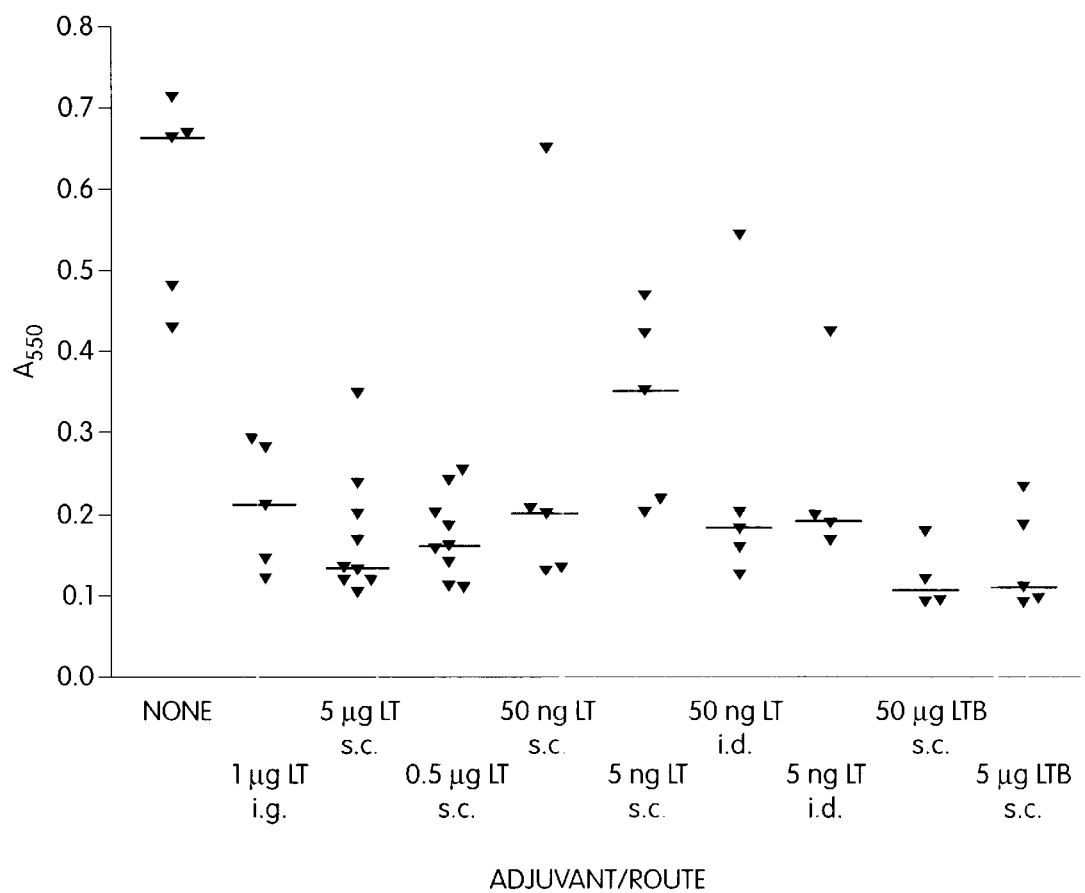
FIG. 1 is a graph showing gastric urease activity measured under treatment and control conditions. Urease activity in samples of mouse stomach tissue was determined by a calorimetric assay. Individual $A_{550}$ values for each mouse (triangles) are shown along with the median value for each group (lines). (See below for further details.)

The methods and compositions of the invention employ several components and techniques, which are described in greater detail as follows.

Antigens

Preferred antigens for use in the invention are Helicobacter (e.g., *H. pylori* or *H. felis*) proteins or other components (e.g., lipopolysaccharides or carbohydrates) that either are purified from bacterial cultures or are produced using standard recombinant or chemical synthetic methods. Preferred antigens are proteins or portions of proteins (i.e., peptides or polypeptides). Methods for identifying immunogenic fragments of polypeptide antigens are known in the art, and can be employed in preparing antigens for use in the methods of the invention (Sturniolo et al., Nature Biotechnology, "Generation of Tissue-Specific and Promiscuous HLA Ligand Databases Using DNA Microarrays and Virtual HLA Class II Matrices," June 1999). Additional antigens that can be used in the invention are whole bacteria and non-purified protein preparations, such as Helicobacter lysates.

The antigens used in the invention can be produced as fusion proteins, i.e., polypeptides containing amino acid sequences corresponding to two or more proteins (or fragments thereof), which are normally separate proteins, linked together by a peptide bond(s). Fusion proteins generally are synthesized by expression of a hybrid gene containing nucleotides encoding each of the individual polypeptides that make up the fusion protein. An example of an antigenic fusion protein included in the invention is one that contains a CT or an LT toxin adjuvant (e.g., toxin A or B subunit, or a fragment or derivative thereof having adjuvant activity) fused to an *H. pylori* antigen, e.g., urease. Another type of fusion protein included in the invention consists of an antigen fused to a polypeptide (e.g., glutathione S-transferase (GST)) that facilitates purification of the fusion protein. Proteins used as antigens in the invention can also be covalently coupled or chemically cross-linked to adjuvants using standard methods.

The most preferred *H. pylori* antigens for use in the invention are urease and derivatives thereof. Most preferred are enzymatically inactive, recombinant multimeric urease complexes, produced as described in Lee et al., WO 96/33732, which is hereby incorporated by reference. A number of other immunogenic *H. pylori* antigens can also be administered according to the invention, e.g., catalase (WO 95/27506), HspA and HspB (WO 94/26901), lactoferrin receptor (WO 97/13784), p76 (SEQ ID NOs:1–22; WO 97/12908), p32 (SEQ ID NOs:23 and 24; WO 97/12909), BabA and BabB (WO 97/47646), AlpA (WO 96/41880), AlpB (WO 97/11182), as well as the antigens described in WO 96/38475, WO 96/40893, WO 97/19098, WO 97/37044, and WO 98/18323. The immunogenic antigens can be used alone (with the adjuvant) or in "cocktails" of two or more antigens.

LT and CT Adjuvants

Any of the known LT or CT adjuvants or variants thereof can be used in the invention. Although the native form can be used (see, e.g., Clements et al., Vaccine 6:269, 1988), and exhibits strong adjuvant activity, it is somewhat toxic, and therefore less toxic mutants are preferred. Several such mutants, having demonstrated adjuvant activity, are described in WO 93/13202, WO 95/17211, and WO 96/06627, which are hereby incorporated by reference. The low-toxicity B subunit (LTB), described in U.S. Pat. Nos. 5,308,835, 5,079,165, 4,808,700, and 5,182,109, which are hereby incorporated by reference, is also efficacious.

The invention can also employ LT or CT toxoids as adjuvants. A toxoid is a toxin that has been treated so as to destroy or decrease its toxic properties, but to retain adjuvant activity. Toxoids included in the invention are made using standard methods including, but not limited to, chemical (e.g., formaldehyde or glutaraldehyde) treatment, protease cleavage, and recombinant methods (e.g., by making fragments or mutations (e.g., point mutations) of the toxin(s)). DNA encoding LT or CT toxin subunit or toxoid in an appropriate expression vector can also be used. CT and LT are further described, for example, by Spangler (Microbiological Reviews 56(4):622–647, 1992).

Vaccine Formulation

Generally, the *H. pylori* antigen(s) and adjuvant are admixed together in a pharmaceutically acceptable carrier, e.g., water, saline, or phosphate-buffered saline. The concentration of *H. pylori* antigen in the composition preferably is between 10 $\mu$g and 1 mg, advantageously from 25 $\mu$g to 500 $\mu$g, preferably from 50 $\mu$g to 200 $\mu$g, and most preferably a single dose contains about 100 $\mu$g antigen. The concentration of LT or CT adjuvant in the composition preferably is between 1 $\mu$g and 100 $\mu$g, and the concentration of LTB or CTB subunit or toxoid is preferably between 1 $\mu$g and 1 $\mu$g, for example, between 10 $\mu$g and 50 $\mu$g.

Administration

The compositions of the invention are administered parenterally; i.e., the composition is injected subcutaneously, intramuscularly, intravenously, intradermally, or by any other non-mucosal modality. The LT or CT adjuvant can be administered in an encapsulated form or in an unencapsulated form (i.e., in solution).

The methods of the invention can be used both for treatment and prevention of *H. pylori* infection. For prevention, the composition is injected into the patient at intervals of one week to six months for a period of between one and six months, at a dosage of 0.05 to 5 mg/kg *H. pylori* antigen. Where the patient has an *H. pylori* infection that is to be treated, injections at intervals of one week to six months, for one to six months, are administered, for 0.05 to 5 mg/kg *H. pylori* antigen. Antibiotics can be administered as an adjunct to the immunotherapy of the invention.

The following experimental results support the methods of the present invention.

Results

Characterization of recombinant LT and LTB. LT and LTB were tested for toxicity using a Y-1 cell-rounding assay (Chapman et al., J. Med. Microbiol. 18:399–403, 1984). LT was tested before and after treatment with trypsin, which activates the toxin by cleavage of the A subunit. The dose of untreated LT required for 50% cell rounding (ED50) was 0.2 ng/ml. Following trypsin treatment, the ED50 fell to 0.1 ng/ml, indicating that approximately 50% of the LT was active prior to trypsin treatment. LTB had no activity in the assay when tested at concentrations up to 100 $\mu$g/ml.

Adjuvant effects of parenterally delivered LT and LTB for protection against *H. pylori* challenge. Mice were immunized subcutaneously or intradermally with 10 µg of *H. pylori* urease mixed with 5 ng to 5 µg of recombinant LT or 5 µg to 50 µg of recombinant LTB (see Table 1). As a positive control, mice were immunized orally or intragastrically with 25 µg of urease plus 1 µg LT, a regimen shown previously to protect against *H. pylori* challenge (Ermak et al., J. Exp. Med. 188:2277–2288, 1998). A schedule of 3 immunizations, with a two-week interval between doses was used. Mice injected subcutaneously with the two higher doses of LT (0.5 and 5 µg) developed swelling at the injection site that was still present two weeks after the first immunization. As a result, the second dose was omitted in these 2 groups and a single boosting immunization was given 4 weeks after the first dose, at which point the swelling had subsided. Injection site swelling consisted of a raised area approximately 1 cm in diameter with no skin color change or necrosis apparent. No other signs of toxicity were observed. Mice injected intradermally with 0.5 or 5 µg of LT also experienced injection site swelling. Because swelling did not subside as quickly in these mice, further immunization was not performed and the mice were removed from the study. Two weeks after the final immunization, mice were challenged intragastrically with mouse-adapted *H. pylori* strain X47-2AL. Gastric colonization was assessed two weeks after challenge by determining urease activity and bacterial CFU.

Gastric urease activity results are shown in FIG. 1. $A_{550}$ values for individual mice and the median for each group are shown. Some groups contain fewer than 10 data points, due to a technical problem with the assay. Mice in the unimmunized group were clearly infected ($A_{550} \geq 0.20$), with a median $A_{550}$ of 0.67. Mice immunized intragastrically with urease plus LT (positive control) had a median $A_{550}$ of 0.21, with substantial reductions in gastric *H. pylori* colonization in all mice. A similar effect was seen in mice immunized subcutaneously with urease plus LT at the two highest doses (5 and 0.5 µg). The lower doses of LT (50 and 5 ng) were somewhat less effective. Intradermal immunization with urease and LT result in similar levels of protection. Subcutaneous immunization with urease plus 50 µg LTB resulted in the lowest median $A_{550}$ value of any of the groups.

Figure 2:
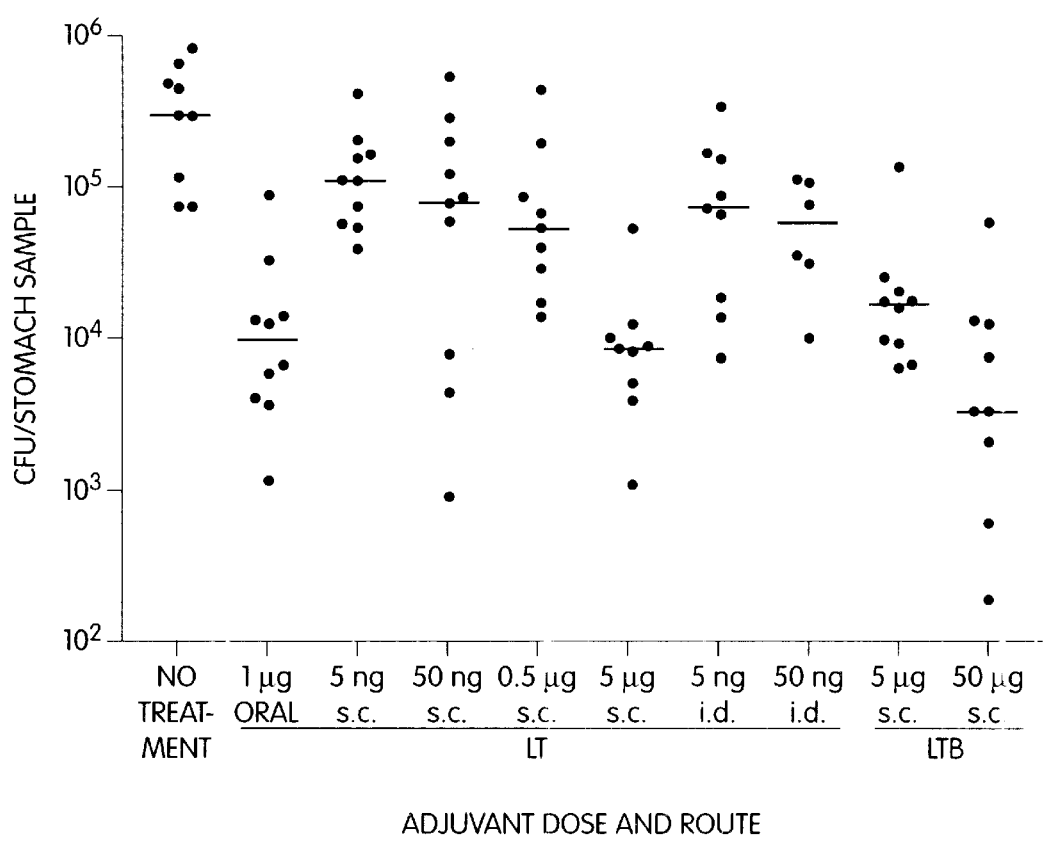
FIG. 2 is a graph showing quantitative culture measurements made under treatment and control conditions. Samples of mouse stomach tissue were homogenized and cultured to determine the number of colony-forming units (CFU) per sample. Individual counts for each mouse (circles) are shown along with the median for each group (lines). (See below for further details.)

Results of quantitative culture of gastric tissue mirrored those of the urease assay (FIG. 2). The highest subcutaneous doses of LT and LTB resulted in a level of protection equal to that afforded by intragastric immunization. Lower doses had lesser effects. More specifically, the median level of gastric *H. pylori* colonization in unimmunized mice was $2.9 \times 10^5$ CFU/stomach sample (FIG. 2). In mice immunized orally with urease plus LT, the median level was $9.1 \times 10^3$ CFU/sample, a significant reduction in colonization (P=0.0004) that was consistent with previous experiments using the X47-2AL challenge strain (26, 38). Subcutaneous delivery of urease with the highest dose of LT (5 µg) was as effective at reducing infection as oral immunization, resulting in a significantly reduced median *H. pylori* level of $8.3 \times 10^3$ CFU/sample (FIG. 2). Subcutaneous delivery of urease with lower doses of LT reduced gastric colonization to a lesser, but significant (P<0.05) extent. Intradermal injection of urease with 5 ng or 50 ng of LT was similar in effectiveness to subcutaneous delivery of the same doses. Subcutaneous delivery of urease with 50 µg of LTB reduced the median level of *H. pylori* to $3.2 \times 10^3$ CFU/sample, the lowest level in any of the groups. A lesser but significant effect (P=0.0006) was seen when only 5 µg of LTB was used.

Figure 3:
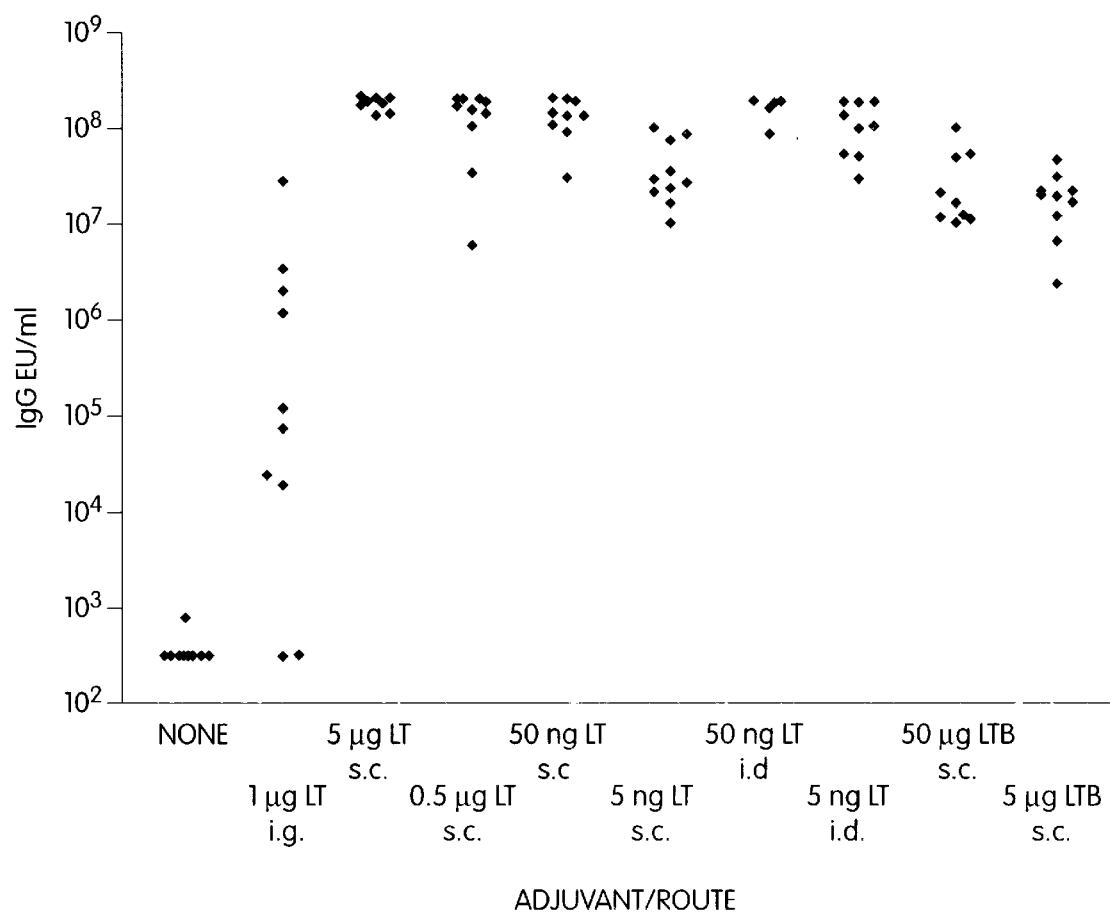
FIG. 3 is a graph showing anti-urease serum IgG measurements made under treatment and control conditions. Post-immunization sera were tested for IgG antibody against urease by ELISA. IgG levels in ELISA units (EU) per ml for individual mice are shown.

All mice developed IgG to urease in serum following immunization (FIG. 3). Responses in parenterally immunized mice were higher than those of intragastrically immunized mice. In groups receiving LT parenterally, there was a trend towards lower IgG responses with lower doses. Mice immunized with urease plus LTB had somewhat lower responses than mice immunized with urease plus LT.

Figure 4:
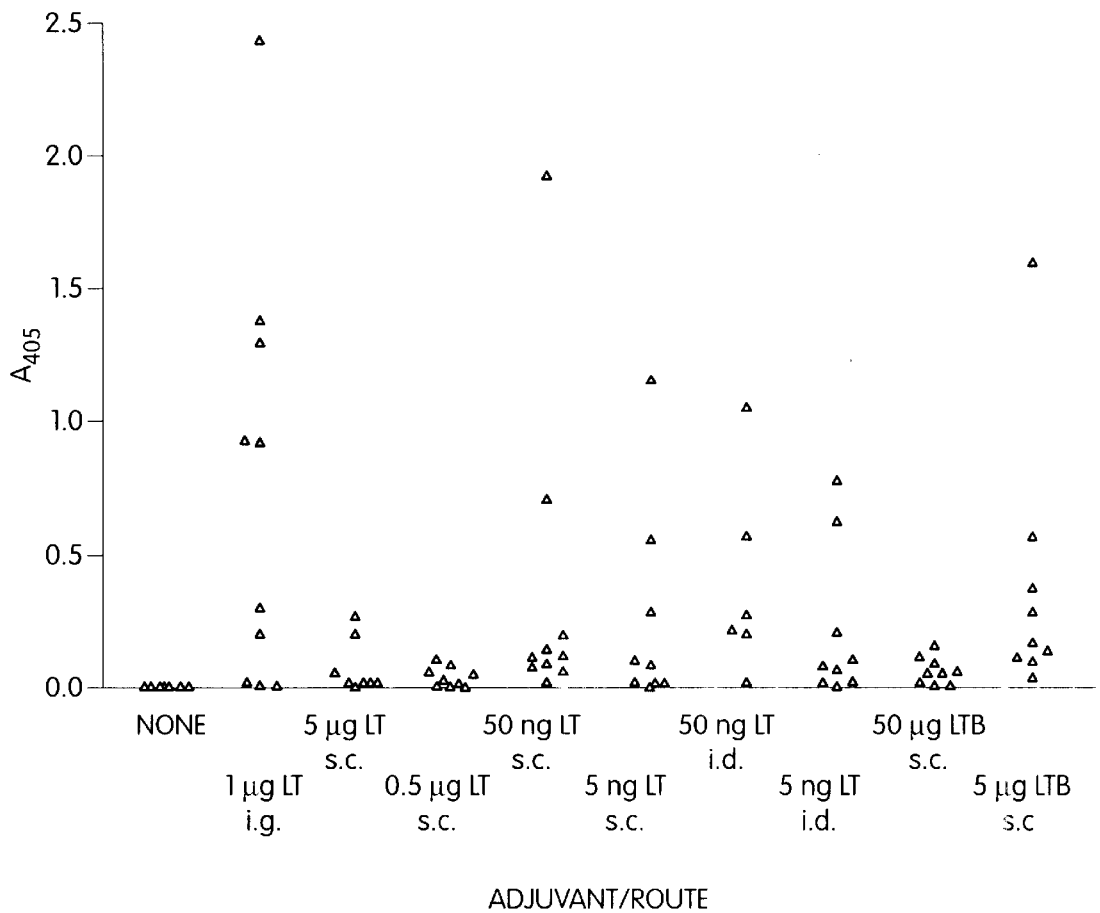
FIG. 4 is a graph showing anti-urease salivary IgA measurements made under treatment and control conditions. Post-immunization saliva samples were diluted 1:10 and tested for IgA antibody against urease by ELISA. $A_{405}$ values for individual mice are shown.

Salivary IgA to urease was highest in the intragastrically immunized group, although 3 of 10 mice did not respond (FIG. 4). Other immunized groups had a range of IgA responses. In mice immunized with urease plus LT subcutaneously, the highest responders were in the groups treated with the two lowest doses of LT (50 and 5 ng). Intradermal immunization with urease plus 50 or 5 ng LT stimulated salivary IgA in most mice. LTB immunization resulted in IgA responses primarily in the lower dose group.

The results show that mucosally or parenterally delivered LT acts as an effective adjuvant for immunization of mice against *H. pylori* infection. Surprisingly, parenteral LT stimulated a secretory IgA response against urease. In previous experiments, we found that subcutaneous injection of urease, alone or adsorbed to alum adjuvant, elicited little or no salivary IgA response.

Figure 5:
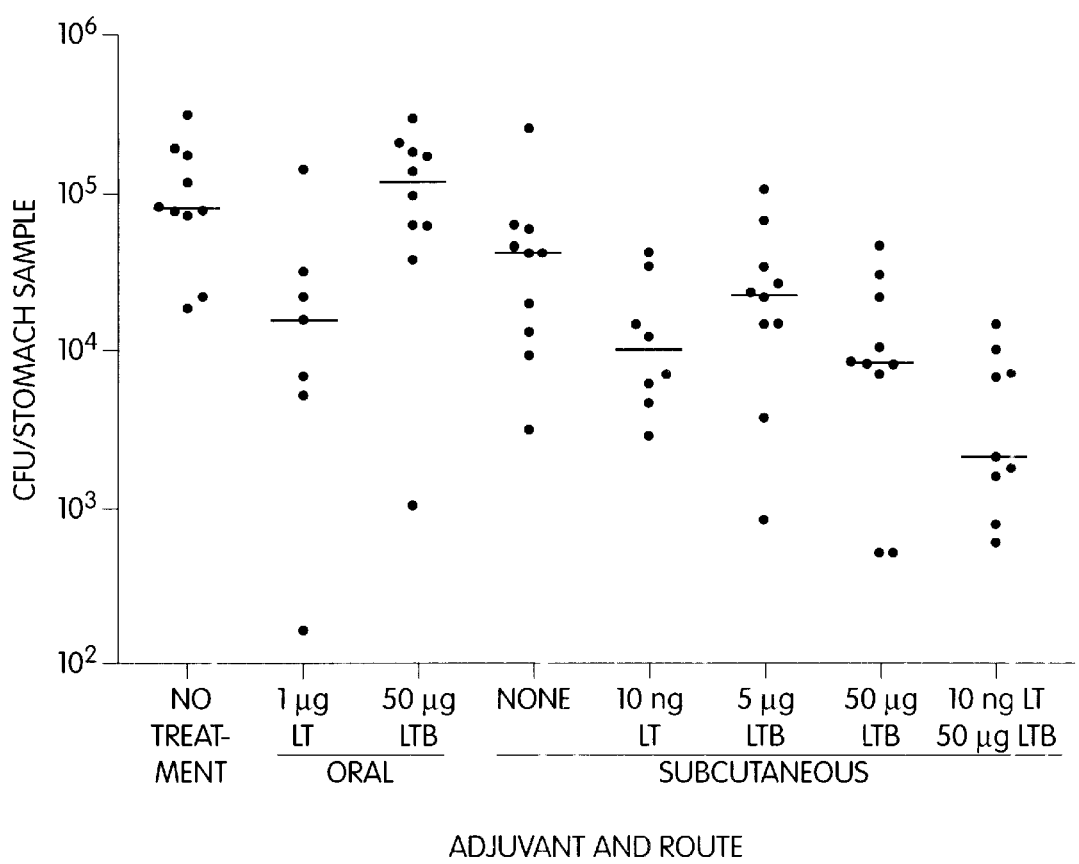
FIG. 5 is a graph showing gastric *H. pylori* colonization in mice following oral or subcutaneous immunization with urease alone or mixed with LT or LTB. Mice were either unimmunized (no treatment) or immunized 3 times with urease plus the adjuvants shown and challenged with *H. pylori* orally 2 weeks after the final immunization. For oral immunization, 25 µg of urease was delivered with 1 µg of LT. For subcutaneous immunization, 10 µg urease was delivered with the dose of adjuvant shown. Symbols show the CFU per quarter antrum of individual mice. The horizontal lines show the median for each group.

Adjuvant effects of orally delivered LTB and parenterally delivered LT-LTB mixture. A second experiment, using the same immunization schedule and challenge procedure as described above, was designed to examine several questions regarding the adjuvant activities of LT and LTB with urease, including whether LTB was active orally, whether subcutaneously delivered urease was protective without LT or LTB, and whether a combination of LT and LTB was more effective than either molecule alone. As shown in FIG. 5, oral delivery of urease plus 1 µg LT reduced gastric colonization to a median level of $1.5 \times 10^4$ CFU/sample from a median of $7.9 \times 10^4$ CFU/sample in untreated mice (P=0.02). Oral delivery of urease with 50 µg of LTB, however, had no effect on colonization (P=0.82). Subcutaneous immunization with urease alone reduced the median *H. pylori* level slightly from that of unimmunized mice (P=0.02) and addition of LT or LTB enhanced the protective effect (P≦0.01). As in the previous experiment, LTB was more effective at the higher dose (50 µg) than at the lower dose (5 µg). Administration of 50 µg of LTB in the absence of urease had no effect on colonization. The greatest effect was seen when a mixture of 50 µg LTB and 10 ng LT was used as adjuvant for subcutaneous immunization. In this group, colonization was reduced to $2.1 \times 10^3$ CFU/sample (P=0.0002).

Figure 6:
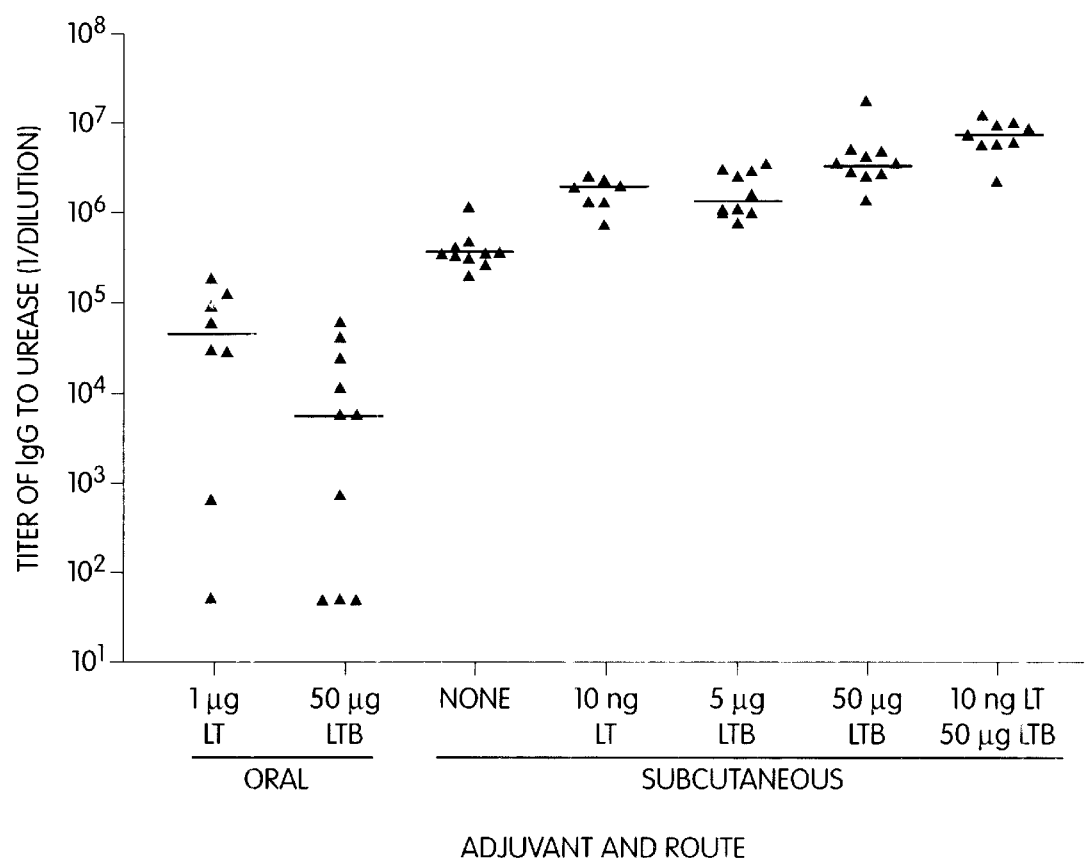
FIG. 6 is a graph showing titers of IgG to urease in sera of immunized mice. Mice were immunized 3 times orally or subcutaneously with urease plus the adjuvants shown. Serum was collected 1 week after the final immunization and. tested for urease-specific IgG by ELISA. Endpoint titers for individual mice are shown. Samples in which no specific antibody was detected were assigned a titer of 50. The horizontal lines show the median titer for each group.

Antibody responses to urease following parenteral delivery of urease with LT or LTB adjuvants. Serum and saliva collected after immunization, but before *H. pylori* challenge, were examined to determine the effects of different adjuvants and routes of immunization on the magnitude and type of antibodies elicited against urease. IgG to urease was not detected in the serum of unimmunized mice when tested at a 1/100 dilution. Oral immunization with urease plus LT elicited low to moderate titers of urease-specific IgG (FIG. 6). IgG titers were similar when mice were immunized orally using LTB as adjuvant. In serum from subcutaneously immunized mice, IgG levels in all groups were higher than those obtained with oral immunization and responses were more uniform within each group. Subcutaneous immunization with urease alone resulted in IgG titers of greater than 5 $\log_{10}$, while the addition of LT or LTB increased titers several fold (P=0.06 and P<0.005, respectively, comparing the LT and LTB groups against the no-adjuvant group). As with protection, co-administration of LT and LTB had an additive effect, resulting in a urease-specific IgG titer of 6.9 $\log_{10}$, a 20-fold increase over the median titer in mice immunized with urease in the absence of adjuvant (P=0.002).

Analysis of serum IgG1 and IgG2a levels showed differences in the quality of the urease-specific IgG response among different groups (Table 2). In comparison to subcutaneous immunization, oral immunization tended to elicit lower levels of both IgG1 and IgG2a and a lower IgG1/IgG2a ratio, whether LT or LTB was delivered with urease. In contrast, subcutaneous LT and LTB elicited IgG responses to urease that were qualitatively different from each other. Subcutaneous delivery of urease alone elicited strong IgG1 and IgG2a responses, and the levels of both isotypes were enhanced by addition of LT or LTB. However, LT stimulated a greater increase in IgG1 than in IgG2a, while LTB stimulated a greater increase in IgG2a than in IgG1. When LT and LTB were delivered together, the effect of LTB appeared to be dominant, since the median IgG2a titer of 6.7 $\log_{10}$, was nearly 80-fold higher than that of mice receiving urease without adjuvant and the highest of any group.

Figure 7:
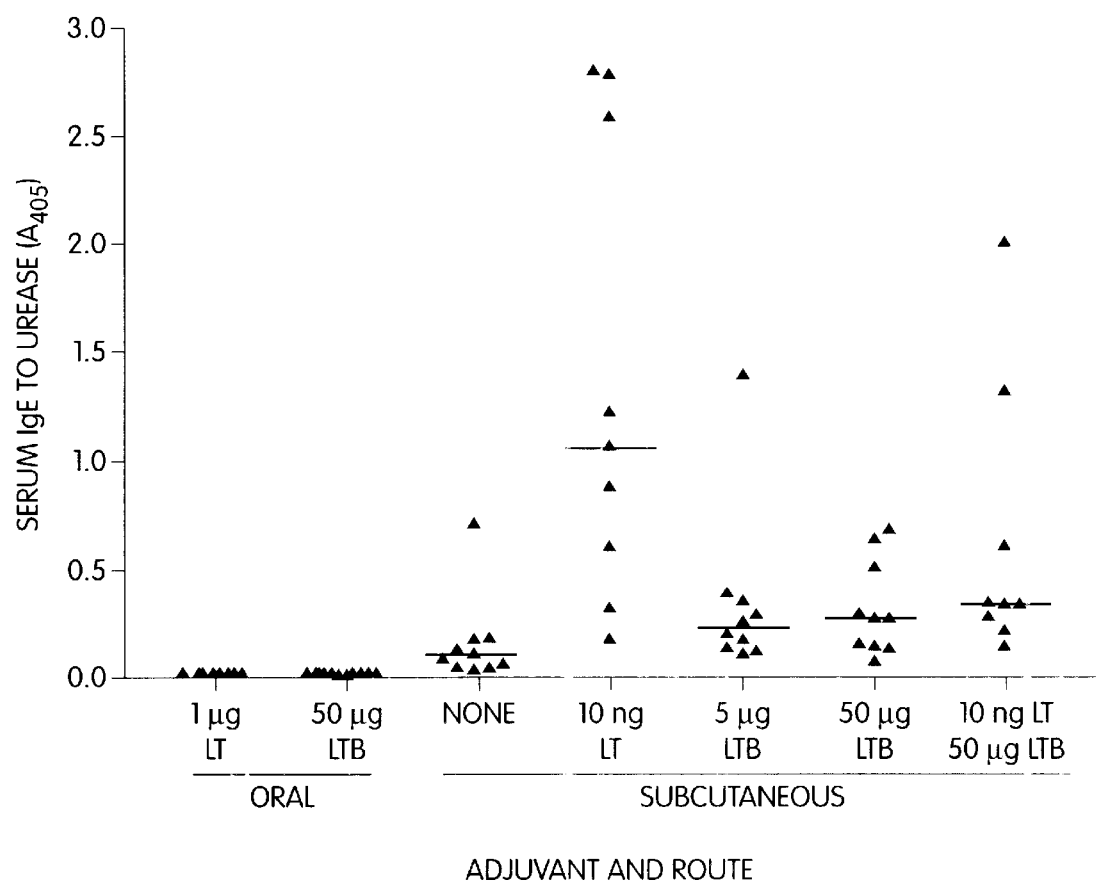
FIG. 7 is a graph showing IgE to urease in sera of immunized mice. Mice were immunized 3 times orally or subcutaneously with urease plus the adjuvants shown. Serum was collected 1 week after the final immunization and tested for urease-specific IgE at a 1/100 dilution by ELISA. Absorbance values for individual mice are shown. The horizontal lines show the median value for each group.

Serum IgE to urease was generated only by parenteral immunization (FIG. 7). Subcutaneous immunization with urease alone stimulated a low level IgE response in most mice. The addition of LT adjuvant increased IgE levels, although responses were highly variable. The median IgE response in mice receiving LTB adjuvant was only slightly higher than that of mice receiving no adjuvant. LT and LTB together led to levels that were somewhat higher than those seen with LTB alone.

Figure 8:
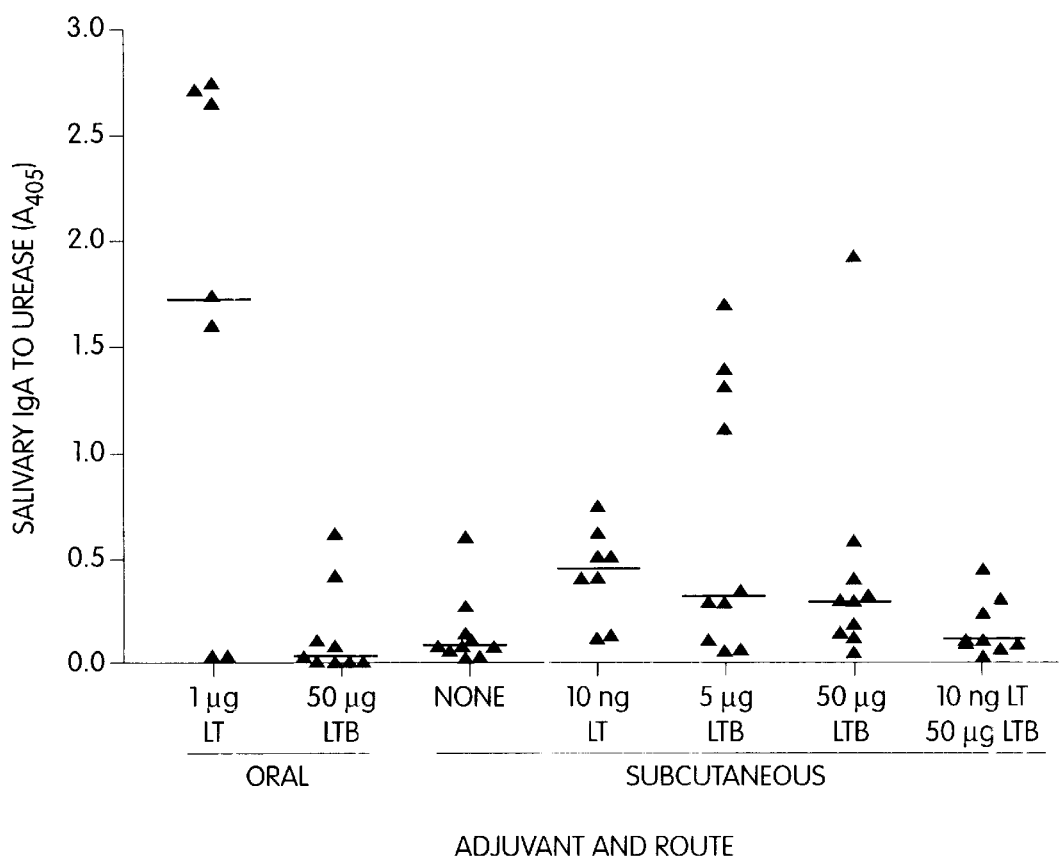
FIG. 8 is a graph showing IgA to urease in saliva samples of immunized mice. Mice were immunized 3 times orally or subcutaneously with urease plus the adjuvants shown. Saliva was collected 1 week after the final immunization and tested for urease-specific IgA at a 1/10 dilution by ELISA. Absorbance values for individual mice are shown. The horizontal lines show the median value for each group.

IgA to urease in saliva was greatest when mice were immunized orally and LT adjuvant was used, although not all mice had a detectable IgA response (FIG. 8). Delivery of urease orally with LTB or subcutaneously without adjuvant stimulated only low levels of specific IgA in saliva. LT stimulated low levels of specific IgA in the saliva of most mice when delivered subcutaneously with urease, while LTB had a similar effect but also induced moderate levels of salivary IgA in several mice. When LT and LTB were delivered together, specific salivary IgA was not increased over the level seen when mice were immunized with urease alone.

Figure 9:
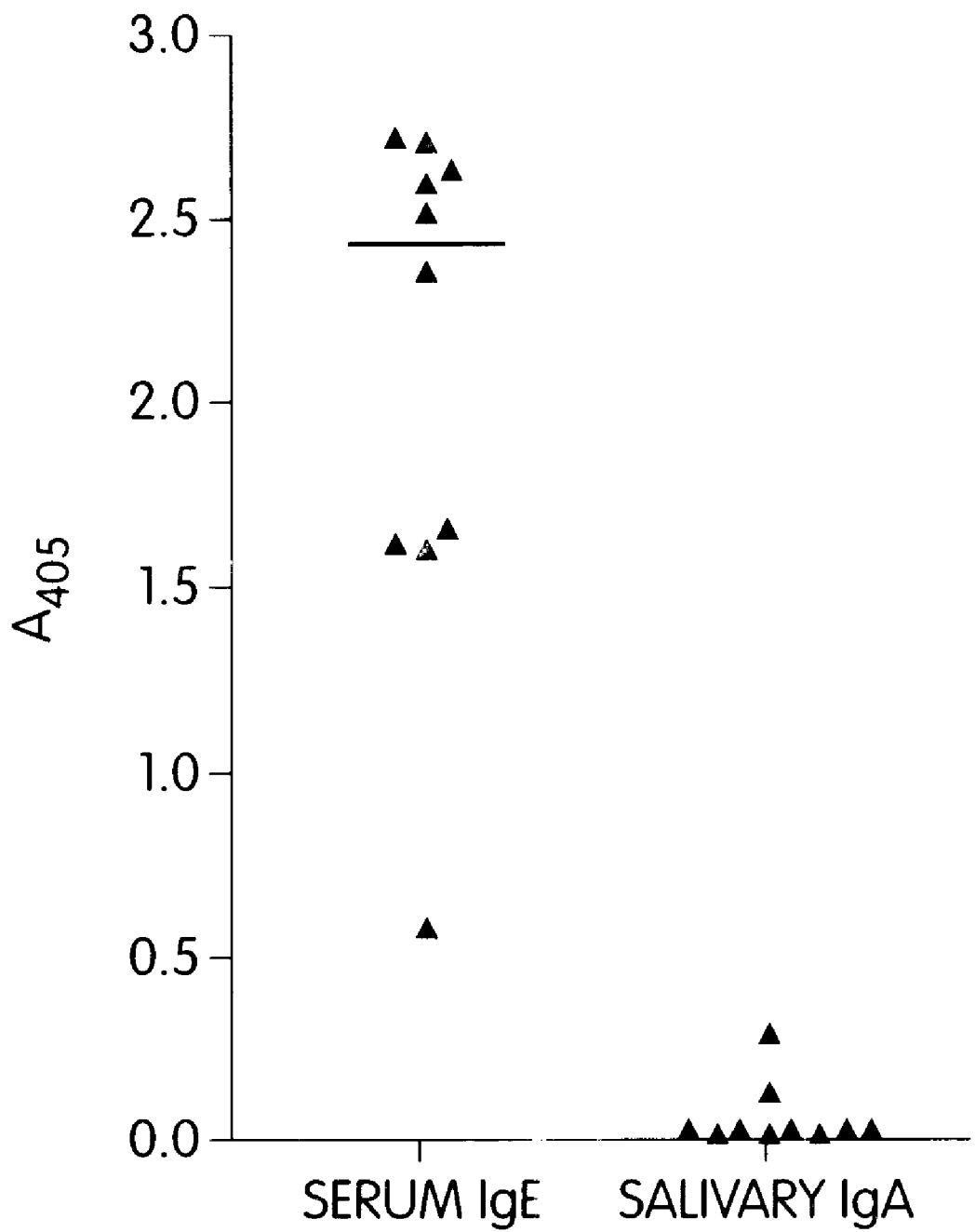
FIG. 9 is a graph showing urease-specific IgE in serum and IgA in saliva of mice immunized 3 times subcutaneously with urease adsorbed to alum adjuvant. Serum and saliva were collected 1 week after the final immunization and tested for urease-specific antibody by ELISA. Absorbance values for individual mice are shown. The horizontal lines show the median value for each group.

Antibody responses to urease following parenteral delivery of urease with alum adjuvant. To compare the adjuvant activities of LT and LTB with a more conventional parenteral adjuvant, mice were immunized subcutaneously with urease adsorbed to alum (aluminum hydroxide) adjuvant. As in the experiments described above, mice were immunized 3 times and blood and saliva were collected 1 week after the final immunization. This regimen was shown previously to reduce colonization of the stomach following *H. pylori* challenge, but was less effective than oral immunization with urease plus LT (Ermak et al., J. Exp. Med. 188:2277–2288, 1998). The titer of specific IgG in serum following immunization with urease adsorbed to alum ranged from 5.7 to 7.1 $\log_{10}$, with a median of 6.3 $\log_{10}$. This was the same approximate level of serum IgG elicited by subcutaneous delivery of urease plus LT or LTB. The median titers of IgG1 and IgG2a in serum following urease plus alum immunization were 6.6 and 5.5, respectively (Table 2). IgG1/IgG2a ratios were relatively high, ranging from 3.9 to 53.2. This range was similar to that obtained with subcutaneous delivery of urease alone or with LT. IgE levels were higher with alum than with LT or LTB as adjuvant, with $A_{405}$ values for urease-specific IgE exceeding 2.0 in over half of the mice that received alum (FIG. 9). Only slight salivary IgA responses were stimulated with alum as adjuvant (FIG. 9).

Figure 10:
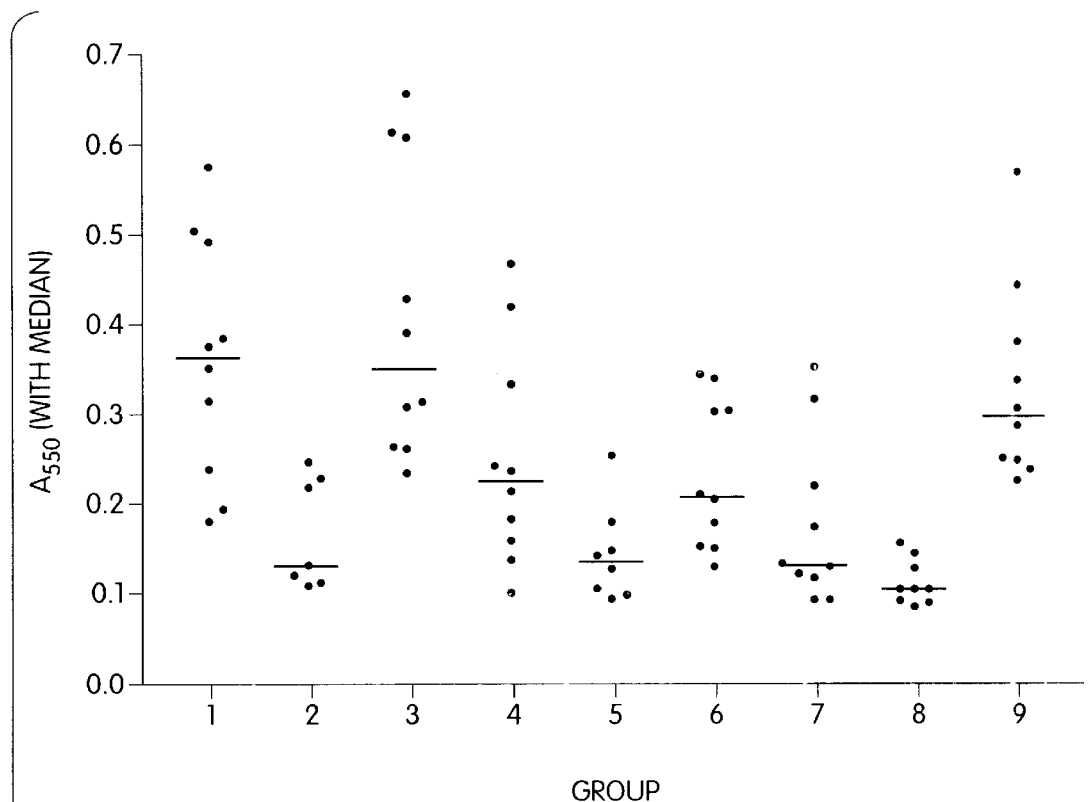
FIG. 10 is a graph showing gastric urease activity measured under treatment and control conditions. Urease activity in samples of mouse stomach tissue was determined by a calorimetric assay. Individual $A_{550}$ values for each mouse (circles) are shown along with the median value for each group (lines). (See below for further details.)
Figure 11:
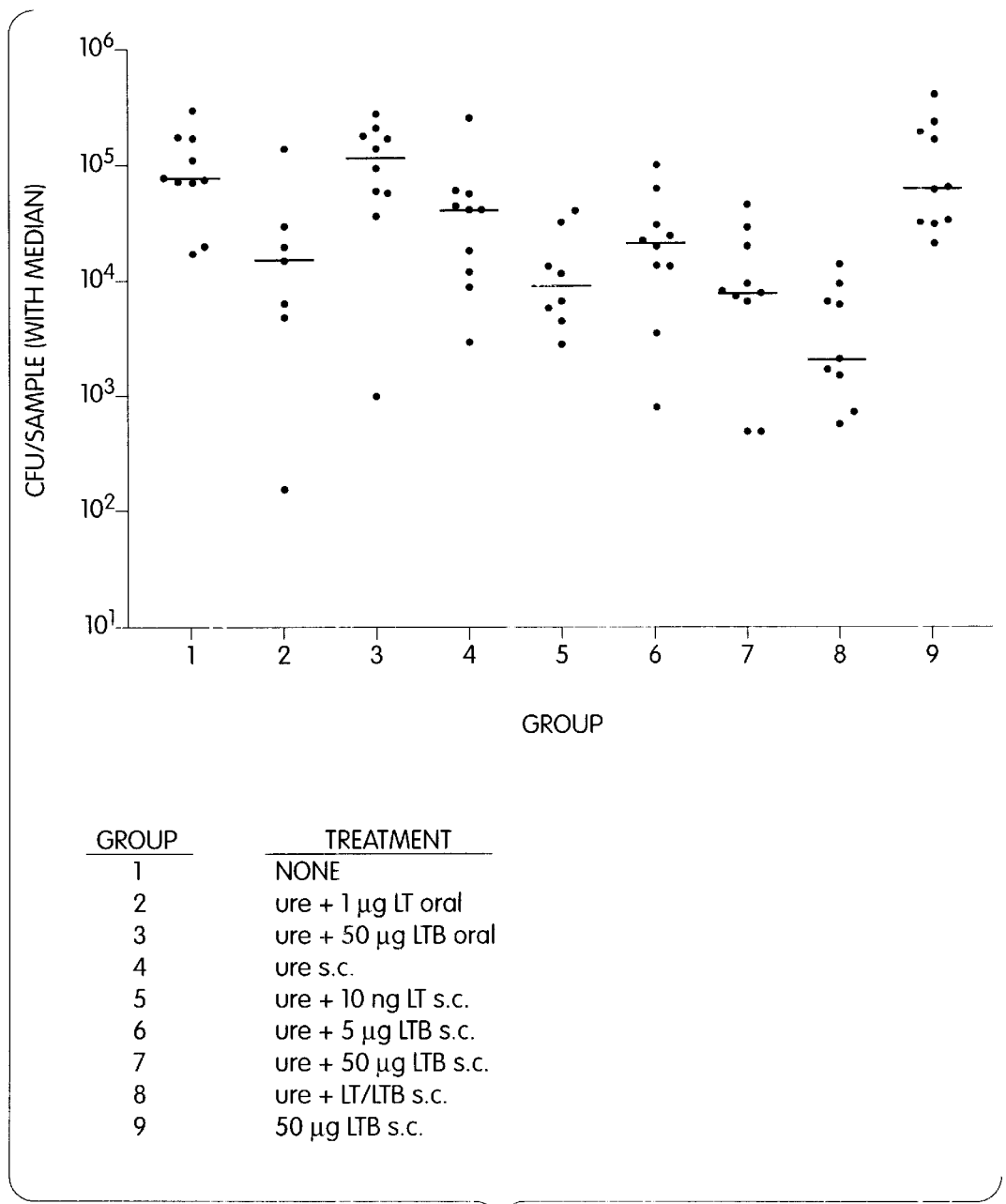
FIG. 11 is a graph showing quantitative culture measurements made under treatment and control conditions. Samples of mouse stomach tissue were homogenized and cultured to determine the number of colony-forming units (CFU) per sample. Individual counts for each mouse (circles) are shown along with the median for each group (lines). (See below for further details.)

Additional data supporting these findings is shown in FIGS. 10 and 11. In these experiments, groups of 10 mice each were immunized on days 0, 14, and 28, as follows: no antigen, no adjuvant (group 1); 25 µg urease, 1 µg LT, orally (group 2); 25 µg urease, 50 µg LTB, orally (group 3); 10 µg urease, no adjuvant, s.c. (group 4); 10 µg urease, 10 ng LT, s.c. (group 5); 10 µg urease, 5 µg LTB, s.c.(group 6); 10 µg urease, 50 µg LTB, s.c. (group 7); 10 µg urease, 10 ng LT, 50 µg LTB, s.c. (group 8); and no antigen, 50 µg LTB, s.c. (group 9). The groups were challenged with $1 \times 10^7$ *H. pylori* CFU at day 42. At day 56, mice were sacrificed and the gastric colonization was assessed by testing stomach samples for urease activity (Jatrow test) and *H. pylori* culture. As is shown in FIGS. 10 and 11, 10 ng LT and 50 µg LTB given subcutaneously with urease (groups 5 and 7) similarly lead to a significant reduction of the infection rate, compared to controls (groups 1 and 9). These results are as good as those obtained with urease +1 µg LT given orally (group 5); 10 ng LT +50 µg LTB (group 7), give even better results.

The results described above were obtained using the following materials and methods.

Materials and Methods

Antigens and adjuvants. Recombinant *H. pylori* urease was expressed in *E. coli* strain ORV214 and purified by anion-exchange and gel filtration chromatography as described previously (Lee et al., J. Infect. Dis. 172:161–172, 1995). Endotoxin concentration, as determined by the Limulus amoebocyte lysate assay, was reduced to 1.5 ng/mg urease using a Sartobind matrix (Sartorius Corporation, N.Y.). Recombinant LT was obtained from Berna Products Corp. (Coral Gables, Fla.). For trypsin cleavage, 100 µg of LT was mixed with 1 µg of bovine pancreas trypsin (Sigma Chemical Co., St. Louis, Mo.) in 200 µl phosphate buffered saline (PBS) and incubated for 60 minutes at 37° C. Enzymatic activity was stopped by addition of 100 µg of soybean trypsin inhibitor (Sigma). Recombinant LTB was cloned and expressed in *E. coli*.

B subunit was purified from lysates by galactose affinity chromatography which yielded a product consisting of greater than 90% pentameric LTB. Endotoxin was removed using a Sartobind matrix. Purified LTB was lyophilized and stored.

Y-1 cell rounding assay. Toxicity of LT and LTB was assessed with a modified cell rounding assay (Chapman et al., J. Med. Microbiol. 18:399–403, 1984). In brief, 96-well flat bottom tissue culture plates were seeded with Y-1 mouse adrenal cells at $2 \times 10^4$ cells/well in minimum essential medium supplemented with 10% fetal bovine serum. Following incubation at 37° C. in 5% $CO_2$ for $\geq 2$ hours to allow spreading of cells on the substrate, medium was removed from wells and replaced with medium containing serial two-fold dilutions of LT or LTB and plates returned to the incubator. After overnight incubation at 37° C., the cells were viewed with an inverted microscope. The toxin potency was defined as the lowest concentration at which $\geq 50\%$ of cells were rounded (50% effective dose or ED50).

Immunization and sampling. Procedures involving animals were approved by the Institutional Animal Care and Use Committee of OraVax, Inc. Specific pathogen-free, 6 to 8 week-old female Swiss-Webster mice were purchased from Taconic Laboratories (Germantown, N.Y.). Mice were immunized with urease via the oral, subcutaneous or intradermal routes. Three doses were given with a 2-week interval between doses. For oral immunization, 25 $\mu$g of urease and 1 $\mu$g of LT in a volume of 25 $\mu$l was pipetted into the mouth. For subcutaneous immunization, 10 $\mu$g of urease was injected in the lower back, with or without LT, LTB or aluminum hydroxide (alum) adjuvant, in a volume of 100 $\mu$l. Equal volumes of alum (Rehydragel, Reheis, Inc., Berkeley Heights N.J.) at 2 mg/ml and urease at 100 $\mu$g/ml were mixed 30–60 minutes prior to injection. For intradermal immunization, a patch of skin on the back was shaved, the mice were anesthetized by isoflurane inhalation, and 10 $\mu$g urease with LT or LTB adjuvant was delivered via a 30 gauge needle in a volume of 50 $\mu$l.

Blood and saliva were sampled approximately 1 week after the third immunization. Blood was collected from the retro-orbital sinus while mice were under isoflurane inhalation anesthesia, and saliva was collected from the mouth with a micropipette after intraperitoneal injection of 70–100 $\mu$g of pilocarpine.

Challenge and analysis of colonization. Approximately 2 weeks after the final immunization, mice were challenged intragastrically with a single dose of 1×10$^7$ live streptomycin-resistant *H. pylori* strain X47-2AL (Kleanthous et al., Infect. & Immun. 66:2879–2886, 1998). Challenge bacteria were grown first on Mueller-Hinton agar plates containing 10% sheep blood and transferred to Brucella broth as described previously (Kleanthous et al., Infect. & Immun. 66:2879–2886, 1998). The challenge dose was delivered intragastrically in a volume of 100 $\mu$l using a blunt-tipped feeding needle. Mice were sacrificed 2 weeks after challenge to assess gastric colonization by *H. pylori*. The stomach was removed, rinsed with 0.9% NaCl solution, and cut open along the lesser and greater curvatures. One quarter of the antrum was placed into 1 ml of Brucella broth supplemented with 5% calf serum and disrupted using a Dounce homogenizer fitted with a loose pestle. Tenfold dilutions of homogenate were inoculated onto Mueller-Hinton agar containing 10% sheep blood, 5 $\mu$g/ml amphotericin B, 5 $\mu$g/ml trimethoprim, 10 $\mu$g/ml vancomycin, 10 U/ml polymyxin B sulfate, and 50 $\mu$g/ml streptomycin. Plates were incubated at 37° C. in 7% $CO_2$ and colonies counted 5–7 days later.

Antibody analysis. Antibody responses in serum and saliva were measured by enzyme-linked immunosorbent assay (ELISA). Flat-bottom 96-well plates were coated overnight at 4° C. with 0.5 $\mu$g urease per well in 100 $\mu$l of 0.1 M carbonate buffer, pH 9.6. Wells were washed with PBS containing 0.05% Tween 20 (PBS-Tween), and PBS-Tween containing 2.5% nonfat dry milk (blocking buffer) was added to block nonspecific binding. Blocking buffer was used as diluent for test samples and antibody conjugates. Samples and reagents were added to wells in 100 $\mu$l volumes and wells were washed with PBS-Tween between steps. For IgG, IgG1, and IgG2a determination, serum was diluted 1/100 and then further diluted with a series of five-fold dilutions. After removing blocking buffer, 100 $\mu$l of each dilution was added in duplicate and plates were incubated for 60 minutes at 28° C. Biotin-conjugated goat anti-mouse IgG, IgG1, or IgG2a antibodies (Southern Biotechnology Associates, Birmingham Ala.), each diluted 1/1000, were added to wells next and plates were incubated for. 60 minutes at 28° C. Streptavidin-alkaline phosphatase (Calbiochem, La Jolla Calif.) diluted 1/500 was added next and plates were incubated for 30 minutes at 28° C. For the final step, 100 $\mu$l of 1 mg/ml p-nitrophenyl phosphate substrate (Sigma) in 1 M diethanolamine buffer, pH 9.6 containing 5 mM $MgCl_2$ was added. Plates were incubated for 20 minutes at room temperature and the $A_{405}$ read with a Vmax microplate reader (Molecular Devices, Menlo Park, Calif.). The average absorbance value of duplicate wells was plotted and a curve was fit to the data points using the power function of Cricket Graph III software (Computer Associates International, Inc., Islandia N.Y.) running on an Apple Macintosh computer. The titer of each sample was defined as the reciprocal of the dilution corresponding to an $A_{405}$ of 0.1, which was approximately 3 times the background absorbance for normal mouse serum at a 1/100 dilution. Samples with an $A_{405}$ less than 0.1 at a 1/100 dilution were assigned a titer of 50. For determination of salivary IgA levels, saliva was tested at a single dilution of 1/10 and the results are reported as the average $A_{405}$ for duplicate wells. The assay procedure for IgA determination was otherwise as described above except that goat anti-mouse IgA biotin conjugate (Southern Biotechnology) was used to detect bound salivary IgA antibodies.

For quantitation of IgE to urease, a capture ELISA was used. Flat-bottom 96-well plates were coated overnight with 100 $\mu$l of rat monoclonal antibody clone 23G3 against mouse IgE (Southern Biotech) at a concentration of 1 $\mu$/ml. Wells were washed and blocked with nonfat milk as described above and 100 $\mu$l of mouse serum, diluted 1/100 was added to wells in duplicate. Following incubation for 1 hour at 28° C., the plates were washed and urease, at 2.5 $\mu$g/ml, was added to wells. Plates were again incubated for 1 hour at 28° C. In subsequent steps, wells were treated with rabbit anti-urease diluted 1/4000 and goat anti-rabbit IgG conjugated to alkaline phosphatase at a 1/2000 dilution. Plates were incubated for 1 hour at 28° C. at each step. Addition of substrate solution and measurement of absorbance was done as described above.

TABLE 1

| | | Immunization protocol | | | |
|---|---|---|---|---|---|
| Group | Urease dose | Adjuvant | Adjuvant dose | Delivery route | Delivery schedule |
| 1 | none | none | — | — | — |
| 2 | 25 $\mu$g | LT | 1 $\mu$g | i.g. | days 0, 14, 28 |
| 3 | 10 $\mu$g | LT | 5 $\mu$g | s.c. | days 0, 28 |
| 4 | 10 $\mu$g | LT | 0.5 $\mu$g | s.c. | days 0, 28 |
| 5 | 10 $\mu$g | LT | 50 ng | s.c. | days 0, 14, 28 |
| 6 | 10 $\mu$g | LT | 5 ng | s.c. | days 0, 14, 28 |
| 7 | 10 $\mu$g | LT | 50 ng | i.d. | days 0, 14, 28 |
| 8 | 10 $\mu$g | LT | 5 ng | i.d. | days 0, 14, 28 |
| 9 | 10 $\mu$g | LTB | 50 $\mu$g | s.c. | days 0, 14, 28 |
| 10 | 10 $\mu$g | LTB | 5 $\mu$g | s.c. | days 0, 14, 28 |

TABLE 2

Serum IgG1 and IgG2a antibody responses following immunization with
urease alone or urease with LT, LTB, or alum adjuvants.
Median $\log_{10}$ titer (range)[a]

| Adjuvant | Antigen | Route[b] | IgG1 | IgG2a | IgG1/IgG2a ratio (range)[c] |
|---|---|---|---|---|---|
| 1 µg LT | 25 µg urease | oral | 3.1 (1.7–4.5) | 4.3 (1.7–5.2) | 0.2 (0.01–1.6) |
| 50 µg LTB | 25 µg urease | oral | 2.2 (1.7–4.7) | 3.5 (1.7–4.5) | 0.03 (0.01–5.2) |
| None | 10 µg urease | s.c. | 5.7 (5.5–6.3) | 4.8 (3.9–5.4) | 8.3 (3.9–56.7) |
| 10 ng LT | 10 µg urease | s.c. | 6.7 (6.3–7.2) | 5.3 (4.7–6.1) | 30.1 (1.9–257.7) |
| 5 µg LTB | 10 µg urease | s.c. | 6.3 (5.8–6.8) | 5.8 (5.2–6.4) | 4.7 (0.2–8.0) |
| 50 µg LTB | 10 µg urease | s.c. | 6.5 (6.0–6.9) | 6.2 (5.5–6.5) | 2.1 (0.7–5.8) |
| 10 ng LT + 50 µg LTB | 10 µg urease | s.c. | 6.8 (6.2–7.2) | 6.7 (6.2–6.9) | 1.0 (0.6–4.0) |
| Alum | 10 µg urease | s.c. | 6.6 (6.0–7.0) | 5.5 (4.8–5.8) | 11.8 (3.9–53.2) |

[a]Titers of urease-specific IgG1 and IgG2a were determined by ELISA. Titers are defined as 1/dilution of serum giving an $A_{405}$ of 0.1. Samples that were negative at the lowest dilution tested (1/100) were assigned a titer of 50 (1.7 $\log_{10}$).
[b]Adjuvant and antigen were mixed and delivered by the oral or subcutaneous (s.c.) routes.

All publications and patent applications mentioned herein are incorporated by reference. Other embodiments are within the following claims.

What is claimed is:

1. A method of inducing an immune response to Helicobacter in a mammal, said method comprising administering to said mammal by injection (a) an immunogenic *Helicobacter pylori* polypeptide that is admixed with (b) an adjuvant comprising immunogenic *Helicobacter pylori* polypeptide that is admixed with (b) an adjuvant comprising one or more of (i) heat-labile toxin of *Escherichia coli*, (ii) the B subunit of the heat-labile toxin of *Escherichia coli*, (iii) cholera toxin, and (iv) the B subunit of cholera toxin.

2. The method of claim 1, wherein the polypeptide and the adjuvant are provided together in a solution.

3. The method of claim 1, wherein the polypeptide comprises *Helicobacter pylori* urease or a subunit or immunogenic fragment thereof.

4. The method of claim 1, wherein the heat-labile toxin of *Escherichia coli* and the B subunit of the heat-labile toxin of *Escherichia coli* are administered to said mammal.

5. The method of claim 1, wherein said injection is subcutaneous.

6. The method of claim 1, wherein said injection is intradermal.

7. The method of claim 1, wherein said *Helicobacter pylori*polypeptide comprises catalase or an immunogenic fragment thereof.

8. The method of claim 1, wherein said *Helicobacter pylori* polypeptide comprises a polypeptide selected from the group consisting of HspA, HspB, lactoferrin receptor, p76 (SEQ ID NOs:1–22), p32 (SEQ ID NOs:23 and 24), BabA, BabB, AlpA, AlpB, and immunogenic fragments thereof.

9. The method of claim 1, further comprising administering to said mammal one or more additional immunogenic *Helicobacter pylori* polypeptides.

10. The method of claim 9, wherein said *Helicobacter pylori* polypeptide is urease and said one or more additional *Helicobacter pylori* polypeptides is selected from the group consisting of catalase, HspA, HspB, lactoferrin receptor, p76 (SEQ ID NOs:1–22), p32 (SEQ ID NOs:23 and 24), BabA, BabB, AlpA, AlpB, and immunogenic fragments thereof.

11. The method of claim 1, wherein said *Helicobacter pylori* polypeptide comprises a subunit of *Helicobacter pylori* urease.

12. The method of claim 1, wherein said *Helicobacter pylori* polypeptide comprises *Helicobacter pylori* catalase.

13. The method of claim 1, wherein said *Helicobacter pylori* polypeptide comprises a *Helicobacter pylori* polypeptide selected from the group consisting of catalase, HspA, HspB, lactoferrin receptor, p76 (SEQ ID NOs:1–22), p32 (SEQ ID NOs:23 and 24), BabA, BabB, AlpA, and AlpB.

14. A method of inducing a protective or therapeutic immune response to Helicobacter infection in a mammal, said method comprising administering to said mammal by injection (a) a polypeptide comprising a subunit of *Helicobacter pylori* urease that is admixed with (b) an adjuvant comprising one or more of (i) heat-labile toxin of *Escherichia coli*, (ii) the B subunit of the heat-labile toxin of *Escherichia coli*, (iii) cholera toxin, and (iv) the B subunit of cholera toxin.

* * * * *